US012605452B2

(12) United States Patent
Harki et al.

(10) Patent No.: US 12,605,452 B2
(45) Date of Patent: Apr. 21, 2026

(54) COMPOUNDS THAT DEGRADE KINASES AND USES THEREOF

(71) Applicants: Regents of the University of Minnesota, Minneapolis, MN (US); Regents of the University of California, La Jolla, CA (US)

(72) Inventors: Daniel A. Harki, Minneapolis, MN (US); Jian Tang, Minneapolis, MN (US); Ramkumar Moorthy, Bloomington, MN (US); Rommie E. Amaro, San Diego, CA (US); Ozlem Demir, San Diego, CA (US)

(73) Assignees: Regents of the University of Minnesota, Minneapolis, MN (US); Regents of the University of California, Oakland, CA (US)

( * ) Notice: Subject to any disclaimer, the term of this patent is extended or adjusted under 35 U.S.C. 154(b) by 1014 days.

(21) Appl. No.: 17/615,569

(22) PCT Filed: Jun. 3, 2020

(86) PCT No.: PCT/US2020/035977
§ 371 (c)(1),
(2) Date: Nov. 30, 2021

(87) PCT Pub. No.: WO2020/247537
PCT Pub. Date: Dec. 10, 2020

(65) Prior Publication Data

US 2022/0233702 A1 Jul. 28, 2022

Related U.S. Application Data

(60) Provisional application No. 62/856,385, filed on Jun. 3, 2019.

(51) Int. Cl.
*A61K 47/55* (2017.01)
*A61K 47/54* (2017.01)
*A61P 35/00* (2006.01)

(52) U.S. Cl.
CPC ............ *A61K 47/55* (2017.08); *A61K 47/545* (2017.08); *A61P 35/00* (2018.01)

(58) Field of Classification Search
CPC ....... A61K 47/55; A61K 47/545; A61P 35/00; C07D 471/04; C07D 487/04; C07D 401/14
See application file for complete search history.

(56) References Cited

U.S. PATENT DOCUMENTS

| | | | |
|---|---|---|---|
| 2014/0356322 | A1 | 12/2014 | Crews et al. |
| 2018/0169109 | A1 | 6/2018 | Bradner et al. |

FOREIGN PATENT DOCUMENTS

| | | | | |
|---|---|---|---|---|
| WO | WO-2016015604 A1 | 2/2016 | | |
| WO | WO-2017185031 A1 | 10/2017 | | |
| WO | WO-2018106870 A1 * | 6/2018 | ............. | A61K 31/44 |
| WO | WO-2018108870 A1 | 6/2018 | | |
| WO | WO-2020219650 A1 | 10/2020 | | |
| WO | WO-2020247537 A1 | 12/2020 | | |

OTHER PUBLICATIONS

Han, H., AAPS Pharmsci., 2000, 2, 1-11 (Year: 2000).*
"Canadian Application Serial No. 3,142,713, Voluntary Amendment filed Jun. 3, 2024", 20 pgs.
"European Application Serial No. 20818402.8, Extended European Search Report mailed Oct. 17, 2023", 11 pgs.
"International Application Serial No. PCT/US2020/035977, International Preliminary Report on Patentability mailed Dec. 16, 2021", 9 pgs.
Oleary, Ben, et al., "Treating cancer with selective CDK4/6 inhibitors", Nature Reviews Clinical Oncology, vol. 13, No. 7, [Online]. Retrieved from the Internet: <URL: https://www.nature.com/articles/nrclinonc.2016.26.pdf>, (Mar. 31, 2016), 417-430.
Toure, Momar, et al., "Small-Molecule Protacs: New Approaches to Protein Degradation", Angewandte Chemie International Edition, Verlag Chemie, Hoboken, USA, vol. 55, No. 6, (Jan. 12, 2016), 1966-1973.
"Application Serial No. PCT/US2020/035977, Invitation to Pay Additional Fees mailed Aug. 10, 2020", 3 pgs.
"International Application Serial No. PCT/US2020/035977, International Search Report mailed Nov. 9, 2020", 4 pgs.
"International Application Serial No. PCT/US2020/035977, Written Opinion mailed Nov. 9, 2020", 7 pgs.
"Canadian Application Serial No. 3,142,713, Office Action mailed Jun. 25, 2025", 8 pgs.

* cited by examiner

*Primary Examiner* — John S Kenyon
*Assistant Examiner* — Sara Elizabeth Bell
(74) *Attorney, Agent, or Firm* — Schwegman Lundberg & Woessner, P.A.

(57) ABSTRACT

The disclosure is directed to compounds of the Formula (I) or (II): A-$L^1$-B, A'-$L^1$-B, or a pharmaceutically acceptable salt, polymorph, prodrug, solvate or clathrate thereof, wherein A is an Aurora A ligand, A' is a CDK4/6 ligand; B is an E3 ligase ligand; and $L^1$ is a linker, as well as pharmaceutical compositions comprising such compounds, and methods for treating cancer using such compounds.

13 Claims, 24 Drawing Sheets

ABEMACICLIB

RIBOCICLIB

PALBOCICLIB

22

Ribociclib

11

12

13

14

15

| $K_d$ (nM) | Ribociclib | **11** | **12** | **13** | **14** | **15** |
|---|---|---|---|---|---|---|
| Aurora-A | 800 | 0.85 | 320 | 6.3 | 380 | 2.4 |
| CDK4-CyclinD1 | 2.8 | 3.0 | 42 | 52 | 310 | 61 |

| Cmpd **13** | %Ctrl @ 1μM | $K_d$ (nM) |
|---|---|---|
| Aurora A | 0.1 | 6.3 |
| Aurora B | 13 | 160 |
| Aurora C | 32 | 43 |
| CDK4-CyclinD1 | 3.3 | 52 |
| CDK4-CyclinD3 | 1.5 | 17 |
| CDK9 | 3.0 | 6.3 |
| CDK13 | 11 | 210 |
| EPHB6 | 4.5 | 150 |
| PI4KB | 5.3 | 220 |
| ROCK1 | 19 | >3,000 |
| TNK1 | 13 | 610 |
| TRKA | 5.3 | 24 |

Fig. 6B (continued)

| $IC_{50}$ (nM) | MCF-7 | HCC38 | Huh7 | IMR-32 | SK-N-BE(2) |
|---|---|---|---|---|---|
| **11** | 133 | 517 | 286 | n.d.[b] | n.d.[b] |
| **13** | 134 | 102 | 36.9 | 18.5 | 51.9 |
| **15** | 588 | 839 | 767 | 940 | 744 |
| Ribociclib | 51.0 | 30%[a] | 72%[a] | n.d.[b] | n.d.[b] |
| CD532 | n.d.[b] | n.d.[b] | n.d.[b] | 131 | 242 |

[a]Percentage of inhibition at 10 μM; [b]n.d. not determined.

*Fig. 9 (continued)*

Palbociclib

16

19

Abemaciclib

17

18

| $K_d$ (nM) | **16** | **17** |
|---|---|---|
| Aurora-A | 580 | 640 |
| CDK4-CyclinD1 | 170 | 23 |

COMPOUNDS THAT DEGRADE KINASES AND USES THEREOF

PRIORITY

This application is a U.S. National Stage Application under 35 U.S.C. § 371 from International Application Serial No. PCT/US2020/035977, filed on Jun. 3, 2020, and published as WO 2020/247537 A1 and published on Dec. 10, 2020, which claims the benefit of priority from U.S. Provisional Patent Application Ser. No. 62/856,385, filed on Jun. 3, 2019, which applications are hereby incorporated by reference in their entirety.

GOVERNMENT FUNDING

This invention was made with government support under CA234228 and GM110129 awarded by the National Institutes of Health. The government has certain rights in the invention.

This invention was made with government support under W81XWH-19-1-0336 awarded by the Department of the Army. The government has certain rights in the invention."

BACKGROUND

N-Myc is a member of the Myc family of transcription factors encoded by the MYCN proto-oncogene. Enhanced and deregulated expression of N-Myc drives the development of a number of human cancers, including neuroblastoma, medulloblastoma, neuroendocrine prostate cancer, and small-cell lung cancer, etc. For instance, in neuroblastoma MYCN amplification is the strongest indicator of poor prognosis. 5-year survival rates for low- or moderate-risk patients are 80-95%; for high-risk patients that typically have increased N-Myc levels, 5-year survival is only 50% although with more aggressive treatments. Despite recognition of its critical roles in neuroblastoma, N-Myc, like its homolog C-Myc, remains a challenge for drug discovery scientists. To date, there are no N-Myc targeted therapies available lor clinical use. A critical need remains unmet for the development of N-Myc modulators that could potentially yield a more effective therapeutic regimen for N-Myc driven cancers.

Ovarian cancer is the second most common and the most lethal gynecologic malignancy in the western world. In the United States alone, 22,240 new cases of ovarian cancer and 14,070 ovarian cancer deaths were estimated for 2018. Due to the lack of effective early detection methods, about 70% of ovarian cancer patients are diagnosed at an advanced stage, which is incurable in the majority of cases. The standard treatment for ovarian cancer is debulking surgery followed by platinum-based chemotherapy. However, many patients do not receive chemotherapy due to the high risk of side effects. Moreover, recurrence following initial therapy is very common in ovarian cancer and those tumors are frequently resistant to platinum-based chemotherapy. Accordingly, new and innovative therapeutic strategies for regulating the proliferation of ovarian cancer cells are needed.

BRIEF DESCRIPTION OF THE DRAWINGS

FIG. 5A is N-Myc depletion through the induced Aurora-A conformational change by Type II Aurora-A inhibitors.

FIG. 6A shows chemical structures of representative compounds and their binding affinity with Aurora-A and CDK4-CyclinD1. Values shown are in nM.

FIG. 7A is the time-dependent degradation of Aurora-A and CDK4 with 0.1 μM compound 13. FIG. 7B is the dose-dependent degradation of Aurora-A and CDK4 after 4 hours treatment. FIG. 7C is the quantifications and curve fitting of the time- and dose-dependent degradation of Aurora-A and CDK4. FIG. 7D is the degradation of Aurora-A by compound 13 requires target engagement of both Aurora-A and E3 ligase CRBN, and is UPS-dependent. In indicated lanes, cells were pre-treated with compound 11, Thalidomide, MG-132 and MLN4924 for one hour before adding compound 13. Thalidomide: CRBN ligand; MG-132: proteasome inhibitor; MLN4924: Cullin-RING E3 ligase inhibitor. Incubation time was 4 hours. FIG. 7E is the cell cycle analysis with compound treatment for 48 hours. FIG. 7F. is the abundance of downstream signaling proteins treated with compound 13 for 4 hours and 24 hours, respectively FIGS. 8A and B are the degradation of Aurora-A and N-Myc in MYCN amplified neuroblastoma cells.

DESCRIPTION

N-Myc (encoded by MYCN), a member of the Myc family of transcription factors, is a central regulator of a range of cellular processes. Amplification of MYCN is a driver mutation in a number of tumors types, including neuroblastoma (20%), medulloblastoma (5%), small-cell lung cancer (15%-20%), and neuroendocrine prostate cancer (NEPC, 40%) etc. MYCN amplification has been associated with poor prognosis in a variety of cancers. For instance, in neuroblastoma MYCN amplification is the strongest indicator of poor prognosis, and patients with high N-Myc protein levels often requires more aggressive treatments. Current standard of care for neuroblastoma includes surgery, chemotherapy and radiation therapy. Although the 5-year survival rates for low- or moderate-risk patient are 80-95%, for high-risk patients that typically have increased N-Myc levels, 5-year survival is only 50%. To date, there are no N-Myc targeted therapies available for clinical use. A critical need remains unmet for the development of N-Myc modulators that could potentially yield a more effective therapeutic regimen for N-Myc driven cancers.

Figure 5A:
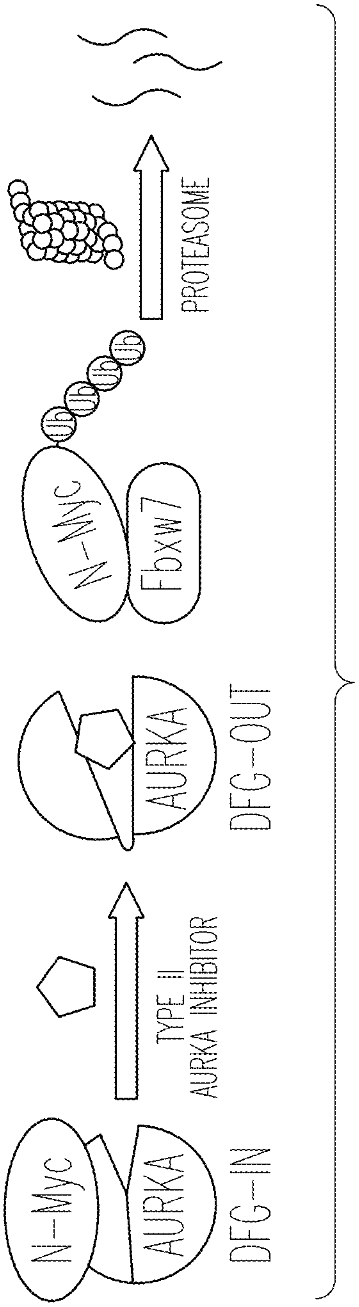
FIG. 5A&B are two different chemical strategies for N-Myc depletion.

N-Myc, like its homolog C-Myc, is a difficult target for drug discovery scientists due to a lack of surfaces suitable for small molecule binding. Therefore, therapeutic strategies for controlling N-Myc, function must operate outside of direct binding. The concentration of N-Myc, in cells is tightly regulated through proteasomal degradation. Previous work has shown that MYCN amplified cancers often overexpress Aurora kinase A (Aurora-A) to prevent the degradation of N-Myc by forming an Aurora-A/N-Myc protein complex. More specifically, N-Myc binds to Aurora-A in the DFG-in conformational state, and this protein-protein interaction blocks the recognition motif on N-Myc from its native E3 ubiquitin ligase, Fbxw7. Therefore, overexpressed Aurora-A stabilizes N-Myc protein and prevent its proteasomal degradation mediated by Fbxw7. Based on this observation, a class of Type II kinase inhibitors have been developed to induce a significant conformational change of Aurora-A from DFG-in to DFG-out that could displace N-Myc, resulting in Fbxw7 recognition and subsequent degradation (FIG. 5*a*). However, these compounds function through a competitive mechanism against N-Myc, and their efficacy in cells depends on the level of N-Myc overexpression, which differs widely in neuroblastoma patients and correlates with disease progression. Consistent with this, early clinical trial results suggest limited therapeutic benefits for late-stage neuroblastoma and NEPC patients with overexpressed N-Myc. Therefore, a critical need remains for the development of N-Myc modulators that function through unique mechanisms of action.

Cyclin D-CDK4/6 complexes mediate G1-to-S phase cell cycle progression and deregulated cyclin D-CDK4/6 activity contributes to the aberrant proliferation of human cancers, including ovarian cancer. Recent studies have showed that inhibition of CDK4/6 kinase function alone is not sufficient to induce cell cycle arrest, whereas cyclin D1 deficiency sensitizes ovarian cancer cells to CDK4/6 inhibition. Targeting cyclin D1 in concert with CDK4/6 inhibition represents a promising strategy for harnessing the growth of ovarian cancer cells. This disclosure constitutes an experimental attempt to exploit the synthetic lethality between cyclin D1 and CDK4/6 in ovarian cancer. This disclosure also represents a significant advance due to the strategy to degrade CDK4/6 and downregulate Cyclin D1 levels simutanously using a single compound, thereby achieveing the synergistic therapeutic effects for ovarian cancer.

Figure 1:
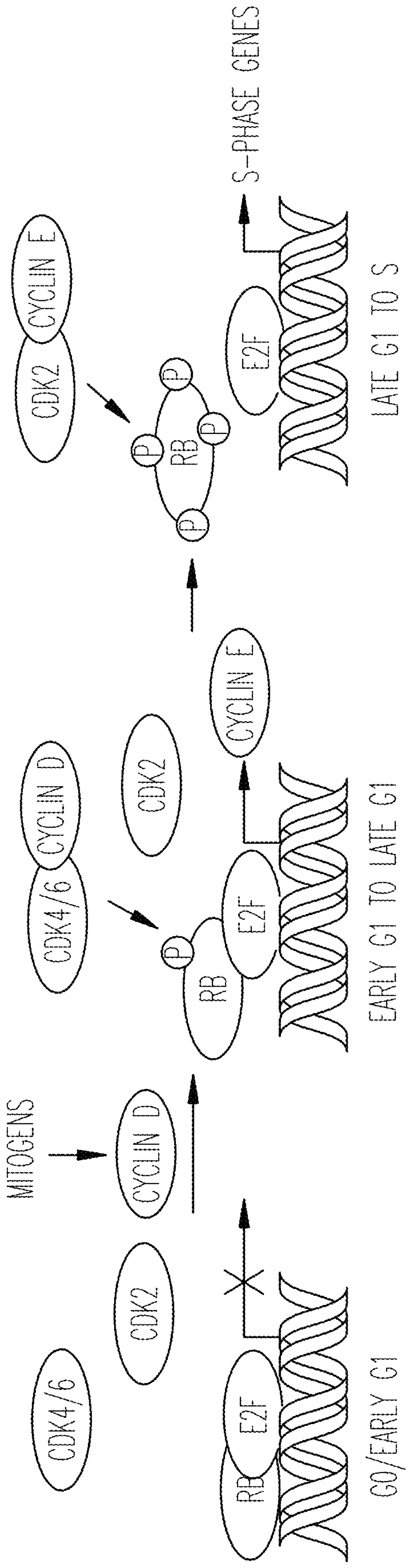
FIG. 1 is a cartoon showing G1-to-S phase transition and the roles of cyclin D-CDK4/6 complexes.
Figure 2:
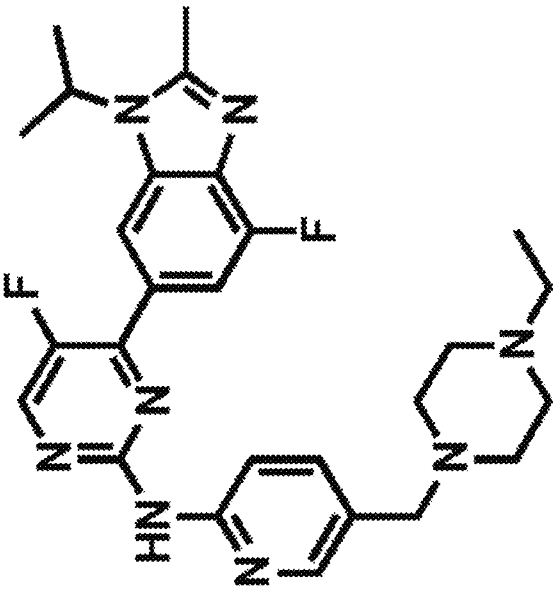
FIG. 2 are chemical strutures of three CDK4/6 inhibitors.
Figure 2:
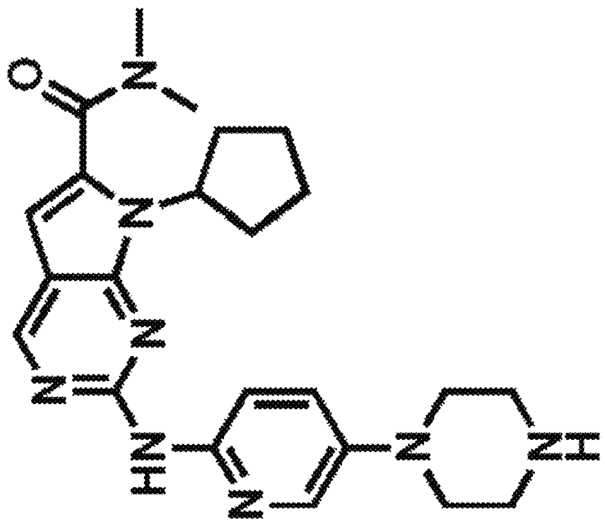
Figure 2:
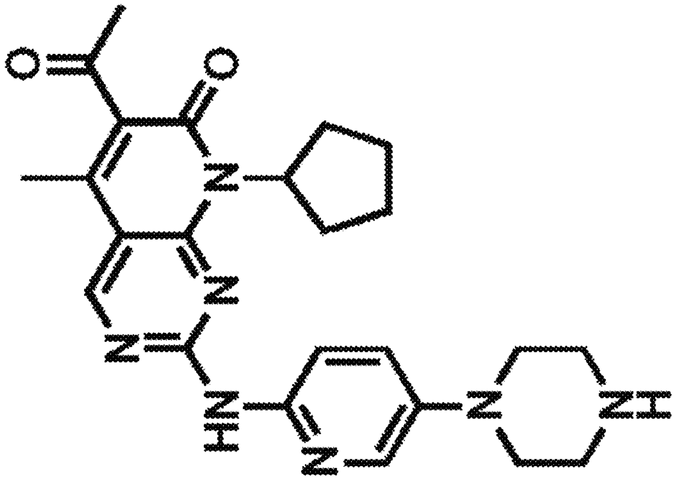

Aberrant cell proliferation is a hallmark of ovarian cancer and human cancers in general. Targeting key drivers of cell-cycle progression represents a promising strategy for controlling unregulated cell growth, which, if successful, may confer therapeutic benefits. D-type cyclins mediate G1-to-S phase cell cycle progression through activation of cyclin-dependent kinases 4 and 6 (CDK4/6). In resting cells, the low level of D-type cyclins limit CDK4/6 kinase activity. In this state, retinoblastoma protein, RB1, is hypophosphorylated and RB1 inhibits the transcriptional activity of E2F. However, mitogenic stimulation upregulates the transcription of cyclin D (in early G1 stage), which partially activates E2F that enables the transcription of E-type cyclins. As cyclin E levels rise in late G1 stage, CDK2 is activated, which then hyperphosphorylates RB1 resulting in its release from E2F and full activation of E2F-mediated gene expression, including the production of genes requires for entry into S phase of the cell cycle (FIG. 1A). Given their central roles in mediating the G1-to-S transition, cyclin D-CDK4/6 complexes represent validated molecular targets for stopping cancer cell division. Previous research has mainly focused on modulating CDK4/6 kinases and three inhibitors palbociclib, ribociclib, and abemaciclib have received FDA approval for treating breast cancers with dysregulated CDK4/6 activation (FIG. 1B). Efforts to repurpose those drugs for treating ovarian cancer have mainly focused on identifing those patient subgroups that could benefit from CDK4/6 inhibition. However, several in vitro studies have shown that most ovarian cancer cell lines are not sensitive to CDK4/6 inhibitors alone, which suggests they have limited utilities in ovarian cancer therapy.

The cyclin Ds have received substantially less attention from drug discovery scientists than CDK4/6 kinases, which is surprising given their critical roles in regulating cell cycle progression. Three cyclin D isoforms (D1/D2/D3) have been shown to have differential expression profiles in tissue with cyclin D1 being frequently overexpressed in a variety of human cancers and associated with tumorigenesis and metastasis. An estimated 26% of sporadic epithelial ovarian cancers (EOC) overexpress cyclin D1, which has been attributed to poor prognosis and decreased survival in EOC patients. Cyclin D1-proficient ovarian cancer cells were shown to be resistant to CDK4/6 inhibition, whereas cyclin D1-deficiency substantially increased the sensitivity of ovarian cancer cells to small molecule CDK4/6 inhibitors (Xue, Y.; Meehan, B.; Macdonald, E.; et. al. *Nat. Commun.* 2019, 10, 558). This observation is not limited to ovarian cancer cells, as cyclin D1-deficient non-small cell lung cancer (NSCLC) cells were similarly shown to be sensitive to CDK4/6 inhibitors. Furthermore, overexpression of cyclin E has been clinically validated as one of the main mechanisms for CDK4/6 inhibitor resistance in breast cancer patients, while induced cyclin D1 degradation is sufficient to elicit G1 cell cycle arrest despite overexpression of cyclin E2 in ovarian cancer cells. These findings validate that cyclin D1 deficiency is synthetic lethal with CDK4/6 inhibition in cancer cells and targeting cyclin D1 in concert with CDK4/6 inhibition may confer antiproliferative effects in ovarian cancer cells that, if successful, may constitute a new therapeutic regimen.

Compounds of the Disclosure

The present disclosure provides a compound of the Formula (I):

$$A\text{-}L^1\text{-}B \qquad \text{Formula (I)}$$

or a pharmaceutically acceptable salt, polymorph, prodrug, solvate or clathrate thereof, wherein A is an Aurora A ligand; B is an E3 ligase ligand; and $L^1$ is a linker. A can, in turn be, a group of the formula X—Y—Z, wherein $L^1$ is covalently attached to X, wherein X is an aryl or heterocyclyl group; Y is a heterocyclyl group; and Z is a heterocyclyl or a cycloalkyl group.

The present disclosure also provides a compound of the Formula (II):

A'-$L^1$-B Formula (II)

or a pharmaceutically acceptable salt, polymorph, prodrug, solvate or clathrate thereof, wherein A' is a CDK4/6 ligand; B is an E3 ligase ligand; and $L^1$ is a linker. A' can, in turn be, a croup of the formula X—Y—Z, wherein $L^1$ is covalently attached to X, wherein X is an aryl or heterocyclyl group; Y is a heterocyclyl group; and Z is a heterocyclyl or a cycloalkyl group. Thus, for example, the compound of Formula (I) or (II) is a compound of Formula (III):

Z—Y—X-$L^1$-B Formula (III)

or a pharmaceutically acceptable salt, polymorph, prodrug, solvate or clathrate thereof. Thus, for example, X is a five- or six-memebered aryl or heterocyclyl group; Y is a six- to ten-membered heterocyclyl group; and Z is a cycloalkyl group or a six- to ten-membered heterocyclyl group.

For example, X is a group of the formula:

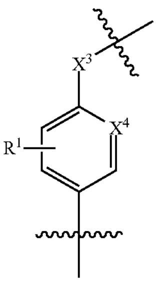
, and Y is a group of the formula:

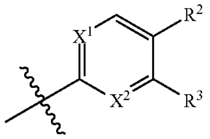

wherein $X^1$, $X^2$, and $X^4$ are each independently CH or N; $X^3$ is -alkyl-, —O—, —S— or $NR^4$, wherein $R^4$ is H or alkyl; and $R^1$ is H, halo, amino, alkyl, aryl or heterocyclyl; $R^2$ is Z, H, halo, alkyl, aryl or heteroaryl; and $R^3$ is Z, H, halo, alkyl, aryl or heteroaryl; or $R^2$ and $R^3$, together with the carbon atoms to which they are attached, form a heterocyclyl group substituted with Z and up to three substituents.

For example, Y is a group of the formula:

(a)

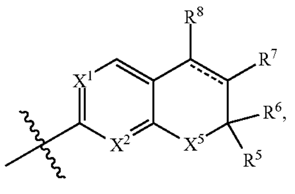

-continued (b)

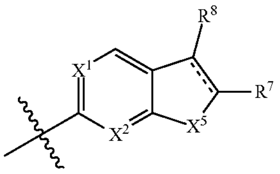

or (c)

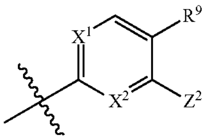

wherein the dashed line in (a) or (b) form a double bond; $X^1$ and $X^2$ are as defined herein; $X^5$ is N—$Z^1$ or CH—$Z^1$; $R^5$ and $R^6$ are each, independently H or alkyl or $R^5$ and $R^6$, together with the carbon to which they are attached, form a carbonyl group (═O) or cycloalkyl; $R^7$ and $R^8$ are each, independently H, alkyl, aryl, amino, acyl or amino; and $R^9$ is H, halo or alkyl. Examples of the groups (a) and (b) include croups of the formulae (a)', (b)', (a)'', (b)'', and (a)*:

(a)'

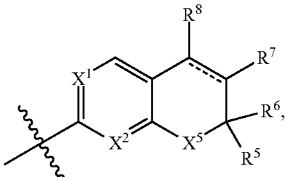

(b)'

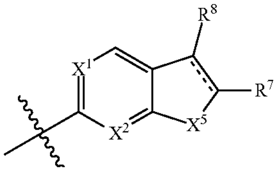

or (a)''

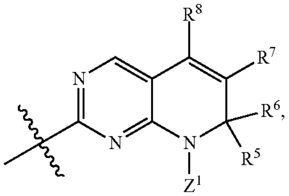

(b)''

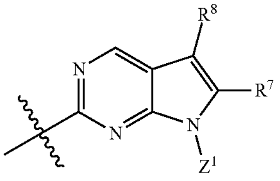

or (a)*

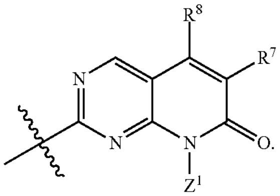

$Z^1$ is a cycloalkyl group, such as a $C_3$-$C_6$-cycloalkyl group, including cyclopropyl, cyclobutyl, cyclopentyl, and cyclohexyl. Thus, for example, the groups (a)", (b)", and (a)* is:

(a)"

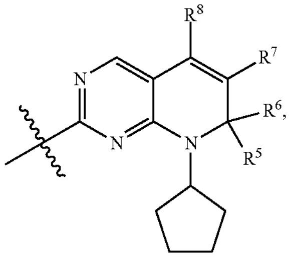

(b)"

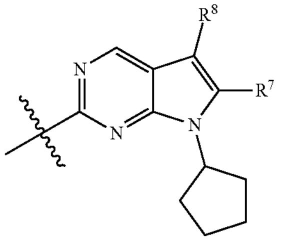

or (a)*

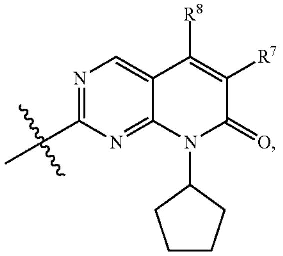

such as:

(a)*

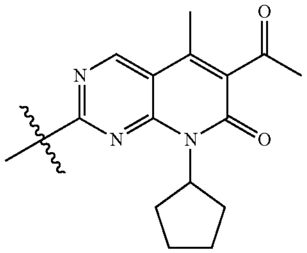

, or (b)"

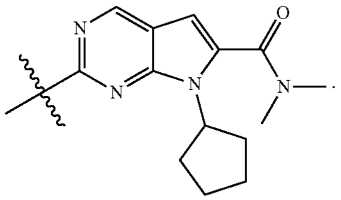

$Z^2$ is a heterocyclyl group of the formula:

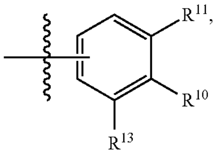

such as

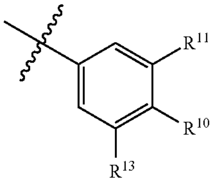

or

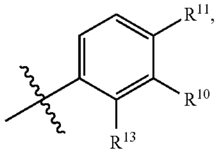

wherein $R^{10}$ and $R^{11}$ together with the carbon atoms to which they are attached form a five- or six-membered heterocyclyl group; and $R^{13}$ is H, halo or alkyl. For example, $Z^2$ is a heterocyclyl group of the formula:

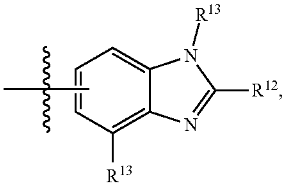

such as

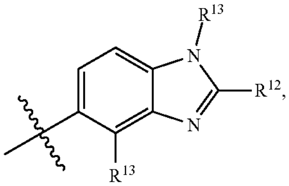

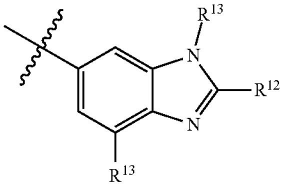

including

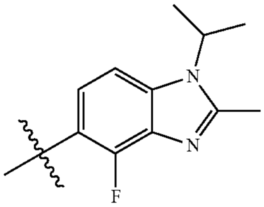

and

-continued

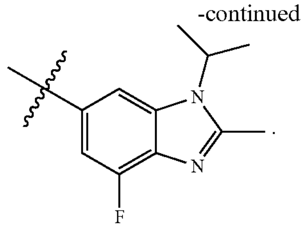

wherein $R^{13}$ is as defined herein; wherein the dashed line forms a double bond; $X^6$ and $X^7$ are each, independently, O, N, S, $CR^{13}$, $C(R^{13})_2$ or $NR^{13}$, wherein $R^{13}$ is H or alkyl; and $R^{12}$ is H, alkyl or aryl. For example, $Z^2$ is a heterocyclyl group of the formula:

such as

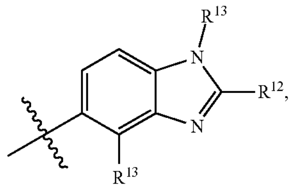

including

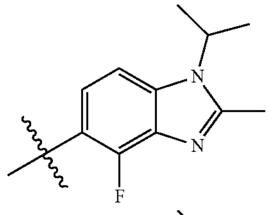

and

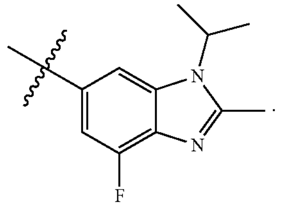

In addition, the group B is a group of the formula G-T, wherein G is a heterocyclyl group and T is a heterocyclyl group different from G; or B is a group of the formula —C(O)—$AA^1$-$AA^2$-$NR^aR^b$, wherein $AA^1$ and $AA^2$ is a naturally occurring or a non-naturally occurring amino acid, $R^a$ is H or alkyl, and $R^b$ is alkylaryl. Thus, for example, the compound of Formula (I) and (III) is compounds of Formulae (IV) and (V), respectively:

A-$L^1$-G-T    Formula (IV)

Z—Y—X-$L^1$-G-T    Formula (V)

or a pharmaceutically acceptable salt, polymorph, prodrug, solvate or clathrate thereof.

G is a heterocyclyl group of the formula:

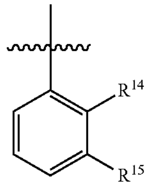

wherein $R^{14}$ and $R^{15}$ together with the carbon atoms to which they are attached form a five- or six-membered heterocyclyl group to which T is attached. For example, G is a heterocyclyl group of the formula:

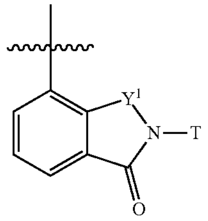

wherein $Y^1$ is $CH_2$ or C(O).

T is, for example, a five- or six-membered heterocyclyl group, such as a group of the formula;

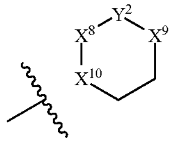

wherein $X^8$ and $X^9$ are each independently $CR^{16}R^{17}$, wherein $R^{16}$ and $R^{17}$ are each independently H, alkyl or, $R^{16}$ and $R^{17}$ together with the atom to which they are attached form a C(O) group; $X^{10}$ is N or $CR^{18}$, wherein $R^{18}$ is H or alkyl; and $Y^2$ $NR^{19}$, wherein $R^{19}$ is H or alkyl. Thus, for example, T is a group of the formula:

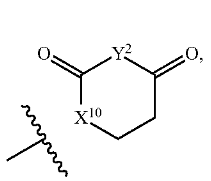

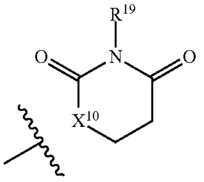

or

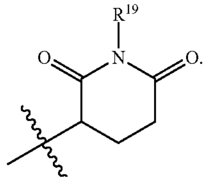

The group —C(O)—$AA^1$-$AA^2$-$NR^aR^b$ is a group of the formula:

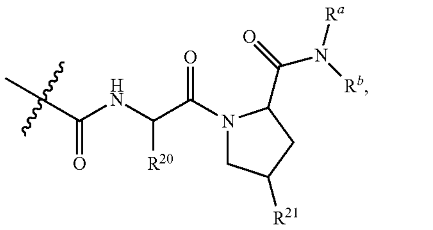

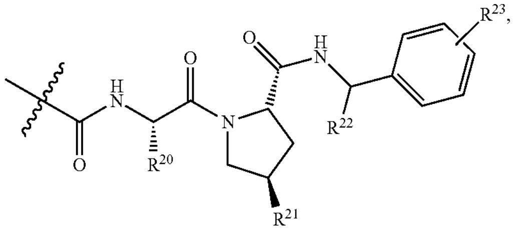

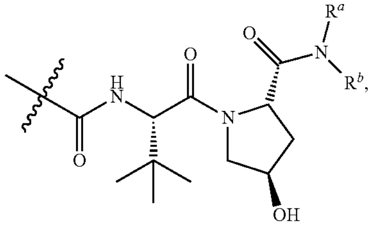

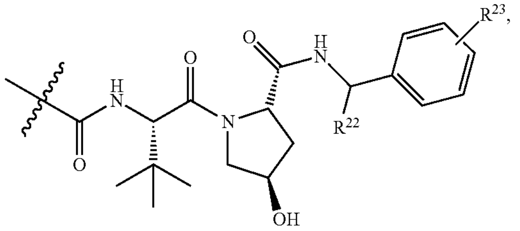

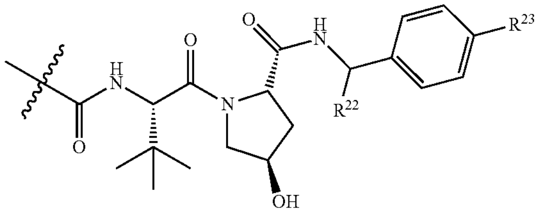

or

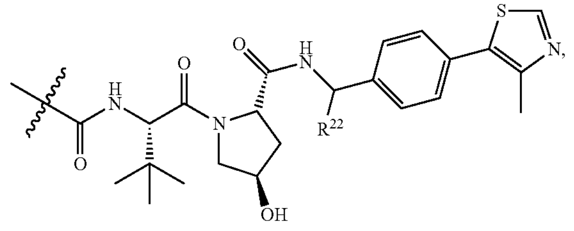

wherein $R^{20}$ is the side-chain of a naturally or a non-naturally occurring amino acid, such as H (i.e., glycine), alkyl (e.g., alanine, valine, isoleucine, and leucine, as well as t-butyl), -alkyl-S-alkyl (e.g., methionine), arylalkyl (e.g., phenylalanine, tyrosine, and tryptophan), and the like; $R^{21}$ is H, alkyl or $OR^{24}$, wherein $R^{24}$ is H or alkyl; $R^{22}$ is H, halo or alkyl; and $R^{23}$ is a heterocyclyl group, such as a five- or six-membered heterocyclyl group, such as a thiazolyl group. The atom to which $R^{20}$, $R^{21}$, and $R^{22}$ are attached can each be chiral and can each have any suitable relative configuration, such as a D- or L-configuration, independent of each other.

In compounds of Formulae (I)-(V), $L^1$ is acyl, alkyl, alkenyl or alkynyl, and combinations thereof, optionally interrupted by one or more heteroatoms, such as —O—, and —$S(O)_n$— (wherein n is 0, 1 or 2). Examples of linkers include -alkyl-$X^{11}$-alkyl- and -alkyl-$X^{11}$-alkynyl-linkers, and combinations thereof, wherein $X^{11}$ is a bond, alkyl, —O—, —$NR^{13}$—, and —$S(O)_n$—, that can comprise one or more spacer groups, such as alkyl, acyl, amino, and amido groups within the linker or at one or both termii. Thus, for example, $L^1$ is -(alkyl-$X^{11}$)$_g$-alkyl-, -(alkyl-$X^{11}$)$_g$-alkynyl-, —C(O)$NR^{13}$—$X^{11}$-(alkyl-$X^{11}$)$_g$-alkyl-, —C(O)$NR^{13}$—$X^{11}$-(alkyl-$X^{11}$)$_g$-alkyl-C(O)—, —C(O)$NR^{13}$—$X^{11}$-(alkyl-$X^{11}$)$_g$-alkynyl-, —C(O)$NR^{13}$—$X^{11}$— (alkyl-$X^{11}$)$_g$-alkynyl-C(O)—, —C(O)$NR^{13}$—$X^{11}$-(alkyl-$X^{11}$)$_g$-alkyl-$NR^{13}$—, —C(O)$NR^{13}$—$X^{11}$— (alkyl-$X^{11}$)$_g$-alkyl-C(O)—$NR^{13}$—, —C(O)$NR^{13}$—$X^{11}$-(alkyl-$X^{11}$)$_g$-alkynyl-$NR^{13}$—, —C(O)$NR^{13}$—$X^{11}$-(alkyl-$X^{11}$)$_g$-alkynyl-C(O)—$NR^{13}$—, —$NR^{13}$—$X^{11}$-(alkyl-$X^{11}$)$_g$-alkyl-, —$NR^{13}$—$X^{11}$-(alkyl-$X^{11}$)$_g$-alkyl-C(O)—, —$NR^{13}$—$X^{11}$-(alkyl-$X^{11}$)$_g$-alkynyl-, —$NR^{13}$—$X^{11}$-(alkyl-$X^{11}$)$_g$-alkynyl-C(O)—, —$NR^{13}$—$X^{11}$-(alkyl-$X^{11}$)$_g$-alkyl-$NR^{13}$—, —$NR^{13}$—$X^{11}$-(alkyl-$X^{11}$)$_g$-alkyl-O—, —$NR^{13}$—$X^{11}$-(alkyl-$X^{11}$)$_g$-alkynyl-C(O)—, —$NR^{13}$—$X^{11}$-(alkyl-$X^{11}$)$_g$-alkyl-$NR^{13}$—, —$NR^{13}$—$X^{11}$-(alkyl-$X^{11}$)$_g$-alkyl-O—, —$NR^{13}$—$X^{11}$-(alkyl-$X^{11}$)$_g$-alkyl-C(O)—$NR^{13}$—, —$NR^{13}$—$X^{11}$-(alkyl-$X^{11}$)$_g$-alkynyl-$NR^{13}$—, —$NR^{13}$—$X^{11}$-(alkyl-$X^{11}$)$_g$-alkynyl-C(O)—$NR^{13}$, —C(O)—$X^{11}$-(alkyl-$X^{11}$)$_g$-alkyl-, —C(O)—$X^{11}$-(alkyl-$X^{11}$)$_g$—alkyl-, —C(O)—$X^{11}$-(alkyl-$X^{11}$)$_g$-alkyl-C(O)—, —C(O)—$X^{11}$-(alkyl-$X^{11}$)$_g$-alkynyl-, —C(O)—$X^{11}$-(alkyl-$X^{11}$)$_g$-alkynyl-C(O)—, —C(O)—$X^{11}$-(alkyl-$X^{11}$)$_g$-alkyl-$NR^{13}$—, —C(O)—$X^{11}$-(alkyl-$X^{11}$)$_g$-alkyl-C(O)—$NR^{13}$—, —C(O)—$X^{11}$-(alkyl-$X^{11}$)$_g$—alkynyl-$NR^{13}$—, —C(O)—$X^{11}$-(alkyl-$X^{11}$)$_g$-alkynyl-C(O)—$NR^{13}$—, —NH—$X^{11}$—C(O)—$X^{11}$-alkylyl- and combinations thereof, wherein g is an integer from 0 to 20 (e.g., 0 to 10, 0 to 5, 1 to 3, 1 to 5, 4 to 10, 2 to 10, 2 to 5 or 3 to 9) and each group (alkyl-$X^{11}$) being the same or different. Examples of $L^1$ include:

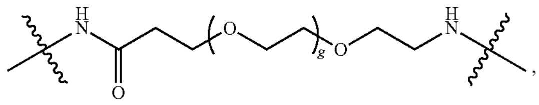

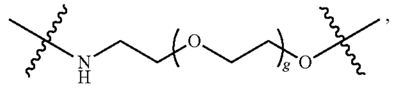

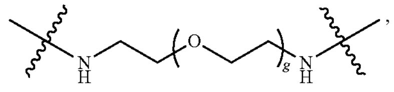

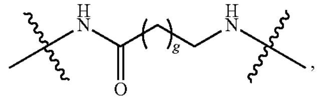

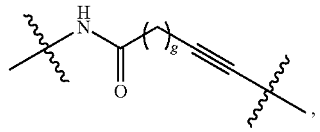

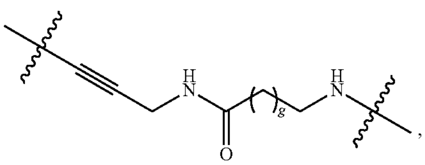

and

-continued
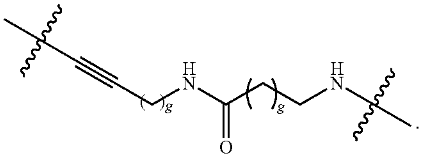
Examples of compounds of the Formulae (I)-(V) include compounds of the formulae:
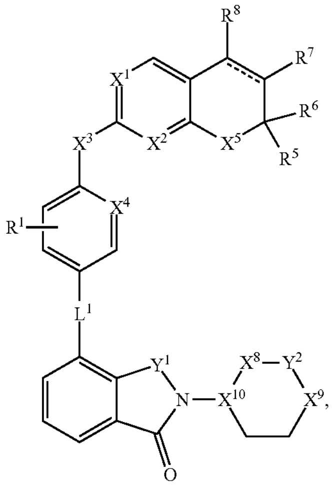
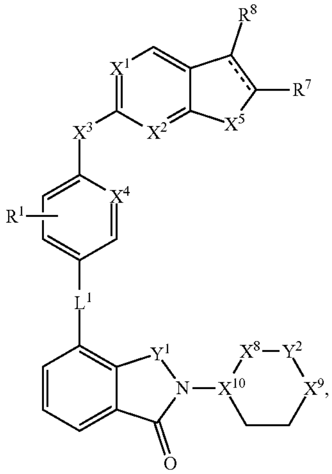
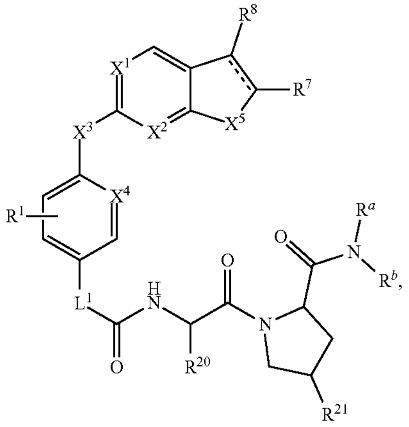
-continued
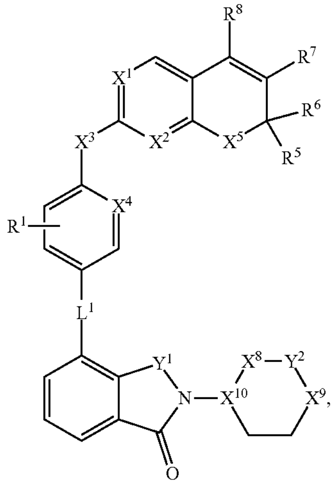
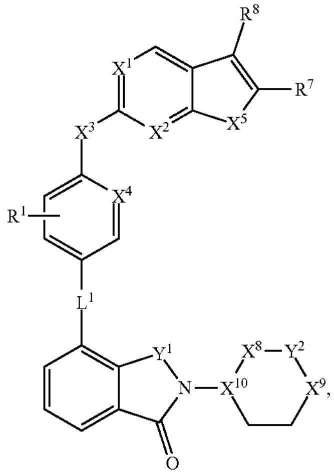
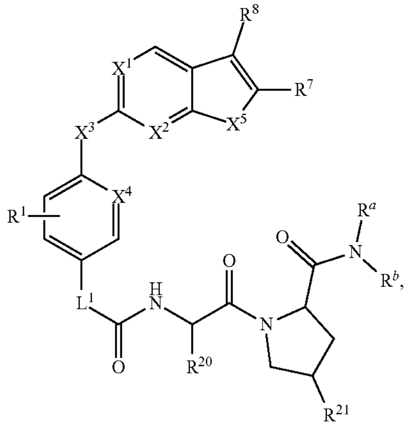

-continued
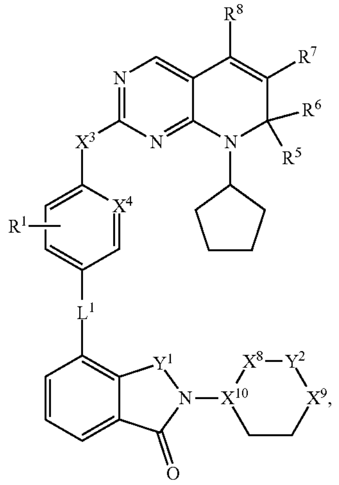
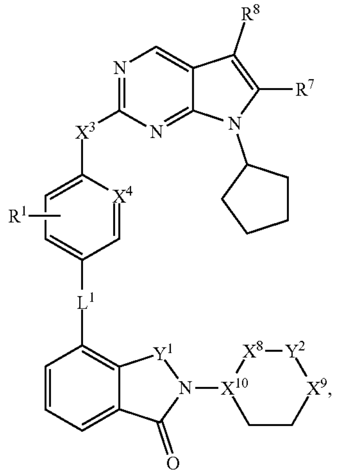
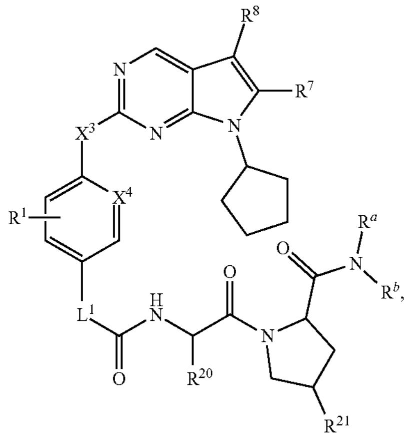
-continued
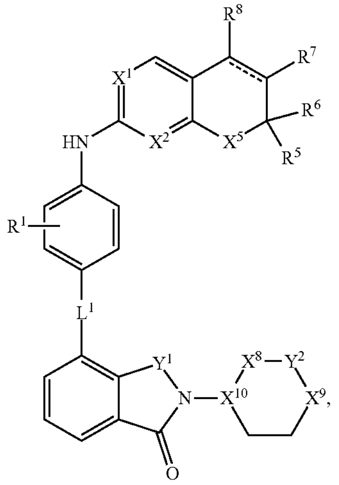
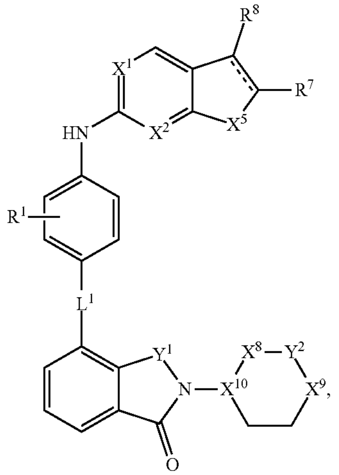
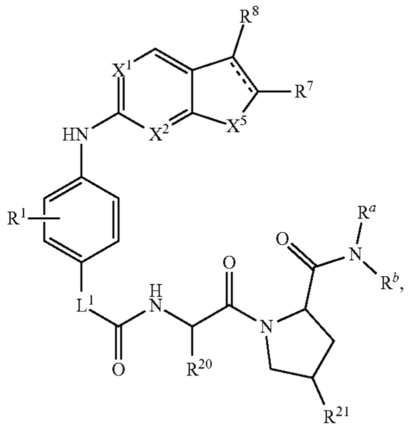

-continued
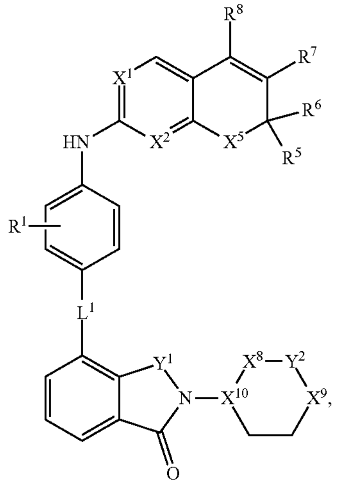
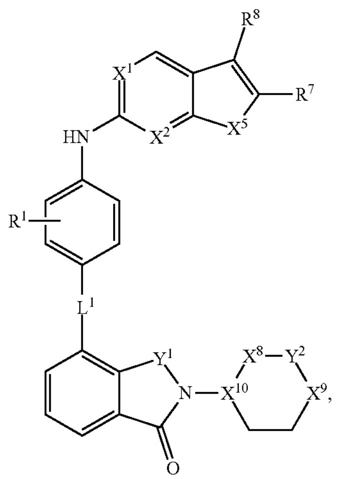
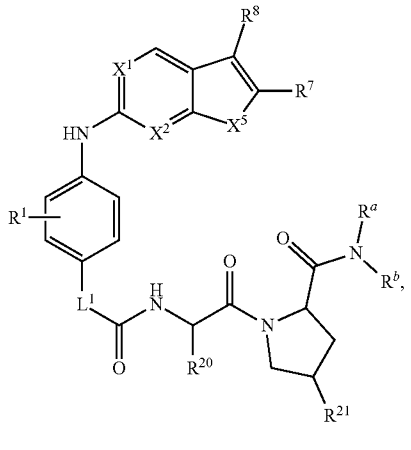
-continued
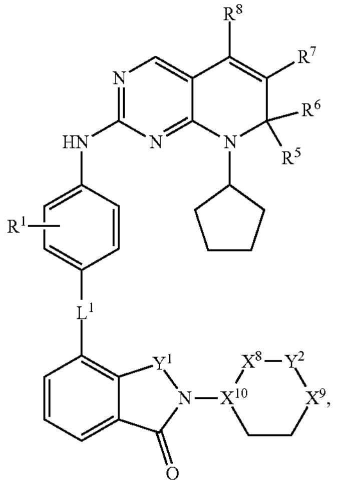
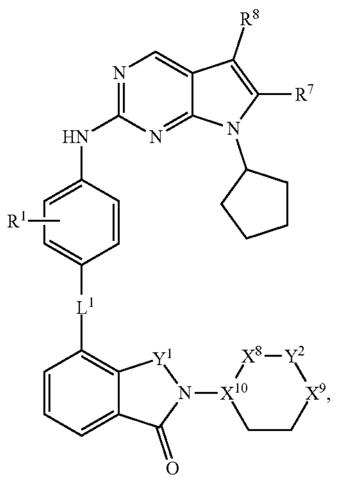
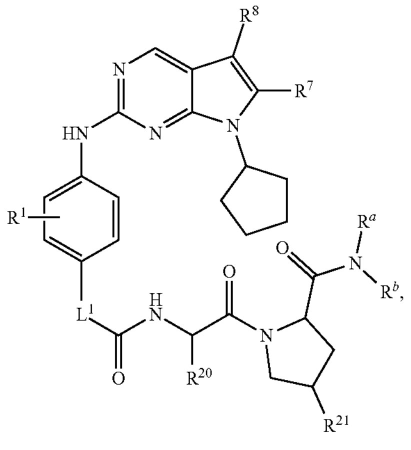

-continued
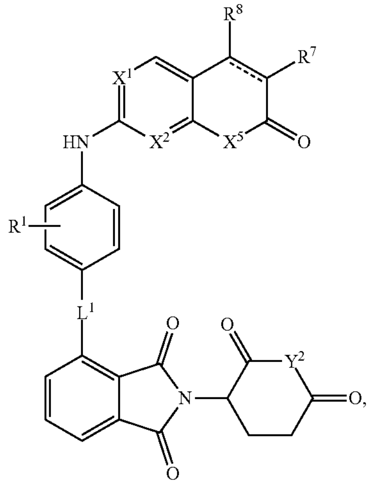
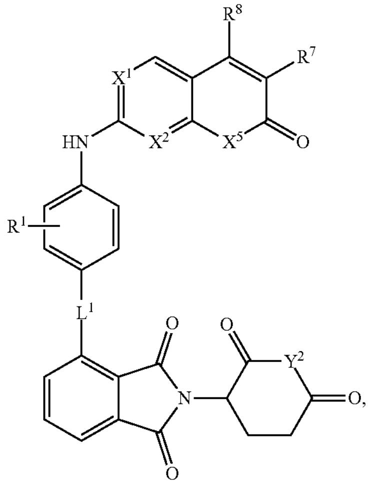
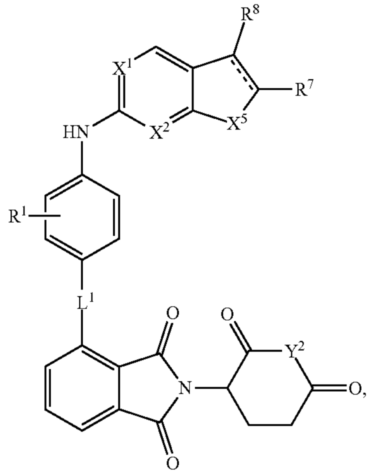
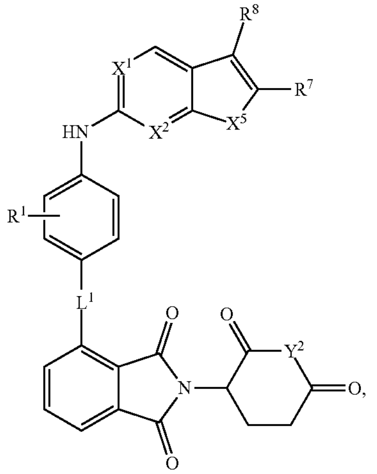
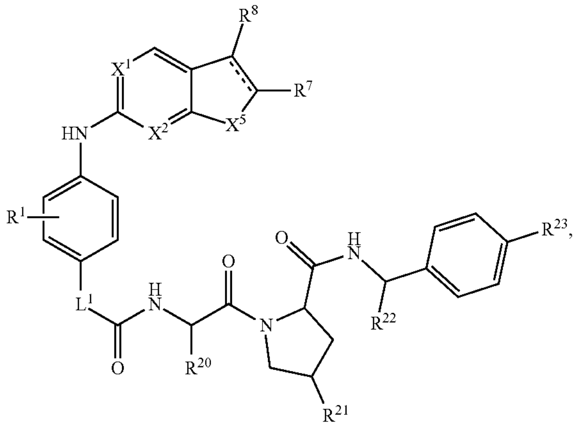
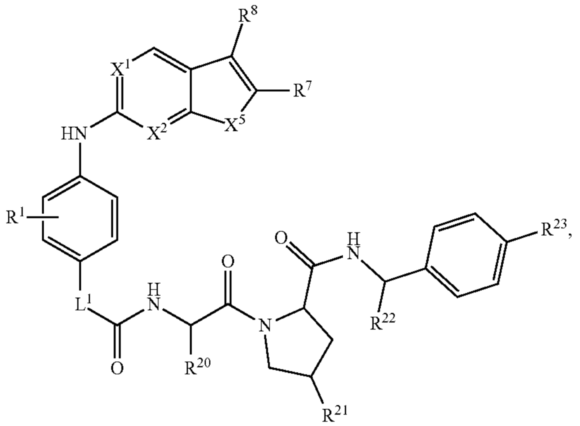

-continued
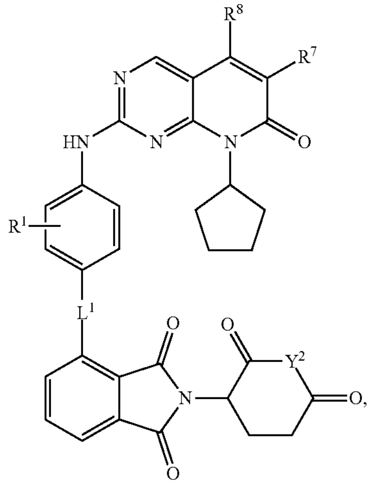
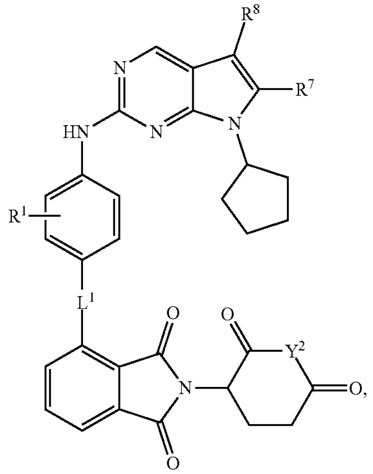
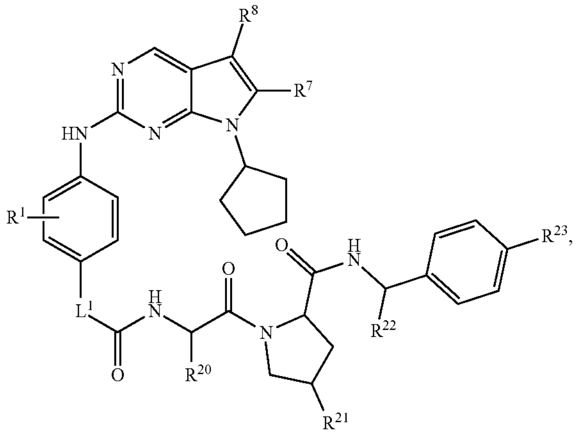
-continued
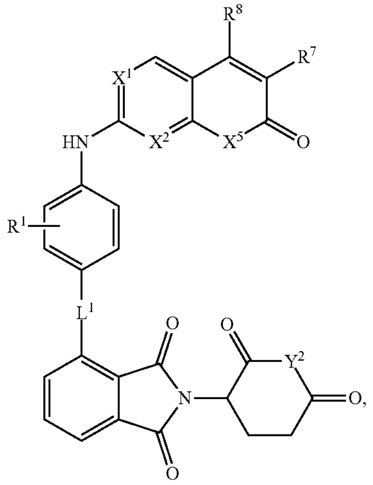
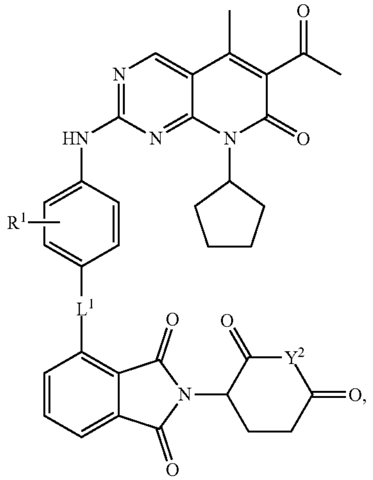
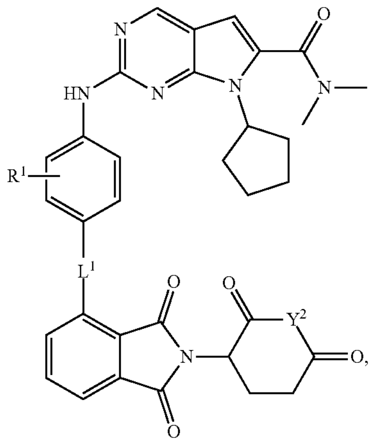

-continued
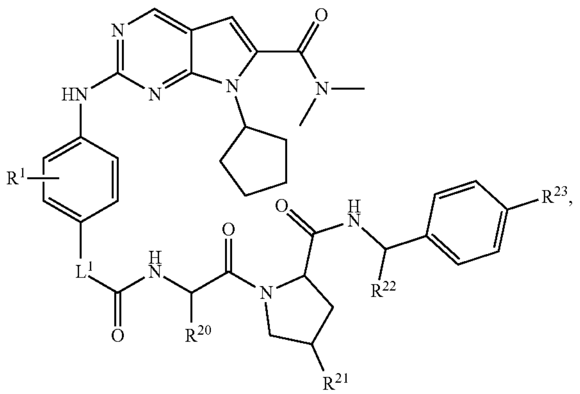
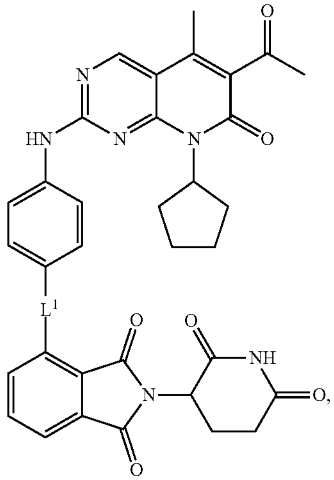
-continued
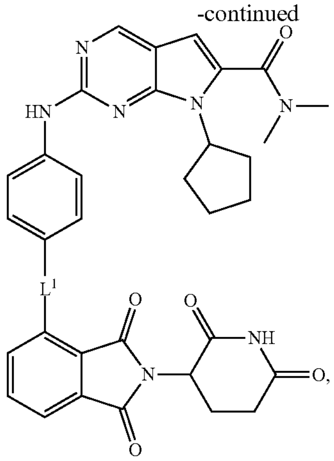
and
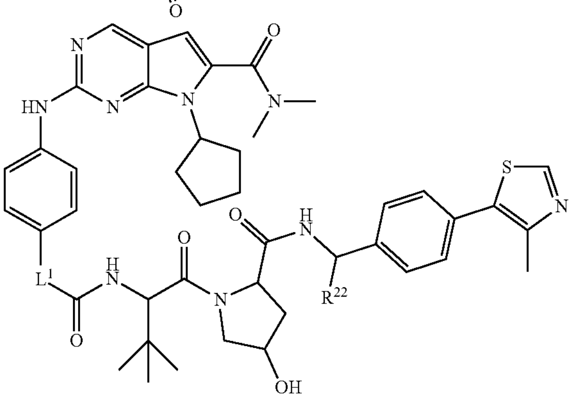
or a pharmaceutically acceptable salt, polymorph, prodrug, solvate or clathrate thereof.
Examples of compounds of the Formula (I)-(V) also include compounds of the formulae:
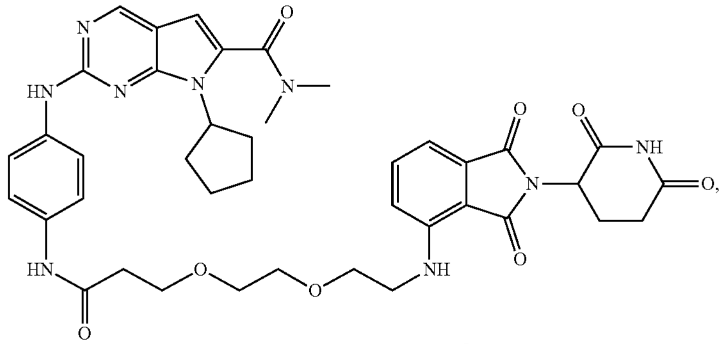
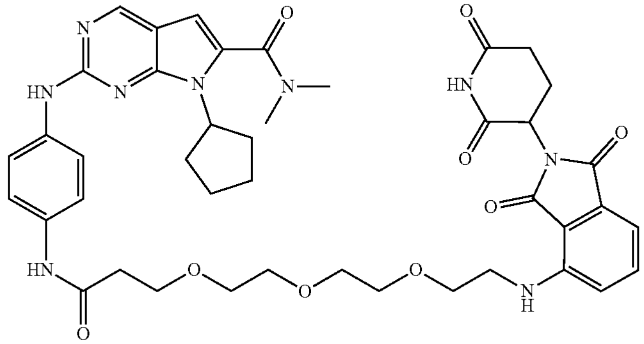
, -continued
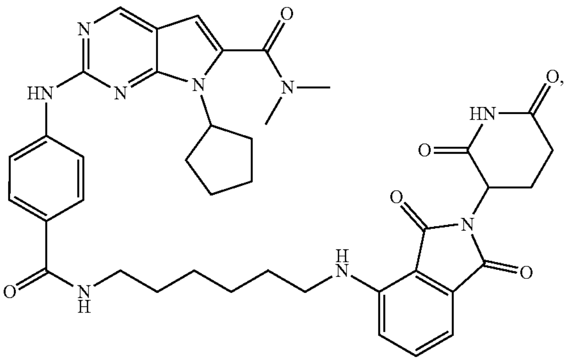
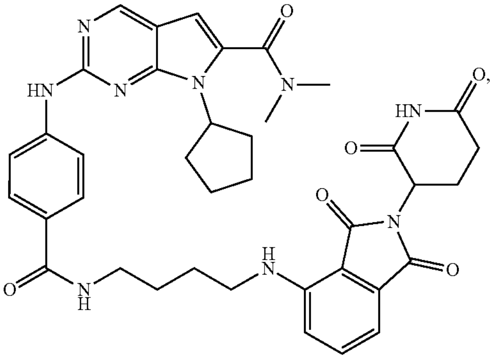
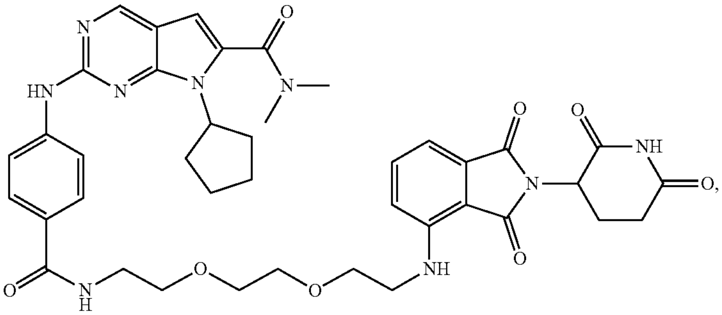
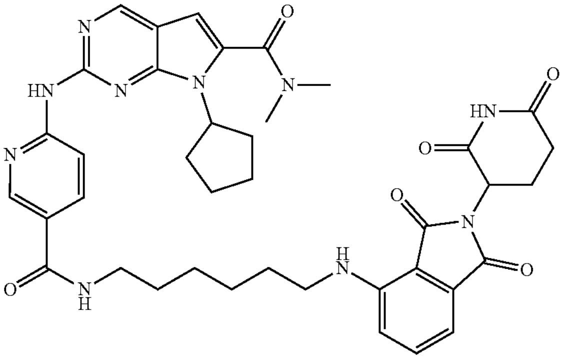
,
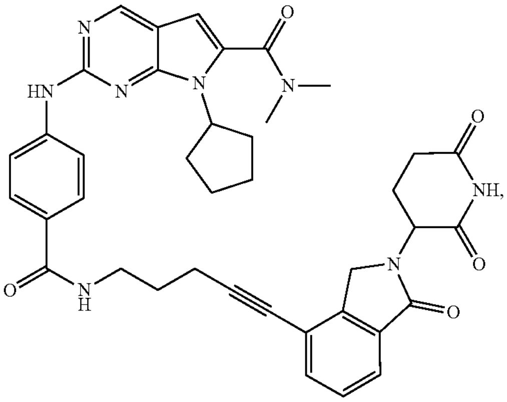

-continued
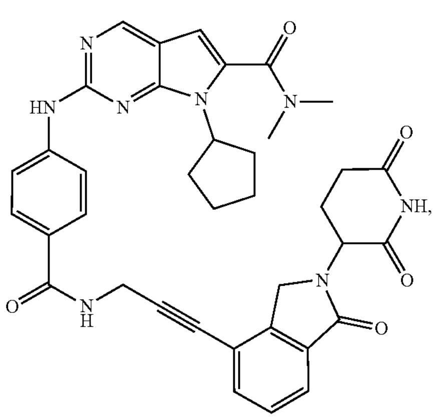
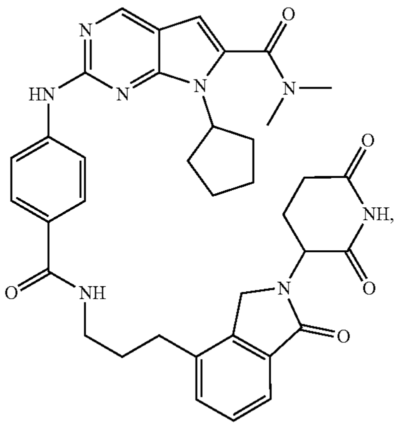
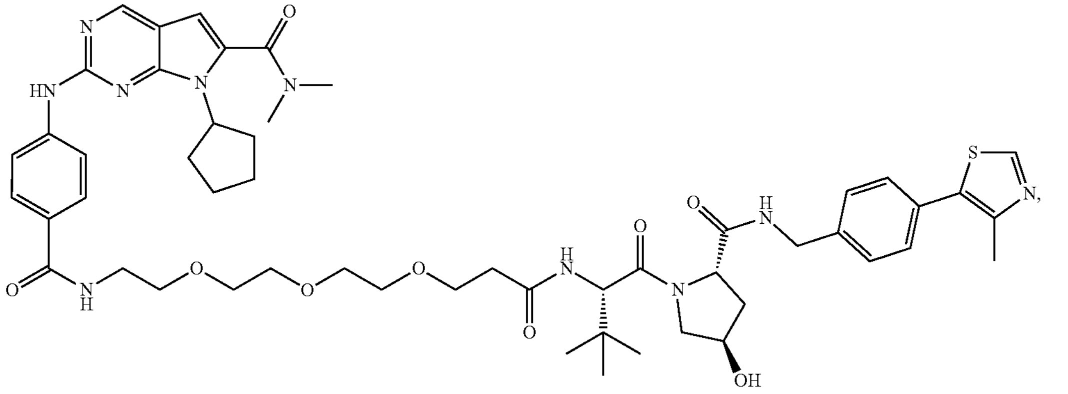
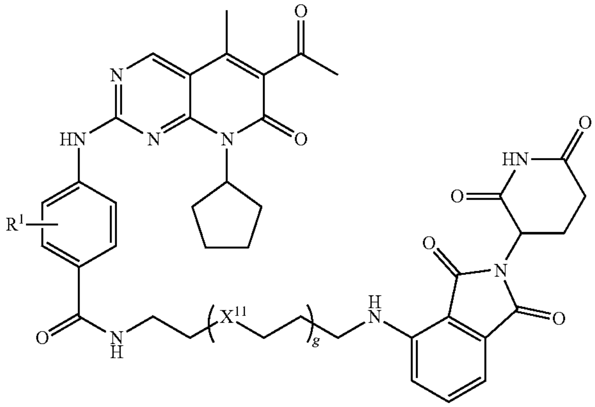
,
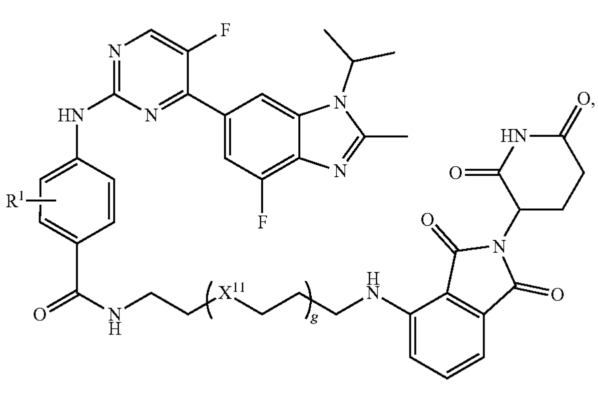
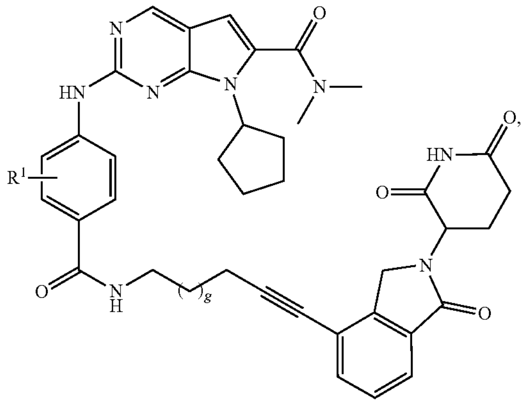

-continued
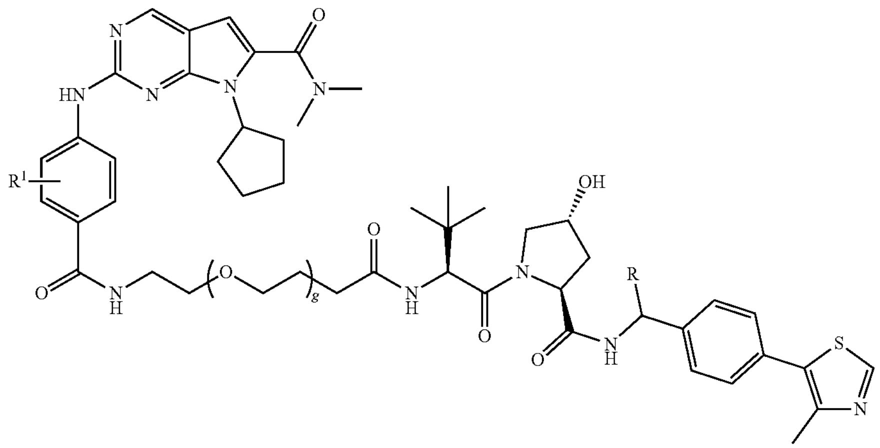
,
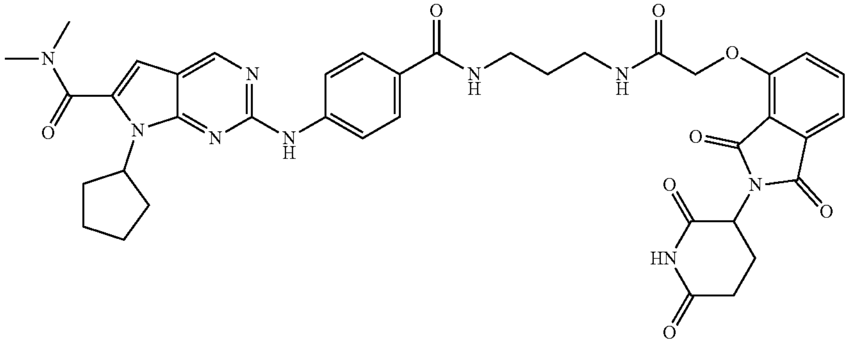
,
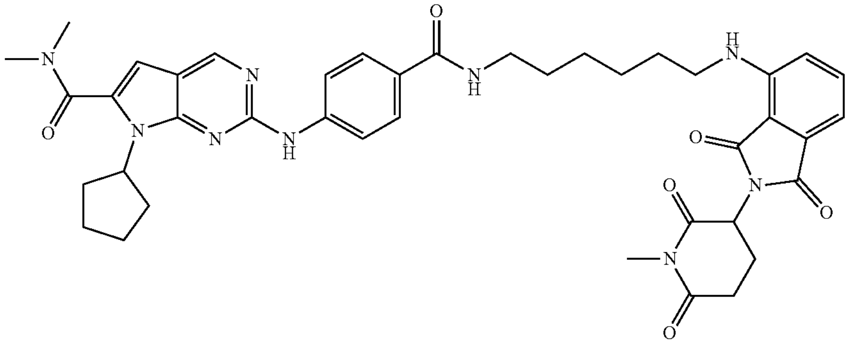
,
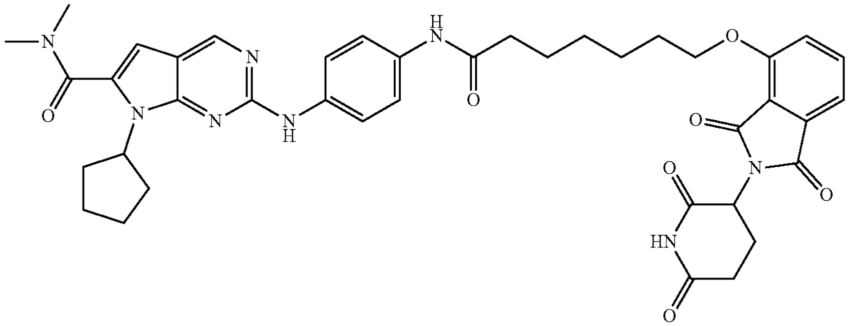
,

-continued
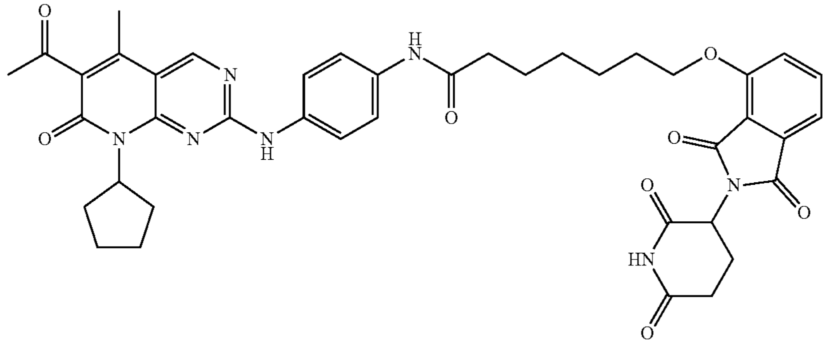
,
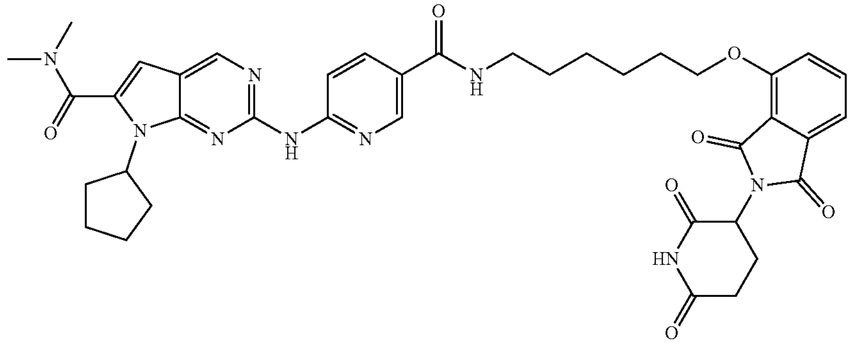
,
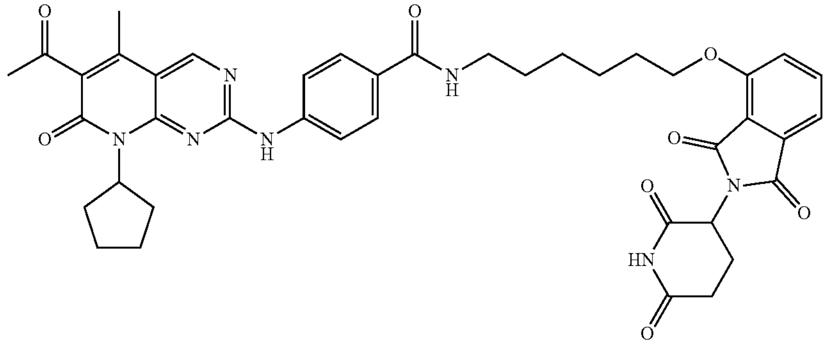
,
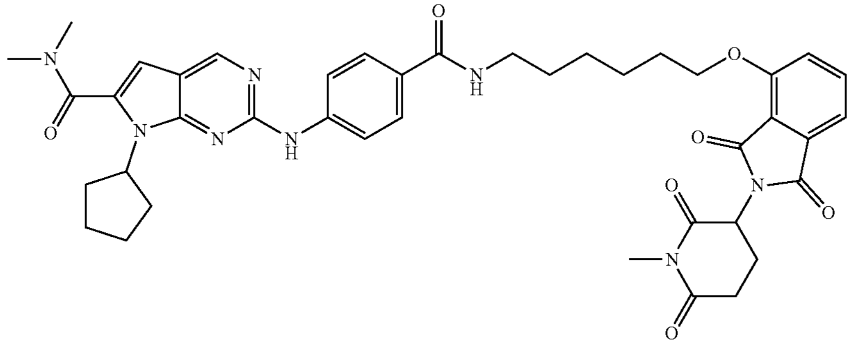
,
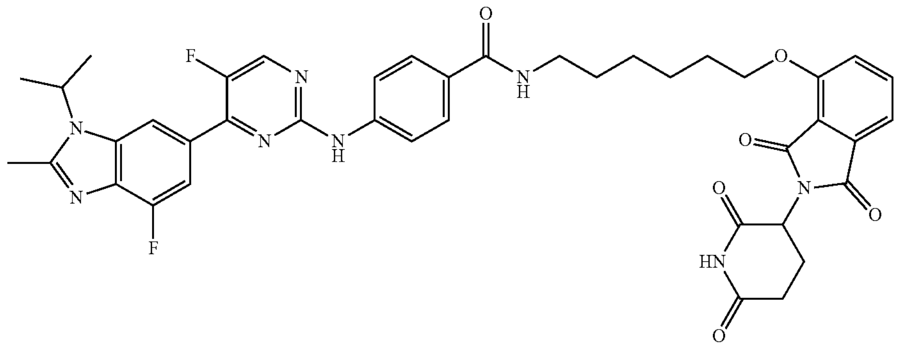
, -continued

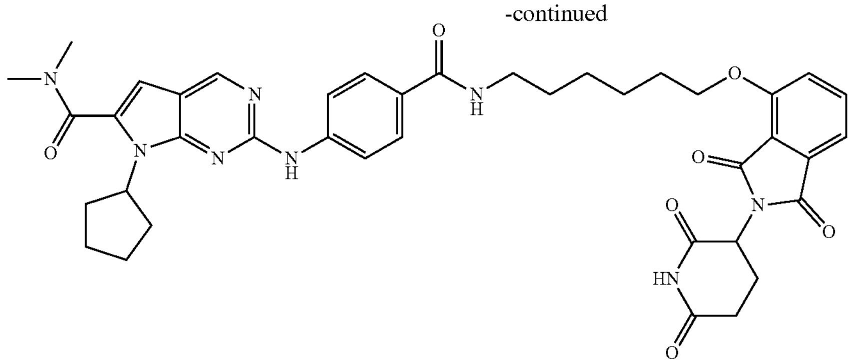

, and

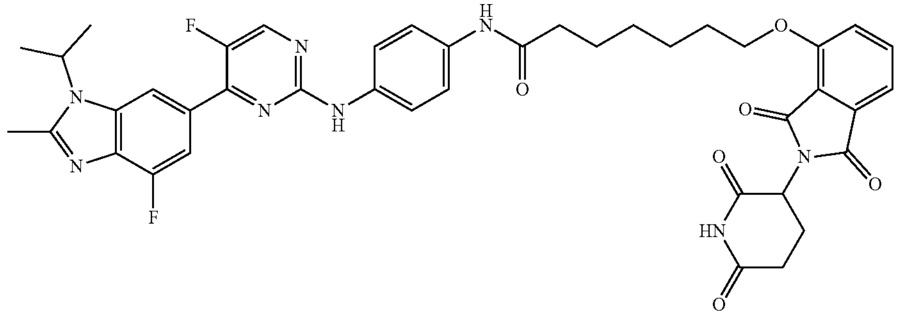

or a pharmaceutically acceptable salt, polymorph, prodrug, solvate or clathrate thereof.

Methods of Treatment

The disclosure relates to methods of treating disorders or diseases associated with N-Myc, comprising the step of administering to a subject suffering therefrom, a therapeutically effective amount of any one of the aforementioned compounds.

The disclosure relates to methods of treating disorders or diseases associated with Aurora kinase A, comprising the step of administering to a subject suffering therefrom, a therapeutically effective amount of any one of the aforementioned compounds.

The disclosure relates to methods of treating disorders or diseases associated with CDK4/6, comprising the step of administering to a subject suffering therefrom, a therapeutically effective amount of any one of the aforementioned compounds.

The disclosure relates to methods of treating disorders or diseases associated with Cyclin Ds, comprising the step of administering to a subject suffering therefrom, a therapeutically effective amount of any one of the aforementioned compounds.

Accordingly, the disclosure relates to method of treating cancer. The cancer can be neuroblastoma, medulloblastoma, small-cell lung cancer, and neuroendocrine prostate cancer. The cancer can be leukemia, lympoma, ovarian cancer, breast cancer, brain cancer, non-small cell lung cancer or soft-tissue sarcoma.

Pharmaceutical Compositions, Routes of Administration, and Dosing

The disclosure also provides a pharmaceutical composition comprising a compound of any of the preceding formulae and a pharmaceutically acceptable carrier. The disclosure also provides a pharmaceutical composition comprising a therapeutically effective amount of a compound of one of Formulae (I)-(V), and a pharmaceutically acceptable carrier.

The disclosure also contemplates pharmaceutical compositions comprising one or more compounds of the various embodiments of the disclosure and one or more pharmaceutically acceptable excipients, A "pharmaceutical composition" refers to a chemical or biological composition suitable for administration to a subject (e.g., mammal). Such compositions can be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" is a carrier, sometimes a liquid, in which an active therapeutic agent is formulated. The excipient generally does not provide any pharmacological activity to the formulation, though it can provide chemical and/or biological stability, and release characteristics. Examples of suitable formulations can be found, for example, in Remington, The Science And Practice of Pharmacy, 20th Edition. (Gennaro, A. R., Chief Editor), Philadelphia College of Pharmacy and Science, 2000, which is incorporated by reference in its entirety.

As used herein "pharmaceutically acceptable carrier" or "excipient" includes, but is not limited to, any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art, Except insofar as any conventional media or agent is incompatible with the active compound, use thereof in the pharmaceutical compositions of the disclosure is contemplated. Supplementary active compounds can also be incorporated into the compositions.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the disclosure can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The pharmaceutical compositions of the disclosure can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons at ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereat.

Other compounds which can be included by admixture are, for example, medically inert ingredients (e.g., sod and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the disclosure can vary according to factors such as the disease state, age, gender, weight, patient history, risk factors, predisposition to disease, administration route, pre-existing treatment regime (e.g., possible interactions with other medications), and weight of the subject. Dosage regimens can be adjusted to provide the optimum therapeutic response. For example, a singe bolus can be administered, several divided doses can be administered over time, or the dose can be proportionally reduced or increased as indicated by the exigencies of therapeutic situation.

A "dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of sensitivity in subjects. In therapeutic use for treatment of conditions in mammals (e.g., humans) for which the compounds of the disclosure or an appropriate pharmaceutical composition thereof are effective, the compounds of the disclosure can be administered in an effective amount. The dosages as suitable for this disclosure can be a composition, a pharmaceutical composition or any other compositions described herein.

For each of the recited embodiments, the dosage is typically administered once, twice, or thrice a day, although more frequent dosing intervals are possible. The dosage can be administered every day, every 2 days, every 3 days, every 4 days, every 5 days, every 6 days, and/or every 7 days (once a week). In one embodiment, the dosage can be administered daily for up to and including 30 days, preferably between 7-10 days. In another embodiment, the dosage can be administered twice a day for 10 days. If the patient requires treatment for a chronic disease or condition, the dosage can be administered for as long as signs and/or symptoms persist. The patient can require "maintenance treatment" where the patient is receiving dosages every day for months, years, or the remainder of their lives. In addition, the composition of this disclosure can be to effect prophylaxis of recurring symptoms. For example, the dosage can be administered once or twice a day to prevent the onset of symptoms in patients at risk, especially for asymptomatic patients.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to, for example, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

As stated in the disclosure, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the disclosure being administered, the size of the subject, or the severity of the disease or condition. One of ordinary skill in the art can empirically determine the effective amount of a particular compound of the disclosure and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of a compound are, for human subjects, from about 0.01 milligrams/kg per day to 1000 milligrams/kg per day. Oral doses in the range of 0.5 to 50 milligrams/kg, in one or more administrations per day, can yield therapeutic results. Dosage may be adjusted appropriately to achieve desired drug levels, local or systemic, depending upon the mode of administration. For example, intravenous administration may vary from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of the compound.

For any compound described herein the therapeutically effective amount can be initially determined from animal models. A therapeutically effective dose can also be determined from human data for compounds which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

For clinical use, any compound of the disclosure can be administered in an amount equal or equivalent to 0.2-2000 milligram (mg) of compound per kilogram (kg) of body weight of the subject per day. The compounds of the disclosure can be administered in a dose equal or equivalent to 2-2000 mg of compound per kg body weight of the subject per day. The compounds of the disclosure can be administered in a dose equal or equivalent to 20-2000 mg of compound per kg body weight of the subject per day. The compounds of the disclosure can be administered in a dose equal or equivalent to 50-2000 mg of compound per kg body weight of the subject per day. The compounds of the disclosure can be administered in a dose equal or equivalent to 100-2000 mg of compound per kg body weight of the subject per day. The compounds of the disclosure can be administered in a dose equal or equivalent to 200-2000 mg of compound per kg body weight of the subject per day. Where a precursor or prodrug of the compounds of the disclosure is to be administered rather than the compound itself, it is administered in an amount that is equivalent to, i.e., sufficient to deliver, the above-stated amounts of the compounds of the invention.

The formulations of the compounds of the disclosure can be administered to human subjects in therapeutically effective amounts, Typical dose ranges are from about 0.01 microgram/kg to about 2 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments may be used to optimize the dose and dosing frequency for any particular compound.

The compounds of the disclosure can be administered at a concentration in the range from about 0.001 microgram/kg to greater than about 500 mg/kg. For example, the concentration may be 0.001 microgram/kg, 0.01 microgram/kg, 0.05 microgram/kg, 0.1 microgram/kg, 0.5 microgram/kg, 1.0 microgram/kg, 10.0 microgram/kg, 50.0 microgram/kg, 100.0 microgram/kg, 500 microgram/kg, 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed by the present invention.

The compounds of the disclosure can be administered at a dosage in the range from about 0.2 milligram/kg/day to greater than about 100 mg/kg/day. For example, the dosage may be 0.2 mg/kg/day to 100 mg/kg/day, 0.2 mg/kg/day to 50 mg/kg/day, 0.2 mg/kg/day to 25 mg/kg/day, 0.2 mg/kg/day to 10 mg/kg/day, 0.2 mg/kg/day to 7.5 mg/kg/day, 0.2 mg/kg/day to 5 mg/kg/day, 0.25 mg/kg/day to 100 mg/kg/day, 0.25 mg/kg/day to 50 mg/kg/day, 0.25 mg/kg/day to 25 mg/kg/day, 0.25 mg/kg/day to 10 mg/kg/day, 0.25 mg/kg/day to 7.5 mg/kg/day, 0.25 mg/kg/day to 5 mg/kg/day, 0.5 mg/kg/day to 50 mg/kg/day, 0.5 mg/kg/day to 25 mg/kg/day, 0.5 mg/kg/day to 20 mg/kg/day, 0.5 mg/kg/day to 15 mg/kg/day, 0.5 mg/kg/day to 10 mg/kg/day, 0.5 mg/kg/day to 7.5 mg/kg/day, 0.5 mg/kg/day to 5 mg/kg/day, 0.75 mg/kg/day to 50 mg/kg/day, 0.75 mg/kg/day to 25 mg/kg/day, 0.75 mg/kg/day to 20 mg/kg/day, 0.75 mg/kg/day to 15 mg/kg/day, 0.75 mg/kg/day to 10 mg/kg/day, 0.75 mg/kg/day to 7.5 mg/kg/day, 0.75 mg/kg/day to 5 mg/kg/day, 1.0 mg/kg/day to 50 mg/kg/day, 1.0 mg/kg/day to 25 mg/kg/day, 1.0 mg/kg/day to 20 mg/kg/day, 1.0 mg/kg/day to 15 mg/kg/day, 1.0 mg/kg/day to 10 mg/kg/day, 1.0 mg/kg/day to 7.5 mg/kg/day, 1.0 mg/kg/day to 5 mg/kg/day, 2 mg/kg/day to 50 mg/kg/day, 2 mg/kg/day to 25 mg/kg/day, 2 mg/kg/day to 20 mg/kg/day, 2 mg/kg/day to 15 mg/kg/day, 2 mg/kg/day to 10 mg/kg/day, 2 mg/kg/day to 7.5 mg/kg/day, or 2 mg/kg/day to 5 mg/kg/day.

The compounds of the disclosure can be administered at a dosage in the range from about 0.25 milligram/kg/day to about 25 mg/kg/day. For example, the dosage may be 0.25 mg/kg/day, 0.5 mg/kg/day, 0.75 mg/kg/day, 1.0 mg/kg/day, 1.25 mg/kg/day, 1.5 mg/kg/day, 1.75 mg/kg/day, 2.0 mg/kg/day, 2.25 mg/kg/day, 2.5 mg/kg/day, 2.75 mg/kg/day, 3.0 mg/kg/day, 3.25 mg/kg/day, 3.5 mg/ka/day, 3.75 mg/kg/day, 4.0 mg/kg/day, 4.25 mg/kg/day, 4.5 mg/kg/day, 4.75 mg/kg/day, 5 mg/kg/day, 5.5 mg/kg/day, 6.0 mg/kg/day, 6.5 mg/kg/day, 7.0 mg/kg/day, 7.5 mg/kg/day, 8.0 mg/kg/day, 8.5 mg/kg/day, 9.0 mg/kg/day, 9.5 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, 24 mg/kg/day, 25 mg/kg/day, 26 mg/kg/day, 27 mg/kg/day, 28 mg/kg/day, 29 mg/kg/day, 30 mg/kg/day, 31 mg/kg/day, 32 mg/kg/day, 33 mg/kg/day, 34 mg/kg/day, 35 mg/kg/day, 36 mg/kg/day, 37 mg/kg/day, 38 mg/kg/day, 39 mg/kg/day, 40 mg/kg/day, 41 mg/kg/day, 42 mg/kg/day, 43 mg/kg/day, 44 mg/kg/day, 45 mg/kg/day, 46 mg/kg/day, 47 mg/kg/day, 48 mg/kg/day, 49 mg/kg/day, or 50 mg/kg/day.

In various embodiments, the compound or precursor thereof is administered in concentrations that range from 0.01 micromolar to greater than or equal to 500 micromolar. For example, the dose may be 0.01 micromolar, 0.02 micromolar, 0.05 micromolar, 0.1 micromolar, 0.15 micromolar, 0.2 micromolar, 0.5 micromolar, 0.7 micromolar, 1.0 micromolar, 3.0 micromolar, 5.0 micromolar, 7.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 60.0 micromolar, 70.0 micromolar, 80.0 micromolar, 90.0 micromolar, 100.0 micromolar, 150.0 micromolar, 200.0 micromolar, 250.0 micromolar, 300.0 micromolar, 350.0 micromolar, 400.0 micromolar, 450.0 micromolar, to greater than about 500.0 micromolar or any incremental value thereof. It is to be understood that all values and ranges between these values and ranges are meant to be encompassed by the present invention.

In various embodiments, the compound or precursor thereof is administered at concentrations that range from 0.10 microgram/mL to 500.0 microgram/mL. For example, the concentration may be 0.10 microgram/mL, 0.50 microgram/mL, 1 microgram/mL, 2.0 microgram/mL, 5.0 microgram/mL, 10.0 microgram/mL, 20 microgram/mL, 25 microgram/mL, 30 microgram/mL, 35 microgram/mL, 40 microgram/mL, 45 microgram/mL, 50 microgram/mL, 60.0 microgram/mL, 70.0 microgram/mL, 80.0 microgram/mL, 90.0 microgram/mL, 100.0 microgram/mL, 150.0 microgram/mL, 200.0 microgram/mL, 250.0 g/mL, 250.0 micro gram/mL, 300.0 microgram/mL, 350.0 microgram/mL, 400.0 microgram/mL, 450.0 microgram/mL, to greater than about 500.0 microgram/mL or any incremental value thereof. It is to be understood that all values and ranges between these values and ranges are meant to be encompassed by the present invention.

The disclosure also provides a method for modulating N-Myc comprising administering a therapeutically effective amount of any of the preceding compounds, e.g., a compound of any of Formula (I)-(V), or a pharmaceutical composition comprising said compound, to a subject in need thereof.

The disclosure also provides a method for treating cancer and other proliferative disorders, including, but not limited to breast cancer, cervical cancer, colon and rectal cancer, leukemia, lung cancer (e.g., non-small cell lung cancer), melanoma, multiple myeloma, non-Hodgkin's lymphoma, ovarian cancer, pancreatic cancer, prostate cancer, gastric cancer, leukemias (e.g., myeloid, lymphocytic, myelocytic and lymphoblastic leukemias), malignant melanomas, and T-cell lymphoma) or neuroblastoma comprising administering a therapeutically effective amount of any of the preceding compounds, e.g., a compound of any of Formula (I)-(V), or a pharmaceutical composition comprising said compound, to a subject in need thereof.

The term "therapeutically effective amount" as used herein, refers to that amount of one or more compounds of the various examples of the disclosure that elicits a biological or medicinal response in a tissue system, animal or human, that is being sought by a researcher, veterinarian, medical doctor or other clinician, which includes alleviation of the symptoms of the disease or disorder being treated. In some examples, the therapeutically effective amount is that which can treat or alleviate the disease or symptoms of the disease at a reasonable benefit/risk ratio applicable to any medical treatment. However, it is to be understood that the total daily usage of the compounds and compositions described herein can be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

The term "alkyl" as used herein refers to substituted or unsubstituted straight chain, branched and cyclic, saturated mono- or bi-valent groups having from 1 to 20 carbon atoms, 10 to 20 carbon atoms, 12 to 18 carbon atoms, 6 to about 10 carbon atoms, 1 to 10 carbons atoms, 1 to 8 carbon atoms, 2 to 8 carbon atoms, 3 to 8 carbon atoms, 4 to 8 carbon atoms, 5 to 8 carbon atoms, 1 to 6 carbon atoms, 2 to 6 carbon atoms, 3 to 6 carbon atoms, or 1 to 3 carbon atoms. Examples of straight chain mono-valent ($C_1$-$C_{20}$)-alkyl groups include those with from 1 to 8 carbon atoms such as methyl (i.e., $CH_3$), ethyl, n-propyl, n-butyl, n-pentyl, n-hexyl, n-heptyl, n-octyl groups. Examples of branched mono-valent ($C_1$-$C_{20}$-alkyl croups include isopropyl, iso-butyl, sec-butyl, t-butyl, neopentyl, and isopentyl. Examples of straight chain bi-valent ($C_1$-$C_{20}$)alkyl groups include those with from 1 to 6 carbon atoms such as $—CH_2—$, $—CH_2CH_2—$, $—CH_2CH_2CH_2—$, $—CH_2CH_2CH_2CH_2—$, and $—CH_2CH_2CH_2CH_2CH_2—$. Examples of branched bi-valent alkyl groups include $—CH(CH_3)CH_2—$ and $—CH_2CH(CH_3)CH_2—$. Examples of cyclic alkyl groups include cyclopropyl, cyclooctyl, cyclopently, cyclohexyl, cyclooctyl, bicyclo[1.1.1]pentyl, bicyclo[2.1.1]hexyl, and bicyclo[2.2.1]heptyl. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. In some embodiments, alkyl includes a combination of substituted and unsubstituted alkyl. As an example, alkyl, and also ($C_1$)alkyl, includes methyl and substituted methyl. As a particular example, ($C_1$)alkyl includes benzyl. As a further example, alkyl can include methyl and substituted ($C_2$-$C_8$)alkyl. Alkyl can also include substituted methyl and unsubstituted ($C_2$-$C_8$)alkyl. In some embodiments, alkyl can be methyl and $C_2$-$C_8$ linear alkyl. In some embodiments, alkyl can be methyl and $C_2$-$C_8$ branched alkyl. The term methyl is understood to be $—CH_3$, which is not substituted. The term methylene is understood to be $—CH_2—$, which is not substituted. For comparison, the term ($C_1$)alkyl is understood to be a substituted or an unsubstituted $—CH_3$ or a substituted or an unsubstituted $—CH_2—$. Representative substituted alkyl groups can be substituted one or more times with any of the groups listed herein, for example, cycloalkyl, heterocyclyl, aryl, amino, haloalkyl, hydroxy, cyano, carboxy, nitro, thio, alkoxy, and halogen groups. As further example, representative substituted alkyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkyl groups can be substituted from a set of groups including amino, hydroxy, cyano, carboxy, nitro, thio and alkoxy, but not including halogen groups. Thus, in some embodiments alkyl can be substituted with a non-halogen group. For example, representative substituted alkyl groups can be substituted with a fluoro group, substituted with a bromo group, substituted with a halogen other than bromo, or substituted with a halogen other than fluoro. In some embodiments, representative substituted alkyl groups can be substituted with one, two, three or more fluoro groups or they can be substituted with one, two, three or more non-fluoro groups. For example, alkyl can be trifluoromethyl, difluoromethyl, or fluoromethyl, or alkyl can be substituted alkyl other than trifluoromethyl, difluoromethyl or fluoromethyl. Alkyl can be haloalkyl or alkyl can be substituted alkyl other than haloalkyl.

The term "alkenyl" as used herein refers to substituted or unsubstituted straight chain, branched and cyclic, saturated mono- or bi-valent groups having at least one carbon-carbon double bond and from 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. The double bonds can be be trans or cis orientation. The double bonds can be terminal or internal. The alkenyl group can be attached via the portion of the alkenyl group containing the double bond, e.g., vinyl, propen-1-yl and buten-1-yl, or the alkenyl group can be attached via a portion of the alkenyl group that does not contain the double bond, e.g., penten-4-yl. Examples of mono-valent ($C_2$-$C_{20}$)-alkenyl groups include those with from 1 to 8 carbon atoms such as vinyl, propenyl, propen-1-yl, proper-2-yl, butenyl, buten-1-yl, buten-2-yl, sec-buten-1-yl, sec-buten-3-yl, pentenyl, hexenyl, heptenyl and octenyl groups. Examples of branched mono-valent ($C_2$-$C_{20}$)-alkenyl groups include isopropenyl, iso-butenyl, sec-butenyl, t-butenyl, neopentenyl, and isopentenyl. Examples of straight chain bi-valent ($C_2$-$C_{20}$)alkenyl groups include those with from 2 to 6 carbon atoms such as $—CHCH—$, $—CHCHCH_2—$, $—CHCHCH_2CH_2—$, and $—CHCHCH_2CH_2CH_7—$. Examples of branched bi-valent alkyl groups include $—C(CH_3)CH—$ and $—CHC(CH_3)CH_2—$. Examples of cyclic alkenyl groups include cyclopentenyl, cyclohexenyl and cyclooctenyl. It is envisaged that alkenyl can also include masked alkenyl groups, precursors of alkenyl croups or other related groups. As such, where alkenyl groups are described it, compounds are also envisaged where a carbon-carbon double bond of an alkenyl is replaced by an epoxide or aziridine ring. Substituted alkenyl also includes alkenyl groups which are substantially tautomeric with a nonalkenyl group. For example, substituted alkenyl can be 2-aminoalkenyl, 2-alkylaminoalkenyl, 2-hydroxyalkenyl, 2-hydroxyvinyl, 2-hydroxypropenyl, but substituted alkenyl is also understood to include the group of substituted alkenyl groups other than alkenyl which are tautomeric with non-alkenyl containing groups. In some embodiments, alkenyl can be understood to include a combination of substituted and unsubstituted alkenyl. For example, alkenyl can be vinyl and substituted vinyl. For example, alkenyl can be vinyl and substituted ($C_3$-$C_8$) alkenyl. Alkenyl can also include substituted vinyl and unsubstituted ($C_3$-$C_8$)alkenyl. Representative substituted alkenyl groups can be substituted one or more times with any of the groups listed herein, for example, monoalkylamino, dialkylamino, cyano, acetyl, amido, carboxy, nitro, alkylthio, alkoxy, and halogen groups. As further example, representative substituted alkenyl groups can be substituted one or more fluoro, chloro, bromo, iodo, amino, amido, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. In some embodiments, representative substituted alkenyl groups can be substituted from a set of groups including monoalkylamino, dialkylamino, cyano, acetyl, amido, carboxy, nitro, alkylthio and alkoxy, but not including halogen groups. Thus, in some embodiments alkenyl can be substituted with a non-halogen group. In some embodiments, representative substituted alkenyl groups can be substituted with a fluoro group, substituted with a bromo group, substituted with a halogen other than bromo, or substituted with a halogen other than fluoro. For example, alkenyl can be 1-fluorovinyl, 2-fluorovinyl, 1,2-difluorovinyl, 1,2,2-trifluorovinyl, 2,2-difluorovinyl, trifluoropropen-2-yl, 3,3,3-trifluoropropenyl, 1-fluoropropenyl, 1-chlorovinyl, 2-chlorovinyl, 1,2-dichlorovinyl, 1,2,2-trichlorovinyl or 2,2-dichlorovinyl. In some embodiments, representative substituted alkenyl groups can be substituted with one, two, three or more fluoro groups or they can be substituted with one, two, three or more non-fluoro groups.

The term "alkynyl" as used herein, refers to substituted or unsubstituted straight and branched chain alkyl groups, except that at least one triple bond exists between two carbon atoms. Thus, alkynyl groups have from 2 to 50 carbon atoms, 2 to 20 carbon atoms, 10 to 20 carbon atoms, 12 to 18 carbon atoms, 6 to about 10 carbon atoms, 2 to 10 carbons atoms, 2 to 8 carbon atoms, 3 to 8 carbon atoms, 4 to 8 carbon atoms, 5 to 8 carbon atoms, 2 to 6 carbon atoms, 3 to 6 carbon atoms, 4 to 6 carbon atoms, 2 to 4 carbon atoms, or 2 to 3 carbon atoms. Examples include, but are not limited to ethynyl, propynyl, propyn-1-yl, propyn-2-yl, butynyl, Butyn-1-yl, butyn-2-yl, Butyn-3-yl, butyn-4-yl, pentynyl, pentyn-1-yl, hexynyl, Examples include, but are not limited to $-C\equiv CH$, $-C\equiv C(CH_3)$, $-C\equiv C(CH_2CH_3)$, $-CH_2C\equiv CH$, $-CH_2C\equiv C(CH_3)$, and $-CH_2C\equiv C(CH_2CH_3)$ among others.

The term "aryl" as used herein refers to substituted or unsubstituted univalent groups that are derived by removing a hydrogen atom from an arene, which is a cyclic aromatic hydrocarbon, having from 6 to 20 carbon atoms, 10 to 20 carbon atoms, 12 to 20 carbon atoms, 6 to about 10 carbon atoms or 6 to 8 carbon atoms. Examples of $(C_6-C_{20})$aryl groups include phenyl, napthalenyl, azulenyl, biphenylyl, indacenyl, fluorenyl, phenanthrenyl, triphenylenyl, pyrenyl, naphthacenyl, chrysenyl, anthracenyl groups. Examples include substituted phenyl, substituted napthalenyl, substituted azulenyl, substituted biphenylyl, substituted indacenyl, substituted fluorenyl, substituted phenanthrenyl, substituted triphenylenyl, substituted pyrenyl, substituted naphthacenyl, substituted chrysenyl, and substituted anthracenyl groups. Examples also include unsubstituted phenyl, unsubstituted napthalenyl, unsubstituted azulenyl, unsubstituted biphenylyl, unsubstituted indacenyl, unsubstituted fluorenyl, unsubstituted phenanthrenyl, unsubstituted triphenylenyl, unsubstituted pyrenyl, unsubstituted naphthacenyl, unsubstituted chrysenyl, and unsubstituted anthracenyl groups. Aryl includes phenyl groups and also non-phenyl aryl groups. From these examples, it is clear that the term $(C_6-C_{20})$aryl encompasses mono- and polycyclic $(C_6-C_{20})$aryl groups, including fused and non-fused polycyclic $(C_6-C_{20})$aryl groups.

The term "heterocyclyl" as used herein refers to substituted aromatic, unsubstituted aromatic, substituted non-aromatic, and unsubstituted non-aromatic rings containing 3 or more atoms in the ring, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms $(C_3-C_8)$, 3 to 6 carbon atoms $(C_3-C_6)$ or 6 to 8 carbon atoms $(C_6-C_8)$. A heterocyclyl group designated as a $C_2$-heterocyclyl can be a 5-membered ring with two carbon atoms and three heteroatoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to piperidynyl, piperazinyl, morpholinyl, furanyl, pyrrolidinyl, pyridinyl, pyrazinyl, pyrimidinyl, triazinyl, thiophenyl, tetrahydrofuranyl, pyrrolyl, oxazolyl, imidazolyl, triazyolyl, tetrazolyl, benzoxazolinyl, and benzimidazolinyl groups. For example, heterocyclyl groups include, without limitation:

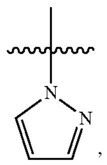, 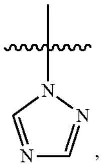, 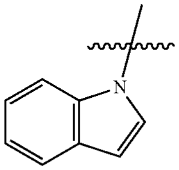,

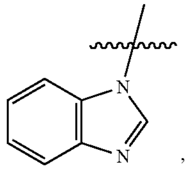, 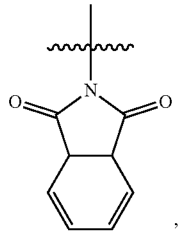, 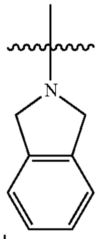,

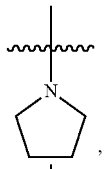, 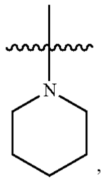, 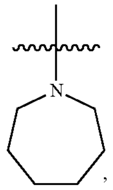, 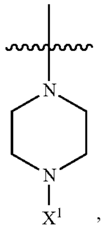,

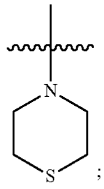; and 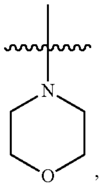, wherein $X^1$ represents H, $(C_1-C_{20})$alkyl, $(C_6-C_{20})$aryl or an amine protecting group (e.g., a t-butyloxycarbonyl group) and wherein the heterocyclyl group can be substituted or unsubstituted. A nitrogen-containing heterocyclyl group is a heterocyclyl group containing a nitrogen atom as an atom in the ring. In some embodiments, the heterocyclyl is other than thiophene or substituted thiophene. In some embodiments, the heterocyclyl is other than furan or substituted furan.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. Thus, alkyoxy also includes an oxygen atom connected to an alkyenyl group and oxygen atom connected to an alkynyl group. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term “aryloxy” as used herein refers to an oxygen atom connected to an aryl group as are defined herein.

The term “aralkyl” and “arylalkyl” as used herein refers to alkyl groups as defined herein in which a hydrogen or carbon bond of an alkyl group is replaced with a bond to an aryl group as defined herein. Representative aralkyl groups include benzyl, biphenylmethyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The terms “halo,” “halogen,” or “halide” group, as used herein, by themselves or as part of another substituent, mean, unless otherwise stated, a fluorine, chlorine, bromine, or iodine atom.

The term “amino” as used herein refers to a substituent of the form $—NH_2$, —NHR, $—NR_2$, $—NR_3^+$, wherein each R is independently selected, and protonated forms of each, except for $—NR_3^+$, which cannot be protonated. Accordingly, any compound substituted with an amino group can be viewed as an amine. An “amino group” within the meaning herein can be a primary, secondary, tertiary, or quaternary amino group. An “alkylamino” group includes a monoalkylamino, dialkylamino, and trialkylamino group.

The term “acyl” as used herein refers to a group containing a carbonyl moiety wherein the group is bonded via the carbonyl carbon atom. The carbonyl carbon atom is also bonded to another carbon atom, which can be part of a substituted or unsubstituted alkyl, alkenyl, alkynyl, aryl, cycloalkyl, heterocyclyl, group or the like.

The term “formyl” as used herein refers to a group containing a carbonyl moiety wherein the group is bonded via the carbonyl carbon atom. The carbonyl carbon atom is also bonded to a hydrogen atom.

The term “alkoxycarbonyl” as used herein refers to a group containing a carbonyl moiety wherein the group is bonded via the carbonyl carbon atom. The carbonyl carbon atom is also bonded to an oxygen atom which is further bonded to an alkyl group. Alkoxycarbonyl also includes the group where a carbonyl carbon atom is also bonded to an oxygen atom which is further bonded to an alkyenyl group. Alkoxycarbonyl also includes the group where a carbonyl carbon atom is also bonded to an oxygen atom which is further bonded to an alkynyl group. In a further case, which is included in the definition of alkoxycarbonyl as the term is defined herein, and is also included in the term “aryloxycarbonyl,” the carbonyl carbon atom is bonded to an oxygen atom which is bonded to an aryl group instead of an alkyl group.

The term “arylcarbonyl” as used herein refers to a group containing a carbonyl moiety wherein the group is bonded via the carbonyl carbon atom. The carbonyl carbon atom is also bonded to an aryl group.

The term “alkylamido” as used herein refers to a group containing a carbonyl moiety wherein the group is bonded via the carbonyl carbon atom. The carbonyl carbon atom is also bonded to a nitrogen group which is bonded to one or more alkyl groups. In a further case, which is also an alkylamido as the term is defined herein, the carbonyl carbon atom is bonded to an nitrogen atom which is bonded to one or more aryl group instead of, or in addition to, the one or more alkyl group. In a further case, which is also an alkylamido as the term is defined herein, the carbonyl carbon atom is bonded to an nitrogen atom which is bonded to one or more alkenyl group instead of, or in addition to, the one or more alkyl and or/aryl group. In a further case, which is also an alkylamido as the term is defined herein, the carbonyl carbon atom is bonded to an nitrogen atom which is bonded to one or more alkynyl group instead of, or in addition to, the one or more alkyl, alkenyl and/or aryl group.

The term “carboxy” as used herein refers to a group containing a carbonyl moiety wherein the group is bonded via the carbonyl carbon atom. The carbonyl carbon atom is also bonded to a hydroxy group or oxygen anion so as to result in a carboxylic acid or carboxylate. Carboxy also includes both the protonated form of the carboxylic acid and the salt form. For example, carboxy can be understood as COOH or $CO_2H$.

The term “alkylthio” as used herein refers to a sulfur atom connected to an alkyl, alkenyl, or alkynyl group as defined herein.

The term “arylthio” as used herein refers to a sulfur atom connected to an aryl group as defined herein.

The term “alkylsulfonyl” as used herein refers to a sulfonyl group connected to an alkyl, alkenyl, or alkynyl group as defined herein.

The term “alkylsulfinyl” as used herein refers to a sulfinyl group connected to an alkyl, alkenyl, or alkynyl group as defined herein.

The term “dialkylaminosulfonyl” as used herein refers to a sulfonyl group connected to a nitrogen further connected to two alkyl groups, as defined herein, and which can optionally be linked together to form a ring with the nitrogen. This term also includes the group where the nitrogen is further connected to one or two alkenyl groups in place of the alkyl groups.

The term “dialkylamino” as used herein refers to an amino group connected to two alkyl groups, as defined herein, and which can optionally be linked together to form a ring with the nitrogen. This term also includes the group where the nitrogen is further connected to one or two alkenyl groups in place of the alkyl groups.

The term “dialkylamido” as used herein refers to an amido group connected to two alkyl groups, as defined herein, and which can optionally be linked together to form a ring with the nitrogen. This term also includes the group where the nitrogen is further connected to one or two alkenyl groups in place of the alkyl groups.

The term “substituted” as used herein refers to a group that is substituted with one or more groups including, but not limited to, the following groups: halogen (e.g., F, Cl, Br, and I), R, OR, $OC(O)N(R)_2$, CN, NO, $NO_2$, $ONO_2$, azido, $CF_3$, $OCF_3$, methylenedioxy, ethylenedioxy, ($C_3$-$C_{20}$)heteroaryl, $N(R)_2$, $Si(R)_3$, SR, SOR, $SO_2R$, $SO_2N(R)_2$, $SO_3R$, $P(O)(OR)_2$, $OP(O)(OR)_2$, C(O)R, C(O)C(O)R, $C(O)CH_2C(O)R$, C(S)R, C(O)OR, OC(O)R, $C(O)N(R)_2$, C(O)N(R)OH, $OC(O)N(R)_2$, $C(S)N(R)_2$, $(CH_2)_{0-2}N(R)C(O)R$, $(CH_2)_{0-2}N(R)N(R)_2$, N(R)N(R)C(O)R, N(R)N(R)C(O)OR, $N(R)N(R)CON(R)_2$, $N(R)SO_2R$, $N(R)SO_2N(R)_2$, N(R)C(O)OR, N(R)C(O)R, N(R)C(S)R, $N(R)C(O)N(R)_2$, $N(R)C(S)N(R)_2$, N(COR)COR, N(OR)R, C(=NH)N(R)$_2$, C(O)N(OR)R, or C(=NOR)R wherein R can be hydrogen, ($C_1$-$C_{20}$)alkyl or ($C_6$-$C_{20}$)aryl. Substituted also includes a group that is substituted with one or more groups including, but not limited to, the following groups: fluoro, chloro, bromo, iodo, amino, amino, alkyl, alkoxy, alkylamido, alkenyl, alkynyl, alkoxycarbonyl, acyl, formyl, arylcarbonyl, aryloxycarbonyl, aryloxy, carboxy, haloalkyl, hydroxy, cyano, nitroso, nitro, azido, trifluoromethyl, trifluoromethoxy, thio, alkylthio, arylthiol, alkylsulfonyl, alkylsulfinyl, dialkylaminosulfonyl, sulfonic acid, carboxylic acid, dialkylamino and dialkylamido. Where there are two or more adjacent substituents, the substituents can be linked to form a carbocyclic or heterocyclic ring. Such adjacent groups can have a vicinal or germinal relationship, or they can be adjacent on a ring in, e.g., an ortho-arrangement. Each instance of substituted is understood to be independent. For example, a substituted aryl can be substituted with bromo and a substituted heterocycle on the same compound can be substituted with alkyl. It is envisaged that a substituted group can be substituted with one or more non-fluoro groups. As another example, a substituted group can be substituted with one or more non-cyano groups. As another example, a substituted group can be substituted with one or more groups other than haloalkyl. As yet another example, a substituted group can be substituted with one or more groups other than tert-butyl. As yet a further example, a substituted group can be substituted with one or more groups other than trifluoromethyl. As yet even further examples, a substituted group can be substituted with one or more groups other than nitro, other than methyl, other than methoxymethyl, other than dialkylaminosulfonyl, other than bromo, other than chloro, other than amido, other than halo, other than benzodioxepinyl, other than polycyclic heterocyclyl, other than polycyclic substituted aryl, other than methoxycarbonyl, other than alkoxycarbonyl, other than thiophenyl, or other than nitrophenyl, or groups meeting a combination of such descriptions. Further, substituted is also understood to include fluoro, cyano, haloalkyl, tert-butyl, trifluoromethyl, nitro, methyl, methoxymethyl, dialkylaminosulfonyl, bromo, chloro, amido, halo, benzodioxepinyl, polycyclic heterocyclyl, polycyclic substituted aryl, methoxycarbonyl, alkoxycarbonyl, thiophenyl, and nitrophenyl groups.

In some instances, the compounds described herein (e.g., the compounds al the Formulae (I)-(V) can contain chiral centers. All diastereomers of the compounds described herein are contemplated herein, as well as racemates.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, male, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric (or larger) amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the disclosure. Examples of prodrugs include, but are not limited to, derivatives and metabolites of a compound of the disclosure that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

As used herein, the term "subject" or "patient" refers to any organism to which a composition described herein can be administered, e.g., for experimental, diagnostic, prophylactic and/or therapeutic purposes. Subject refers to a mammal receiving the compositions disclosed herein or subject to disclosed methods. It is understood and herein contemplated that "mammal" includes but is not limited to humans, non-human primates, cows, horses, dogs, cats, mice, rats, rabbits, and guinea pigs.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading can occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

Each embodiment described above is envisaged to be applicable in each combination with other embodiments described herein. For example, embodiments corresponding to Formula (I) are equally envisaged as being applicable to Formulae (III), (IV), and (V). As another example, embodiments corresponding to Formula (III) are equally envisaged as being applicable to Formulae (I), (IV), and (V). As another example, embodiments corresponding to Formula (IV) are equally envisaged as being applicable to Formulae (I), (III), and (V). And as another example, embodiments corresponding to Formula (V) are equally envisaged as being applicable to Formulae (I), (III), and (IV).

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed can be resorted to by those of ordinary skill in the art, and that such modifications and variations are considered to be within the scope of embodiments of the present disclosure

EXAMPLES

The disclosure can be better understood by reference to the following examples which are offered by way of illustration. The disclosure is not limited to the examples given herein.

Figure 3A:
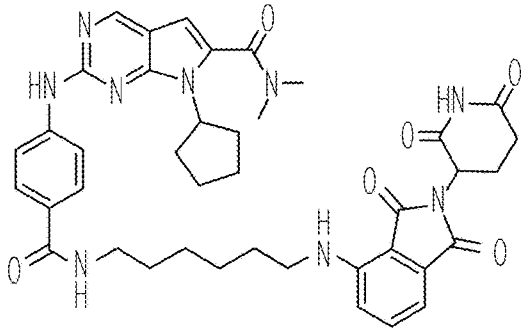
FIG. 3A is the chemical structure of compound 22.
Figure 3B:
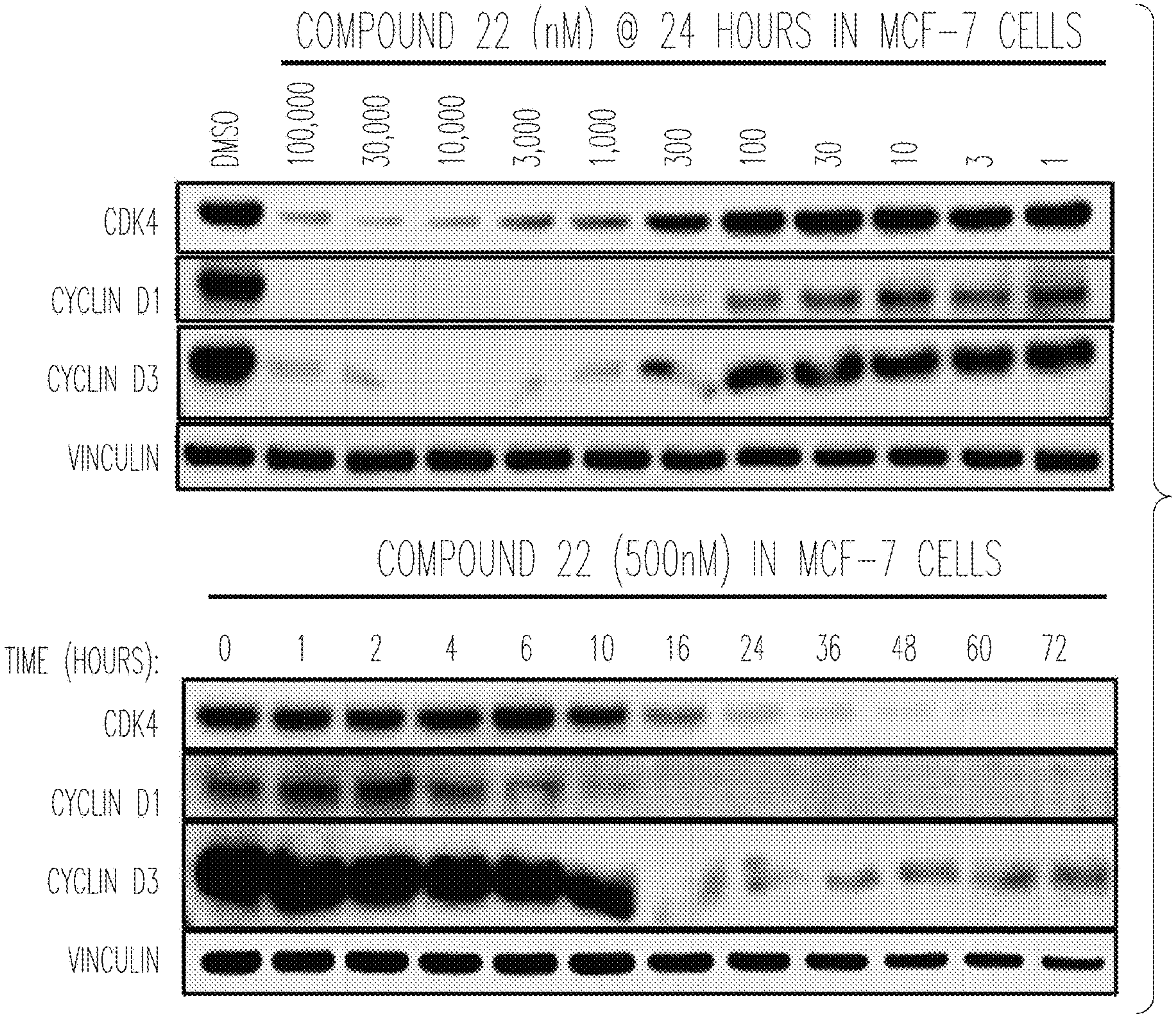
FIG. 3B are Western blot experiments showing dose-dependent and time-dependent degradation of cyclin D-CDK4 complexes in MCF-7 cells.
Figure 3C:
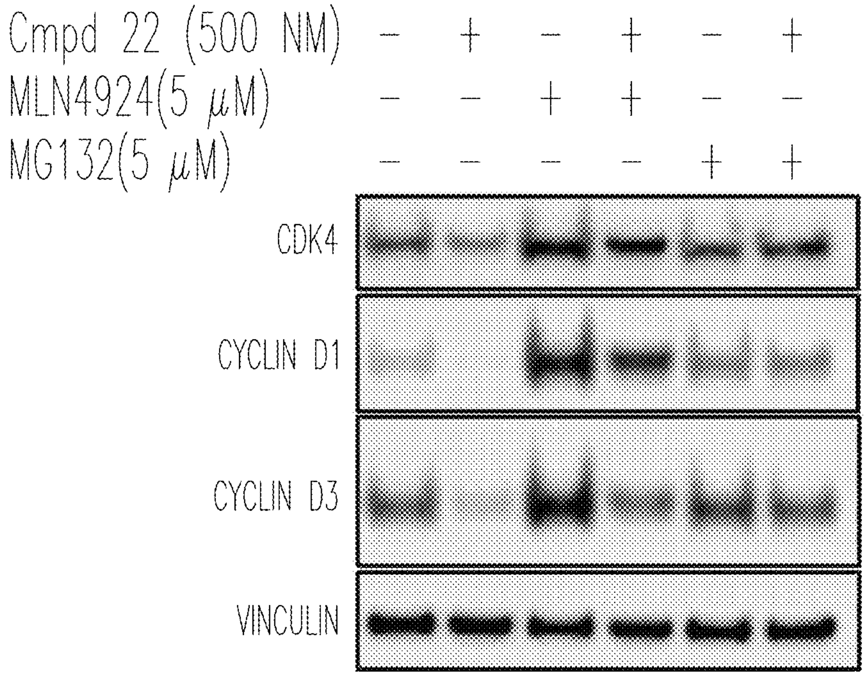
FIG. 3C is a gel showing degradation of cyclin D-CDK4/6 complexes in MCF-7 cells is dependent on the ubiquitin proteasome system (UPS).
Figure 3D:
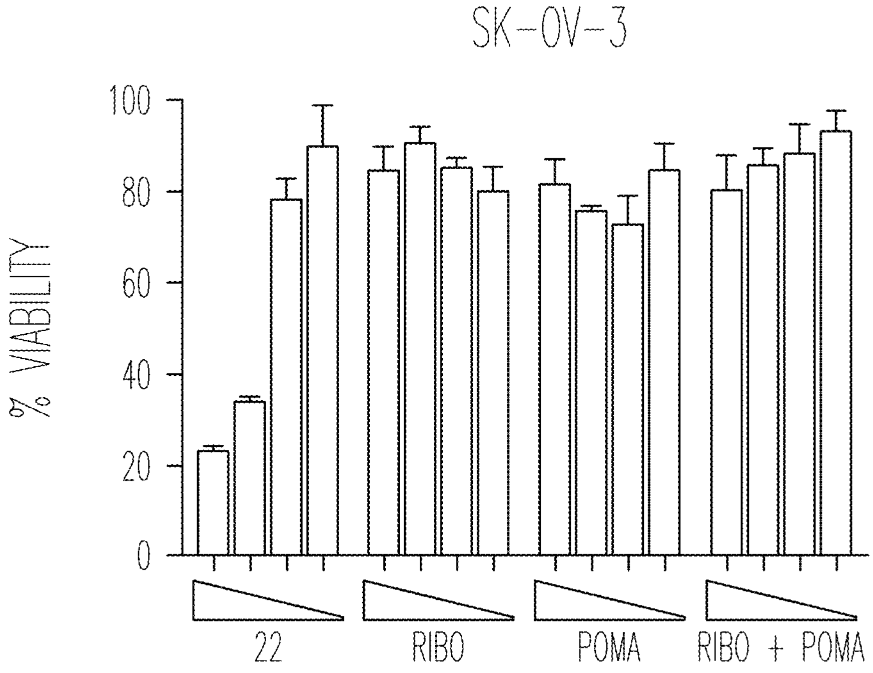
FIG. 3D is a plot showing anti-proliferative activites in ovarian cancer cell line SK-OV-3. Compound concentrations: 10 μM, 1 μM, 100 nM and 10 nM. "Poma" and "Ribo" represent pomalidomide and ribociclib, respectively.

CDK4/6 PROTACs, such as the compounds described herein, were developed by connecting existing CDK4/6 ligands with an E3 ligase ligand via variable linkers. We chose a ribociclib analogue (FIG. 3A) as the CDK4/6 binder and pomalidomide (FIG. 3A) as the cullin-ring E3 ligase cereblon (CRBN) recruiting ligand. 22 (FIG. 3A) was synthesized and evaluations of the compound in MCF-7 breast cancer cells were carried out (note that these cells have very low levels of CDK6, cyclin D2; therefore, only CDK4, cyclin D1 and cyclin D3 were studied). Western blot experiments showed that 22 degrades Cyclin D and CDK4 complexes in a dose-dependent and time-dependent manner. Co-treating cells with 22 and either MLN49, a cullin-ring E3 ligase inhibitor, or proteasome inhibitor MG132 significantly recovered CDK4, cyclin D1 and D3 levels, indicating that the induced degradation is indeed UPS-dependent (FIG. 30).

Figure 4A:
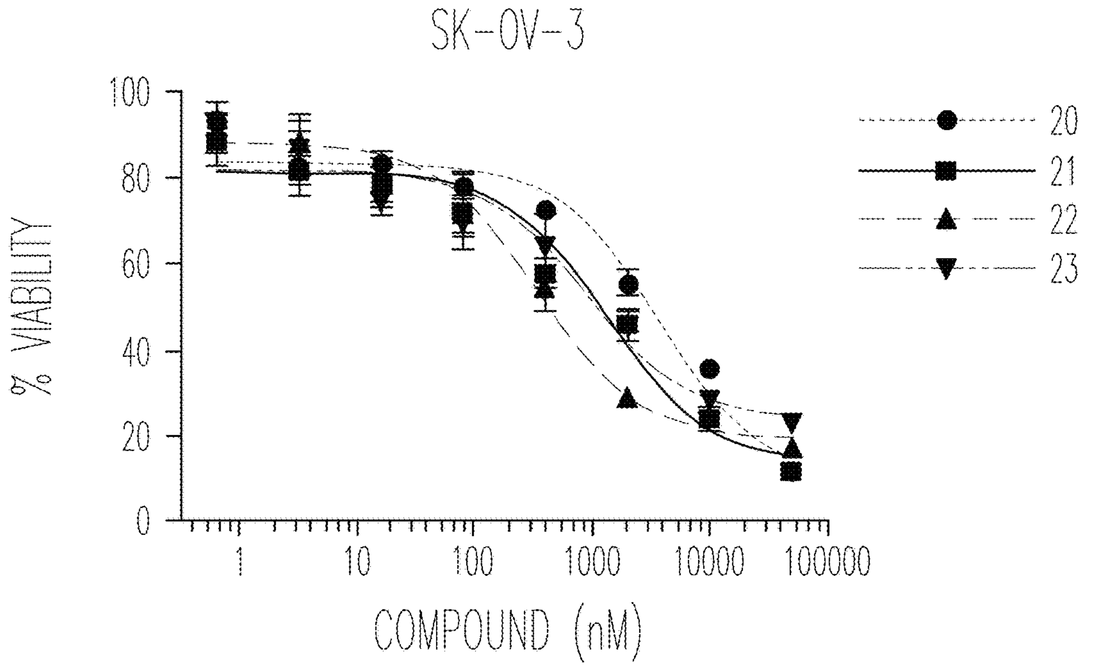
FIGS. 4A-4C show plots of percent cell viability as a function of compound concentration in ovarian and breast cancer cell lines.
Figure 4B:
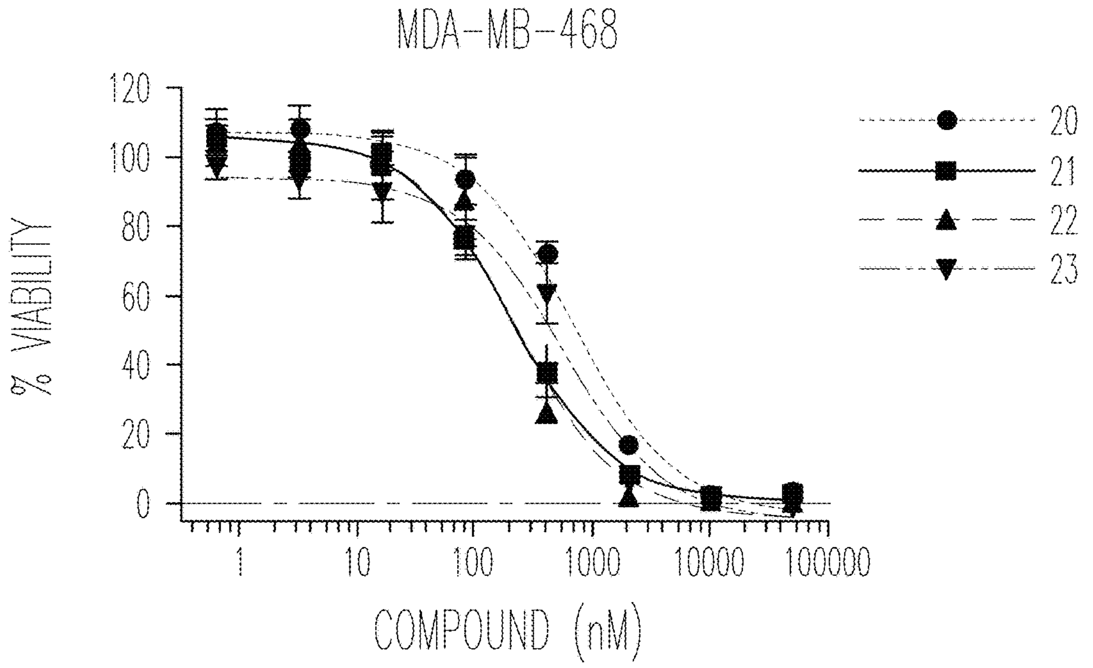
Figure 4C:
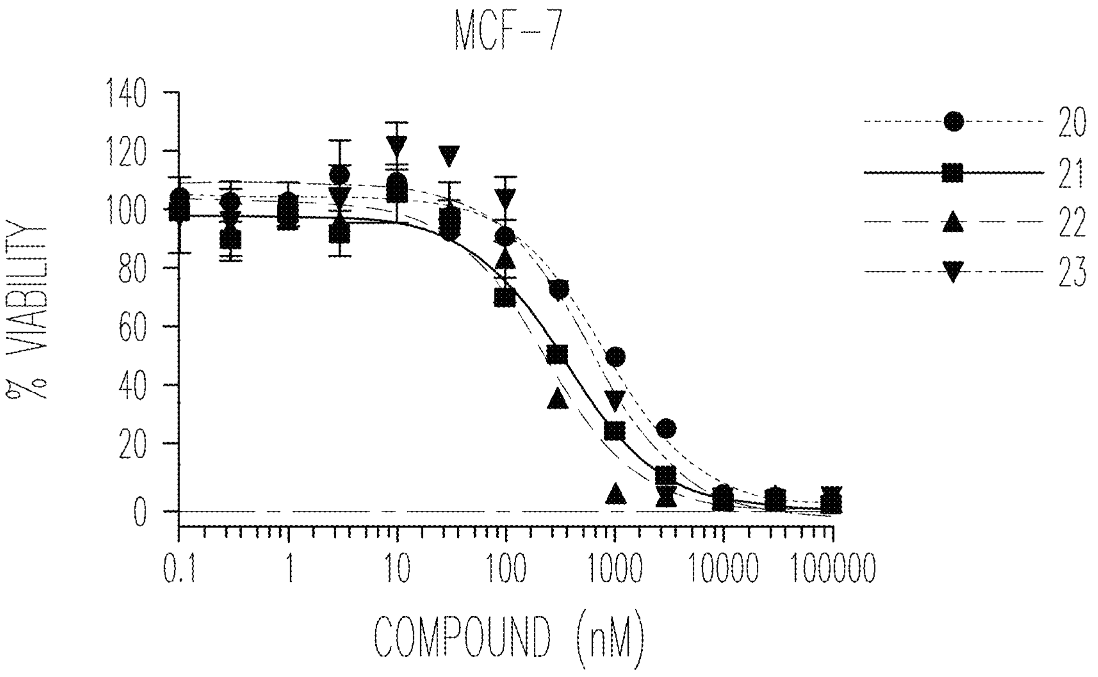

Additional compounds were tested in SK-OV-3 ovarian cancer, MDA-MB-468 breast cancer cells, and MCF-7 breast cancer cells. See FIG. 4, where compounds 20, 21, 22, and 23 have the following structures, respectively:

20

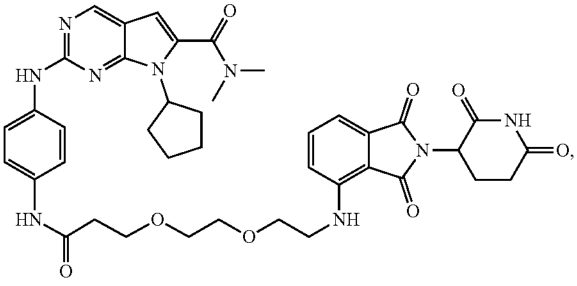

,

21

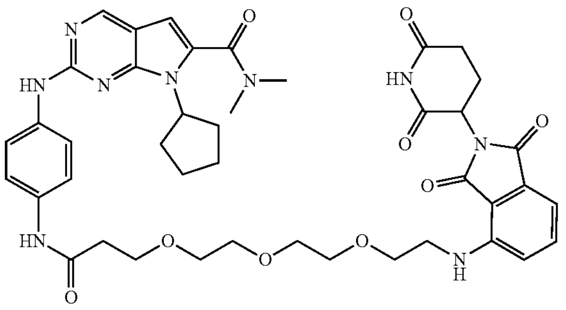

,

22

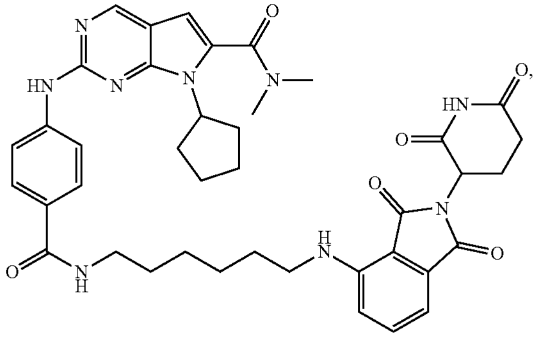

, and

-continued

23

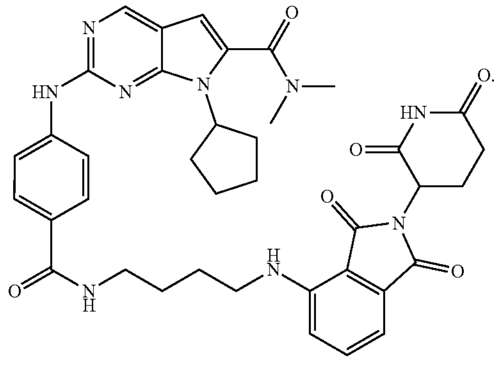

In this example, relates to a novel chemical strategy to tackle the challenge of N-Myc inhibition through the induced degradation of Aurora-A. The current working hypothesis is that once Aurora-A is degraded, the "unbound" N-Myc, even at high expression levels, will be rapidly eliminated through its native degradation pathway. Aurora-A degraders of the disclosure may provide effective therapeutic options for the treatment of aggressive neuroendocrine tumors, as well as other human cancers driven by elevated N-Myc protein levels.

It should also be noted that independent of its effects on N-Myc, Aurora-A is an attractive cancer drug target itself. Aurora-A is a critical kinase in cell cycle progression by regulating centrosome maturation, bipolar spindle assembly and chromosome separation. Several Aurora-A inhibitors have entered into clinical trials for the treatment of a variety of human cancers, including leukemia, ovarian cancer, and breast cancer, etc. However, there are no Aurora-A inhibitors approved by the FDA to date. Therefore, Aurora-A degraders could be potentially used for both N-Myc, dependent and independent cancers.

Figure 5B:
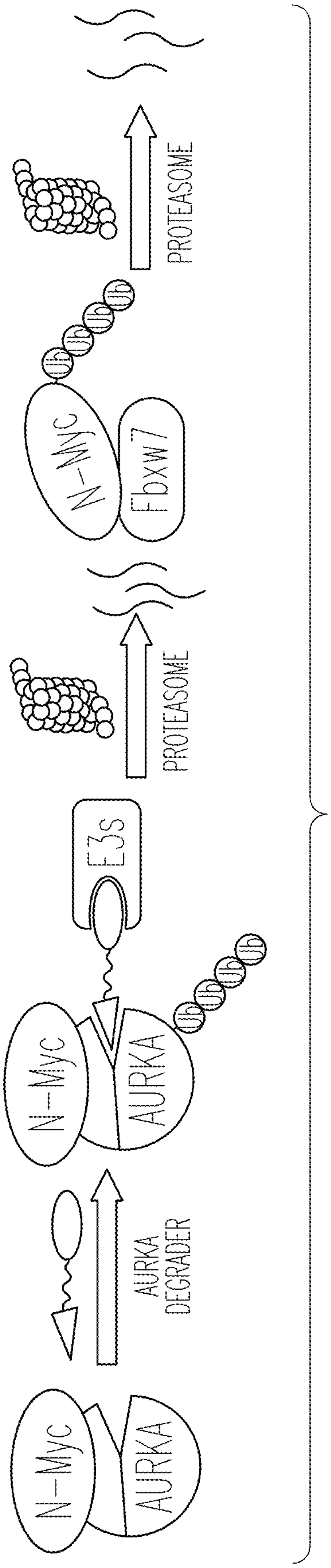
FIG. 5B is N-Myc depletion through the targeted protein degradation of Aurora-A AURKA, Aurora-A kinase.

A technology to facilitate targeted protein degradation using heterobifunctional molecules has emerged as a new modality in drug discovery. These heterobifunctional molecules (or proteolysis targeting chimeras, PROTACs®) comprise of a recognition moiety for a protein of interest (POI) and a ubiquitin ligase (E3) recruiting ligand connected via a chemical linker. Based on co-opting the cellular quality-control machinery, the ubiquitin proteasome system (UPS), these molecules function through proximity-induced polyubiquitination of the POI and subsequent proteasome-mediated degradation (FIG. 5*b*). Inspired by the fact that Aurora-A knockdown significantly decreases N-Myc levels, a novel chemical strategy was explored in this invention to address N-Myc overexpression through the targeted degradation of Aurora-A (versus inhibition). Until now, no Aurora-A degrading compounds were known. In preliminarily studies, first-in-class Aurora-A degraders have been successfully developed by conjugating a novel and selective Aurora-A binder to a recruiting ligand that binds to the E3 ligase(s) through optimized chemical linkers. After Aurora-A is degraded by these heterobifunctional compounds, the "exposed" N-Myc might be rapidly recognized by Fbxw7 for degradation (FIG. 5*b*). One of the biggest advantages of this strategy is that the developed degraders could induce the degradation of Aurora-A independent of N-Myc protein levels, which may yield active compounds in cancers characterized by N-Myc overexpression.

Figure 6A:
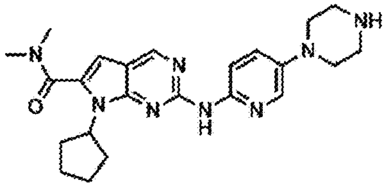
FIGS. 6A and B are in vitro kinase binding data.
Figure 6A:
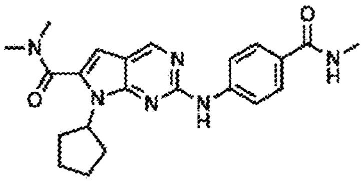
Figure 6A:
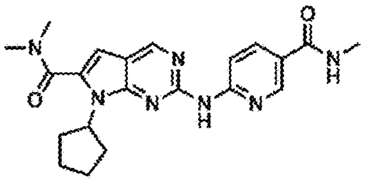
Figure 6A:
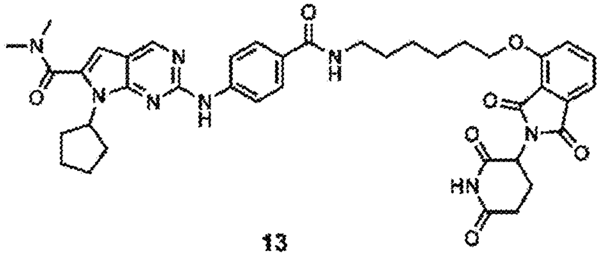
Figure 6A:
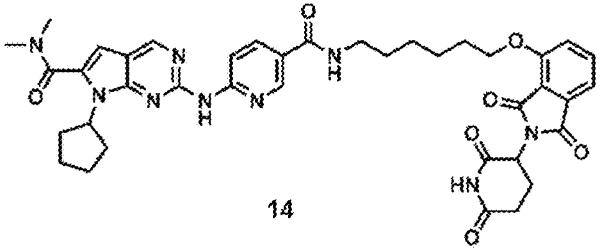
Figure 6A:
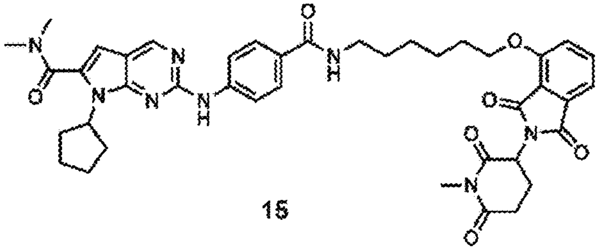
Figure 6B:
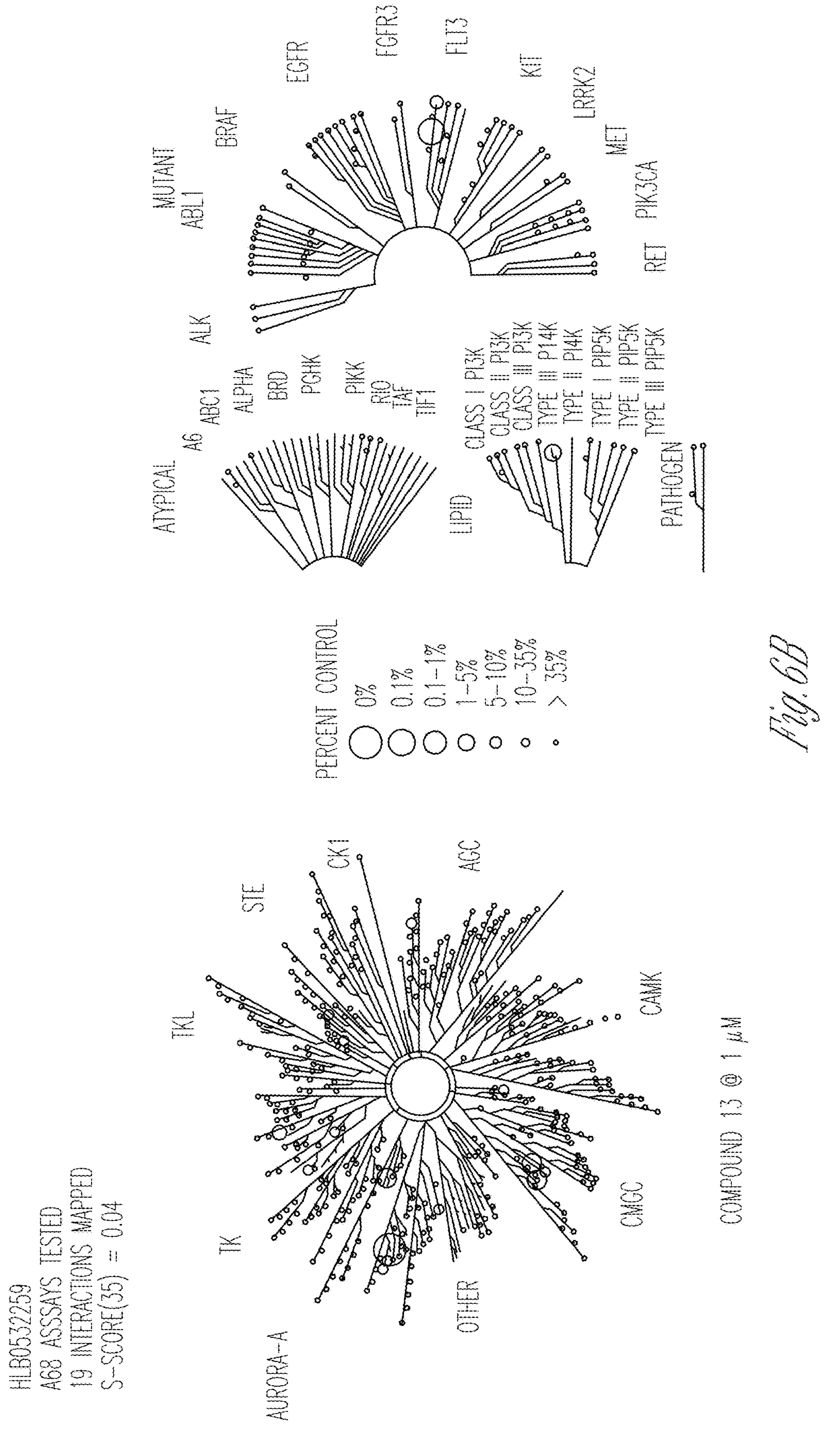
FIG. 6B shows kinome screening result against a panel of 468 kinases with 1 μM compound 13 (also referred to in the figure as HLB0532259) and its binding affinities to selected kinases.

Compound 11 tightly hinds to both Aurora-A and CDK4 with $K_d$ values of 0.85 nM and 3.0 nM, respectively. A heterobifunctional Aurora-A degrader, 13, was then designed and synthesized by connecting Aurora-A binder 11 with the E3-ligase Cereblon (CRBN) recruiting ligand Thalidomide via a hexanol linker (FIG. 6*a*). Interestingly, degrader 13 maintains its binding affinity to Aurora-A while exhibiting reasonable selectivity against its homolog Aurora-B (25-fold) and CDK4 (8-fold). In addition, 13 showed excellent selectivity for Aurora-A when screened against a panel of 468 kinases at 1 μM concentration (FIG. 6*b*). The N atom on the benzene ring in ribociclib is known to be critical for its high selectivity for CDK4/6 inhibition over other kinases. Consistent with this, restoration of this N atom yielded 12 and its PROTAC form 14, which showed a significant decrease of binding affinity with Aurora-A ($K_d$=380 nM). A control compound, 15, bearing an N-methyl group on the glutarimide moiety of the CRBN ligand Thalidomide, maintains similar binding profile as the active form 13. This N-methyl substitution has been reported to disrupt binding to CRBN. Both 14 and 15 were designed and synthesized as control compounds for validating the degradation mechanism in following experiments.

Figure 7A:
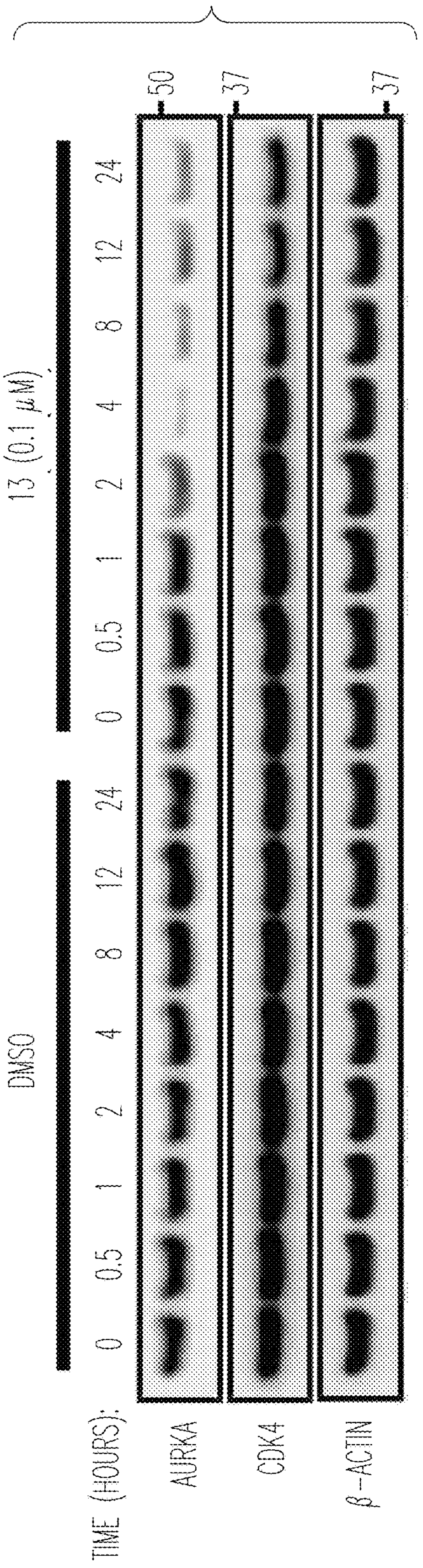
FIGS. 7A-F are the evaluations of compound 13 in MCF-7 breast cancer cells.
Figure 7B:
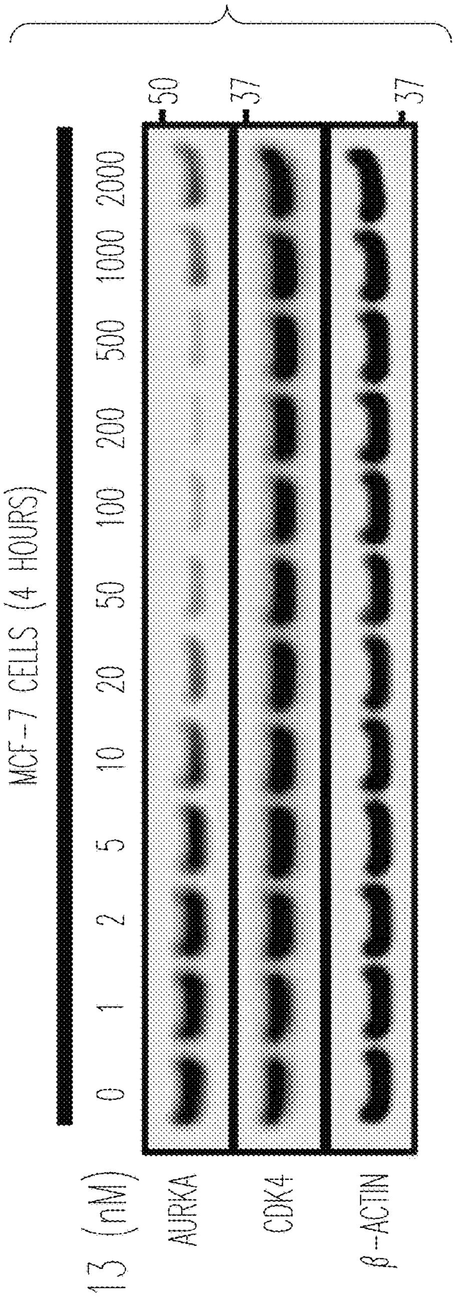
Figure 7C:
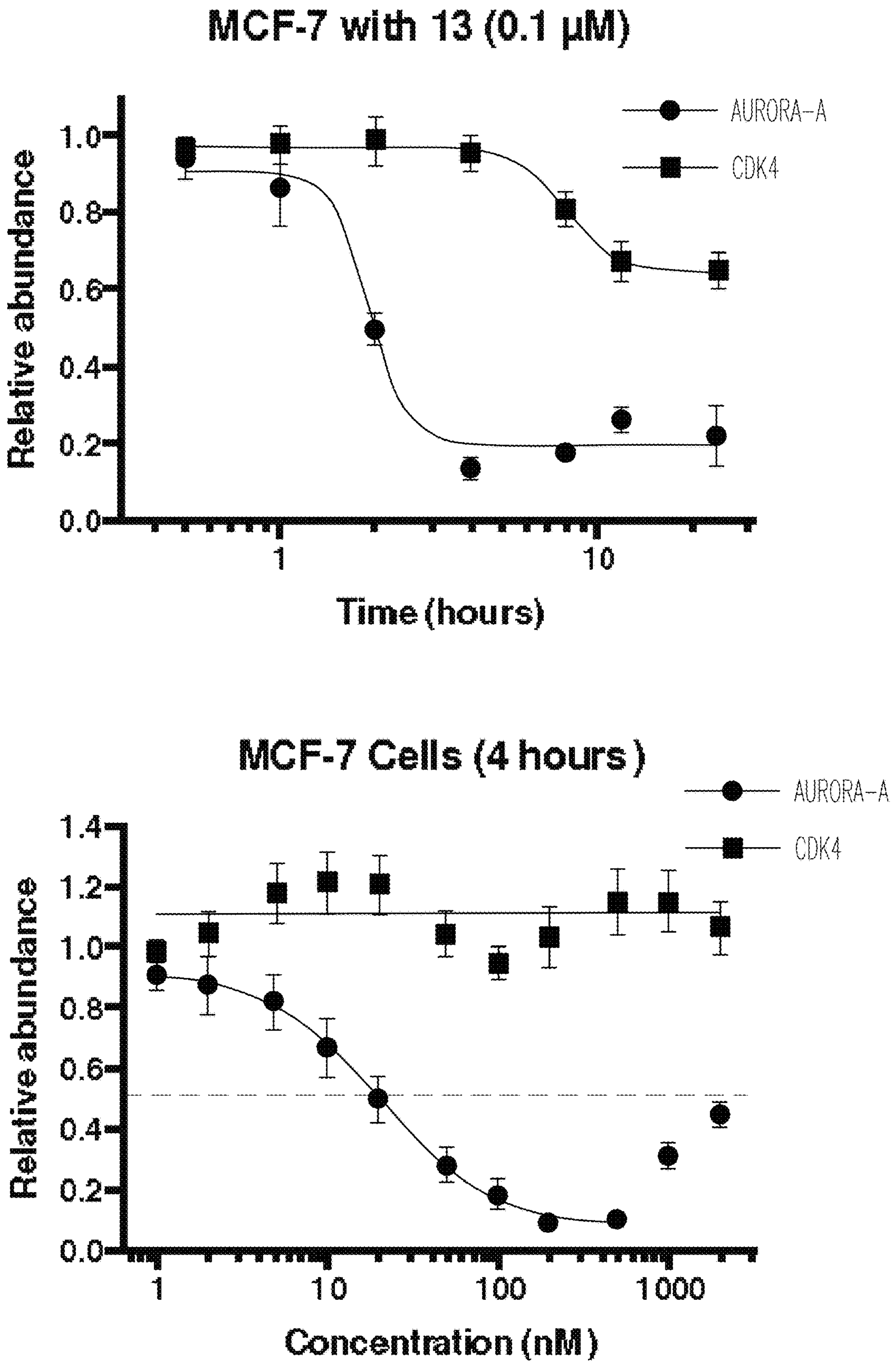
Figure 7D:
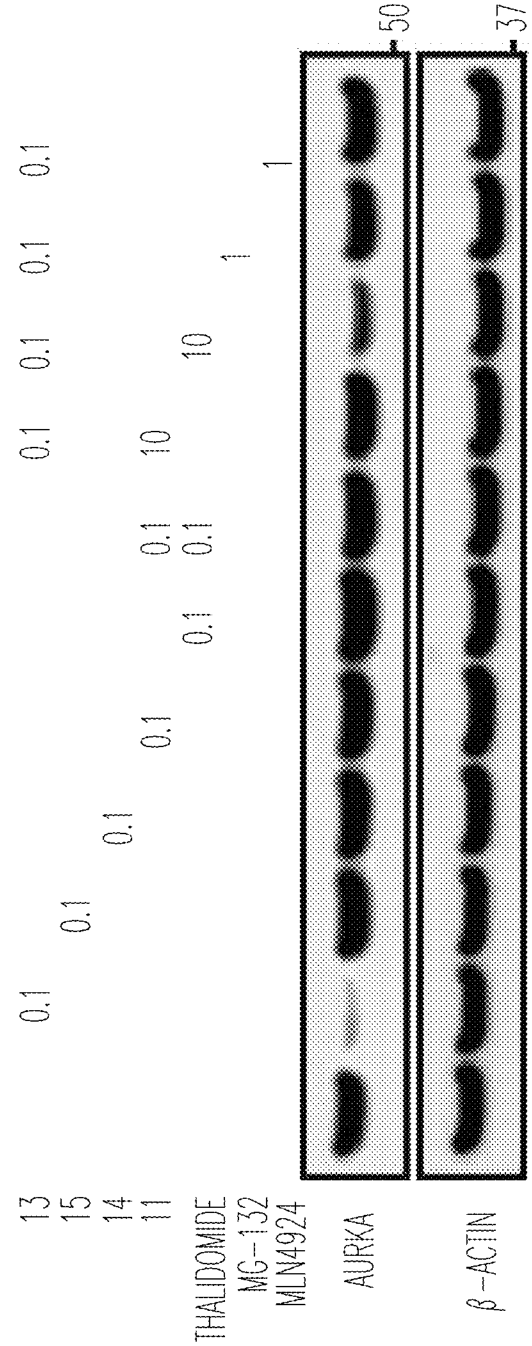
Figure 7E:
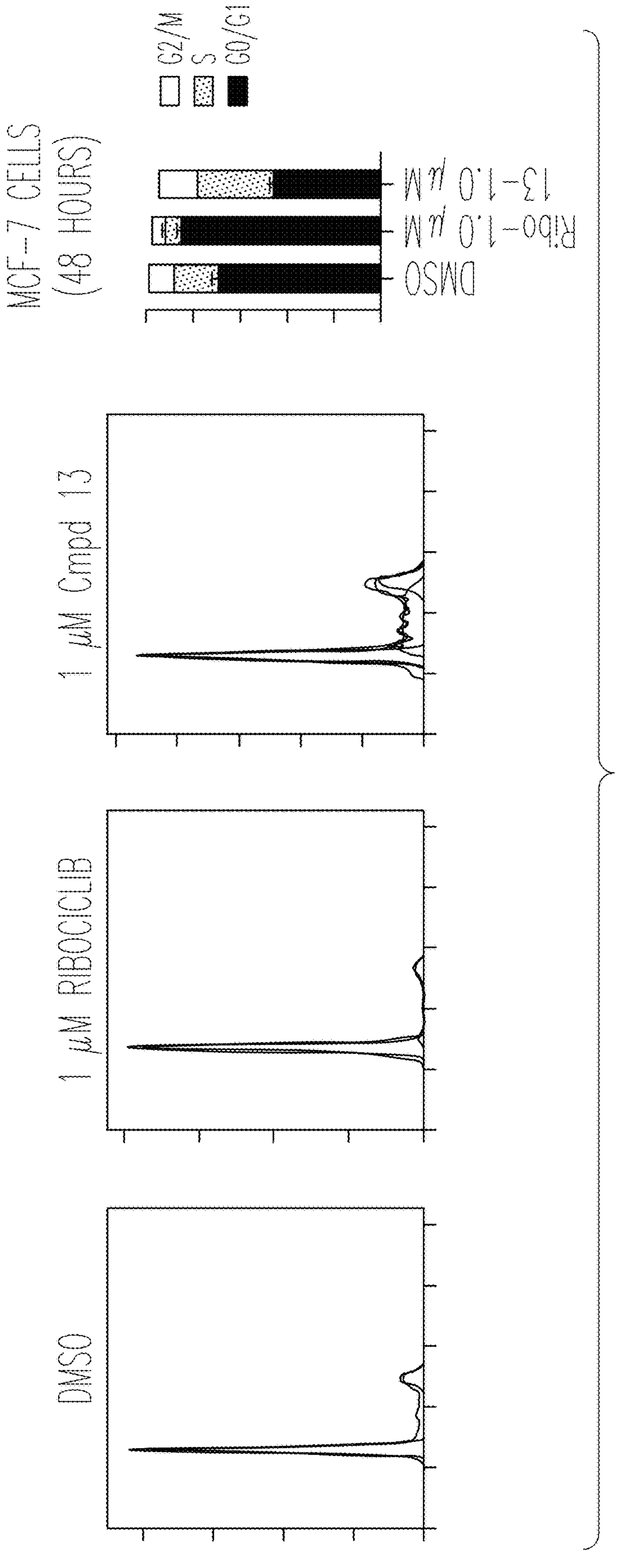
Figure 7F:
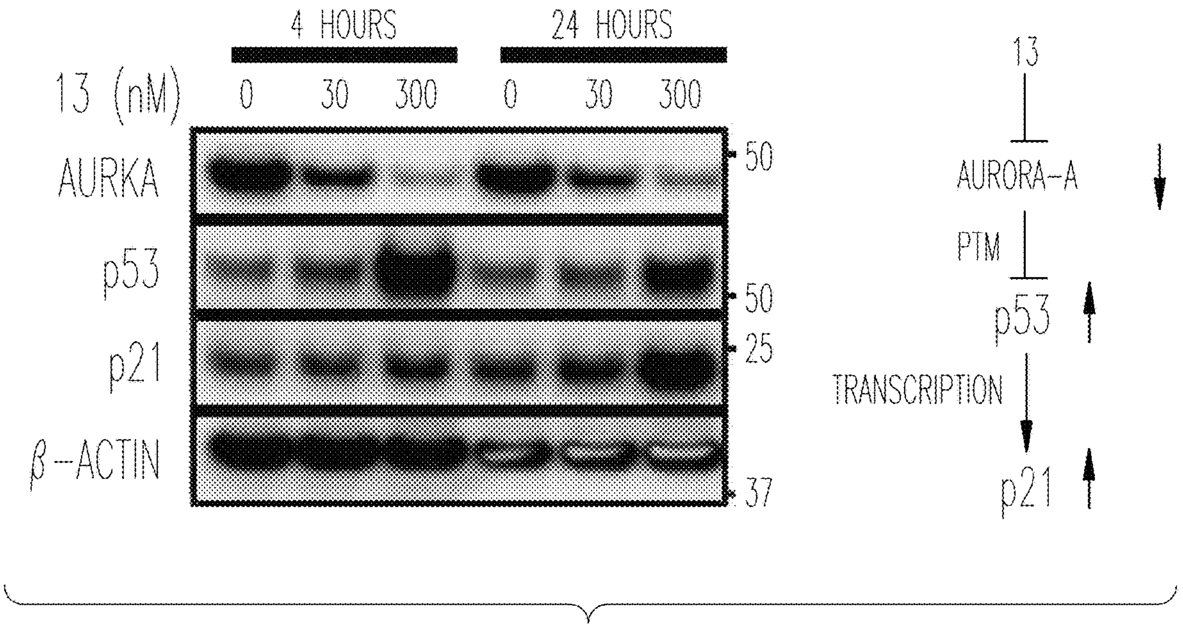

We firstly evaluated the protein degradation efficacy of these compounds in MCF-7 breast cancer cells. 13 could rapidly and potently induce the degradation of Aurora-A, while no obvious degradation of CDK4 was observed (FIG. 7A-B). The half-life of Aurora-A is 1.9 hours with 100 nM 13, and the calculated $DC_{50}$ value (half-maximal degradation concentration) for Aurora-A is 20 nM, and the $D_{max}$ (maximum degradation efficacy) is ~94% alter 4 hours. 13 also showed a lower degradation potency for Aurora-A at a high concentration (e.g. 2 μM), indicating the characteristic "hook effect" feature of a heterobifunctional degrader (FIG. 7C). Further mechanistic studies have validated that the induced degradation of Aurora-A requires the target engagement and induced proximity of Aurora-A and CRBN, and the degradation is dependent on the UPS (FIG. 7D). Aurora-A is an important kinase regulating mitosis in cell cycle progression. In the cell cycle analysis using propidium iodide DNA staining, 13 exhibited potent G2/M phase arrest, contrary to the effects of ribociclib that induces G0/G1 arrest by selectively inhibiting CDK4/6 kinases (FIG. 7E). This result indicates the on-target response of 13 in cell cycle regulation. Furthermore, Aurora-A directly phosphorylates tumor suppressor p53 to control its stability and transcriptional activity. Consistent with this, 13 significantly stabilized p53 and increased the abundance of the potent cyclin-dependent kinase inhibitor p21, whose expression is regulated by p53.

Figure 8A:
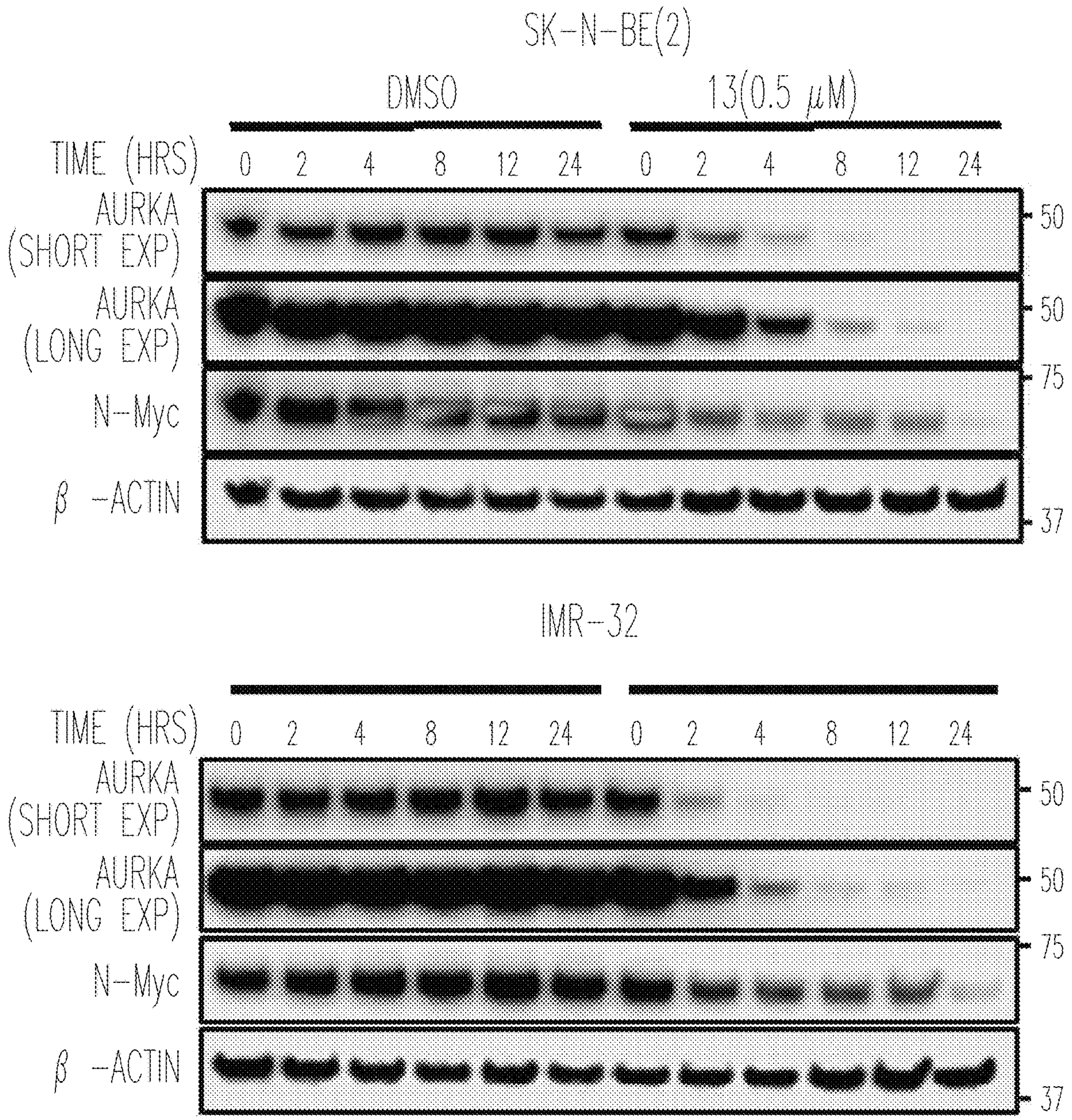
FIG. 8A is the time-dependent degradation of Aurora-A and N-Myc with 0.5 μM compound 13 in SK-N-BE(2) and IMR-32 cells.
Figure 8B:
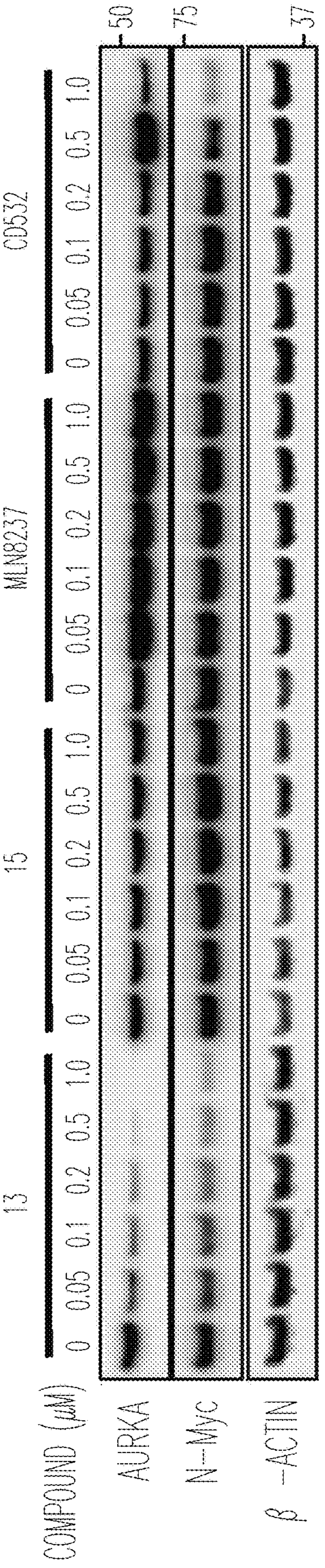
FIG. 8B is the dose-dependent degradation of Aurora-A and N-Myc after 24 hours in SK-N-BE(2) cells.

After the characterization of 13 for Aurora-A degradation, we next explored its capability to deplete N-Myc protein levels in MYCN amplified neuroblastoma cell lines IMR-32 and SK-N-BE(2). Type II Aurora-A inhibitors MLN8237 (Alisertib) and CD532 were included in these experiments for controls. Compound 13 could rapidly downregulate Aurora-A and N-Myc protein levels in both cell lines and achieved almost complete depletion of N-Myc after 24 hours (FIG. 8A). Additionally, in SK-N-BE(2) cells, 13 induced the degradation of Aurora-A and N-Myc in a dose-dependent manner, while the control compound, 15, did not affect the protein abundance even at the highest test concentration. Compared to MLN8237 and CD532, 13 was more potent for depleting N-Myc protein (FIG. 8B).

Figure 9:
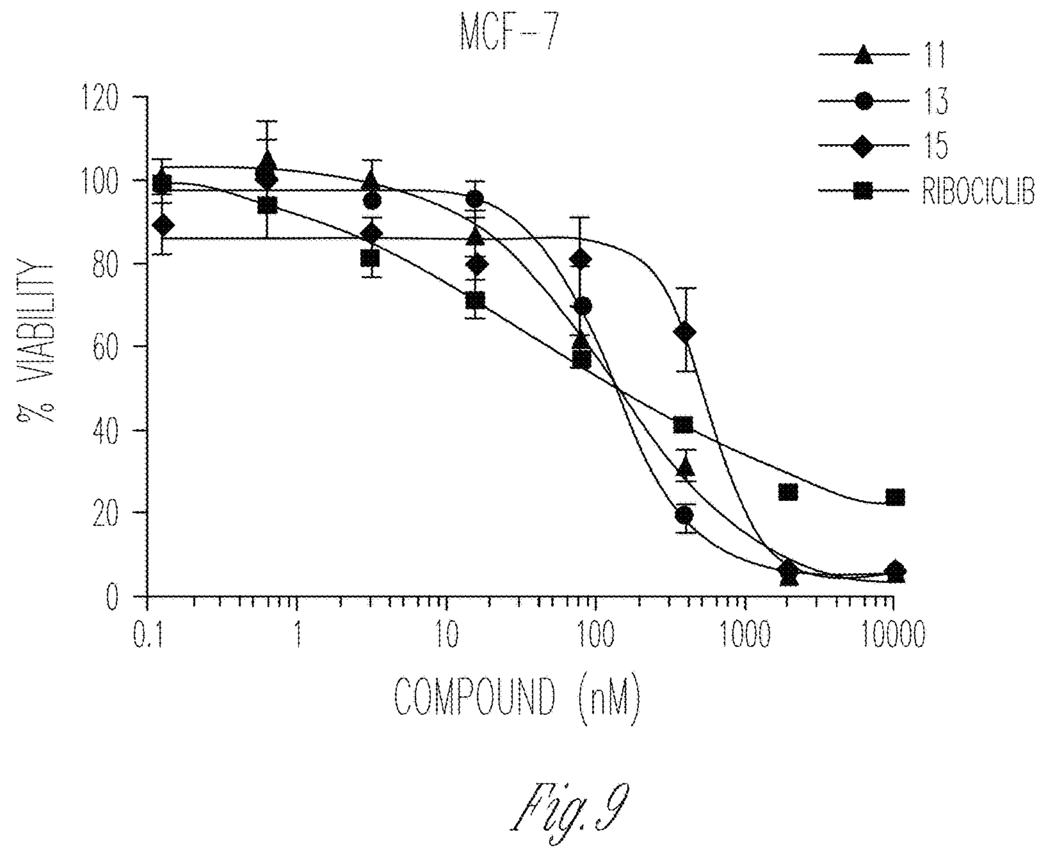
FIG. 9 is the cytotoxicity of Aurora-A degraders in various cancer cell lines. MCF-7 and HCC38: breast cancer cells; Huh7: liver cancer cells; IMR-32 and SK-N-B(2): neuroblastoma cells.
Figure 9:
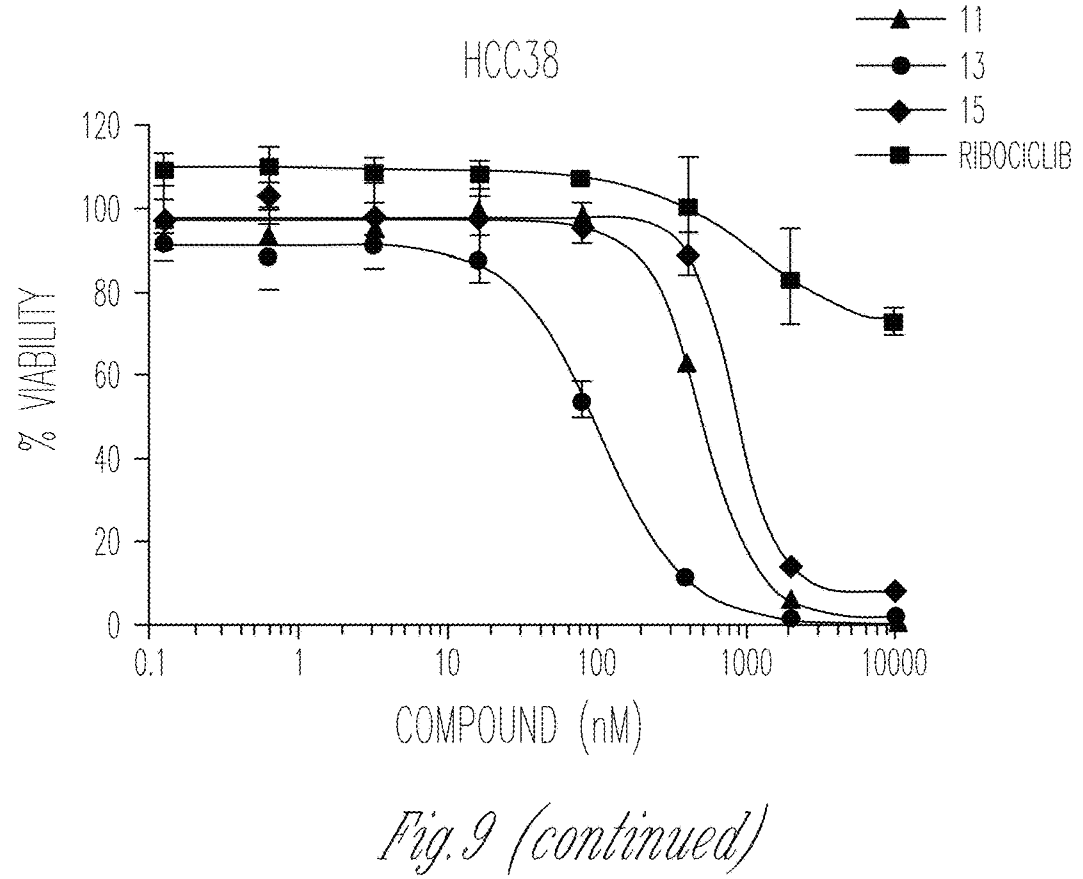
Figure 9:
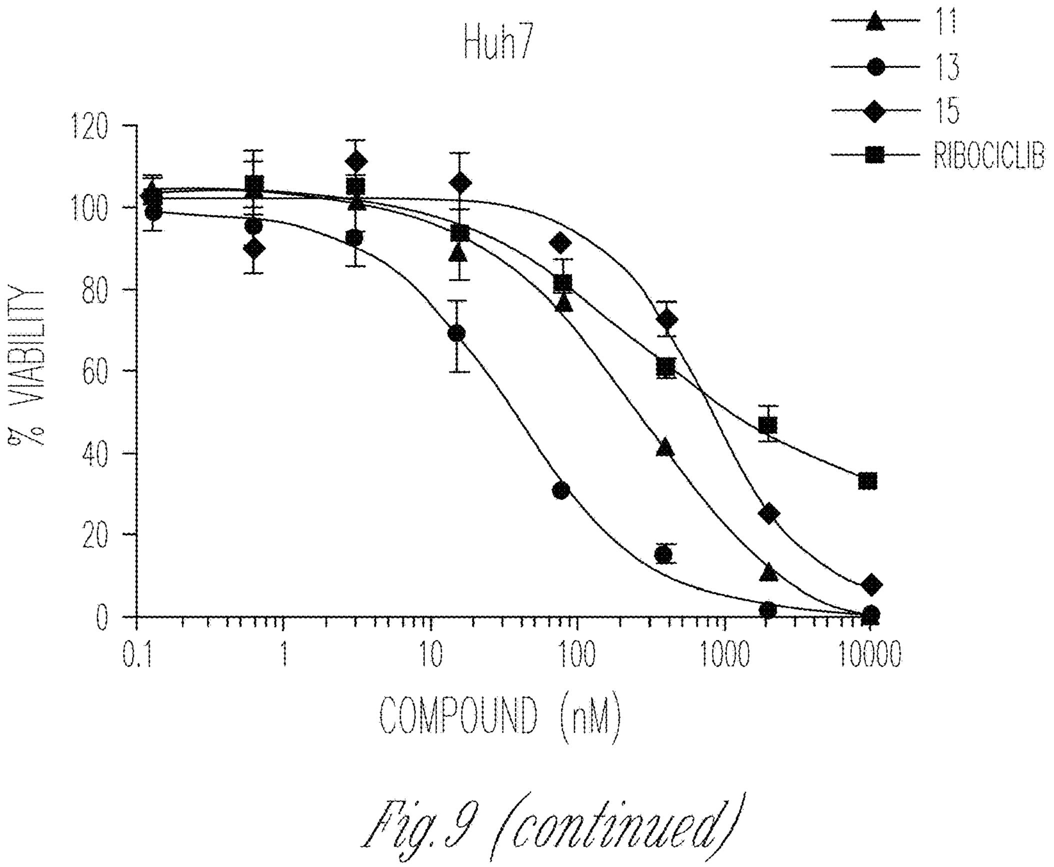
Figure 9:
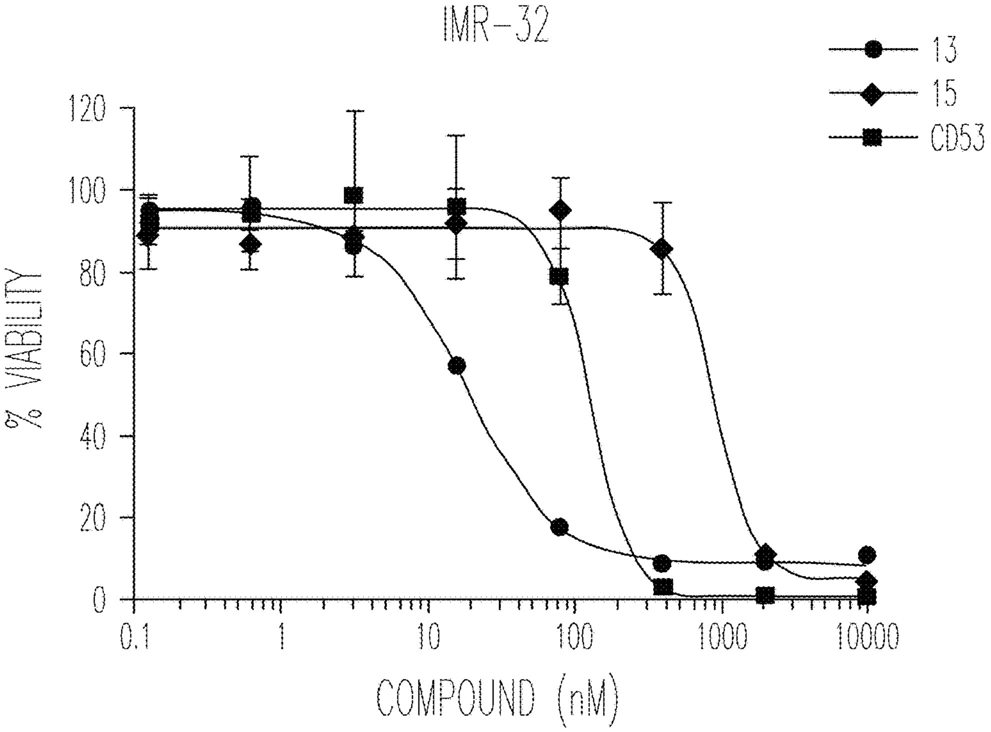
Figure 9:
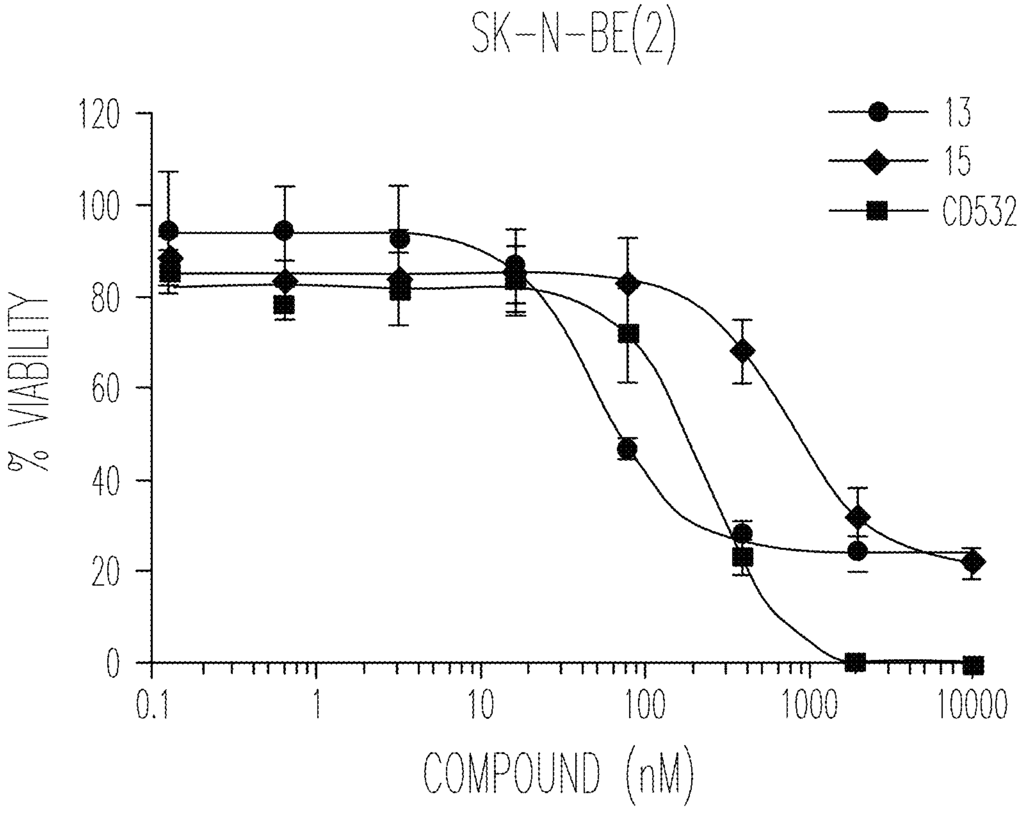

The degraders of the disclosure were evaluated for their cytotoxicity in a variety of cancer cell lines using Alamar blue cellular viability assay. 13 displayed potent cytotoxic effects against all tested cell lines with $IC_{50}$ values ranging from 18 nM to 135 nM. Interestingly, in MCF-7 cells which are highly sensitive to CDK4/6 inhibition, the inactive form 15 is only slightly less potent than 13 (4,4-fold). However, in ribociclib-resistant cell lines HCC38 and Huh7, 15 exhibited a more significant potency shift from 13, with 8.2-fold difference in HCC38 and 20.8-fold in Huh7, respectively. Furthermore, in MYCN amplified IMR-32 and SK-N-BE(2) cells, 13 is more potent than CD532, which is consistent with its efficacy to deplete N-Myc (FIG. 9).

Figure 10A:
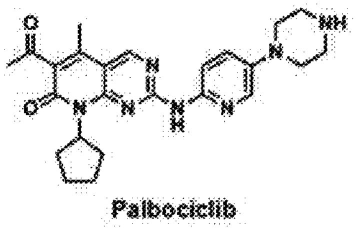
FIG. 10A is the chemical structures of Palbociclib- and Abemaciclib-based PROTACs® and their binding affinities to Aurora-A and CDK4-CyclinD1.
Figure 10A:
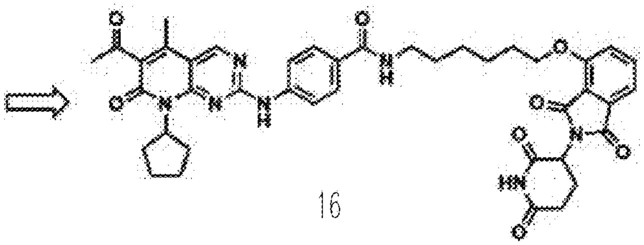
Figure 10A:
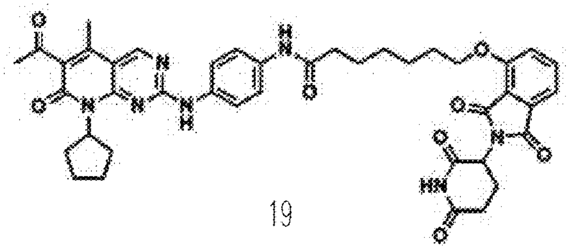
Figure 10A:
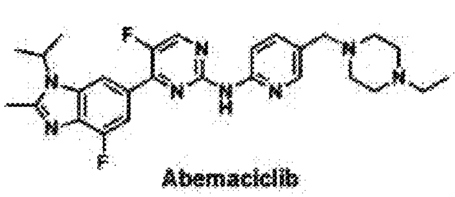
Figure 10A:
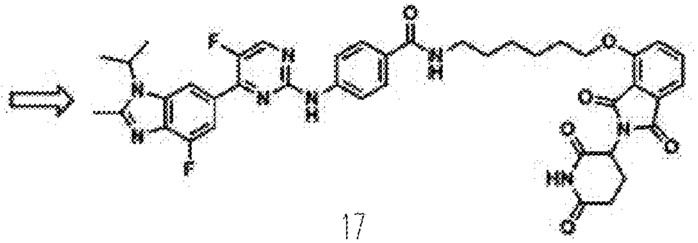
Figure 10A:
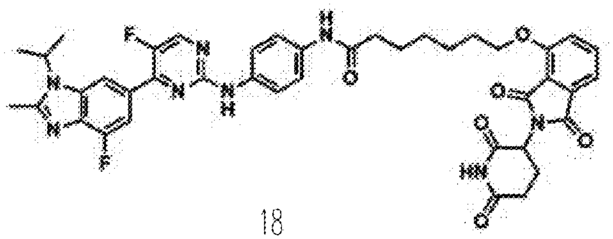
Figure 10B:
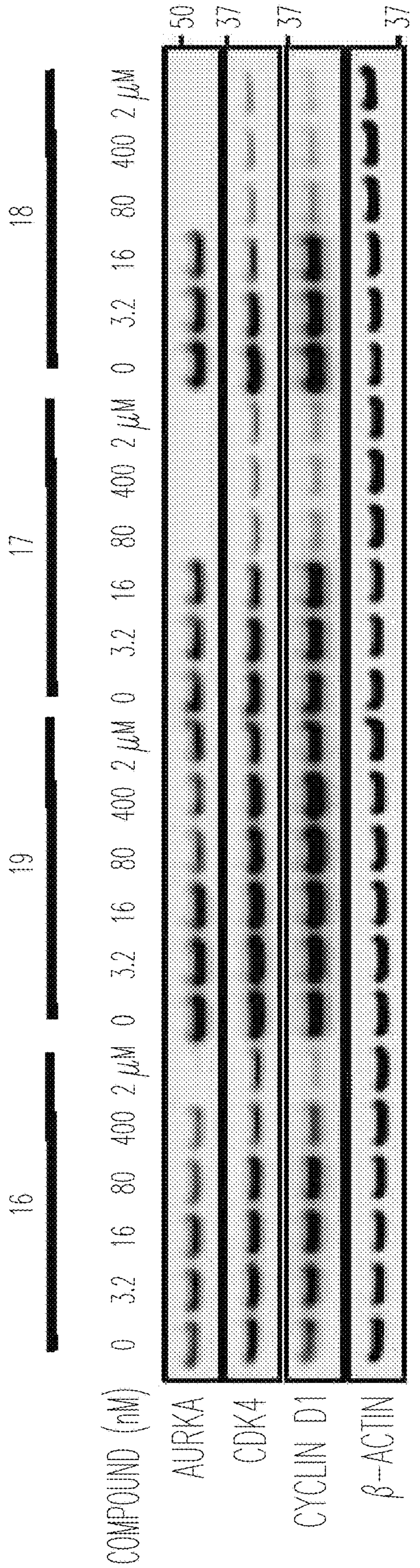
FIG. 10B is the degradation efficacy in MCF-7 cells after 21 hours.
Figure 10C:
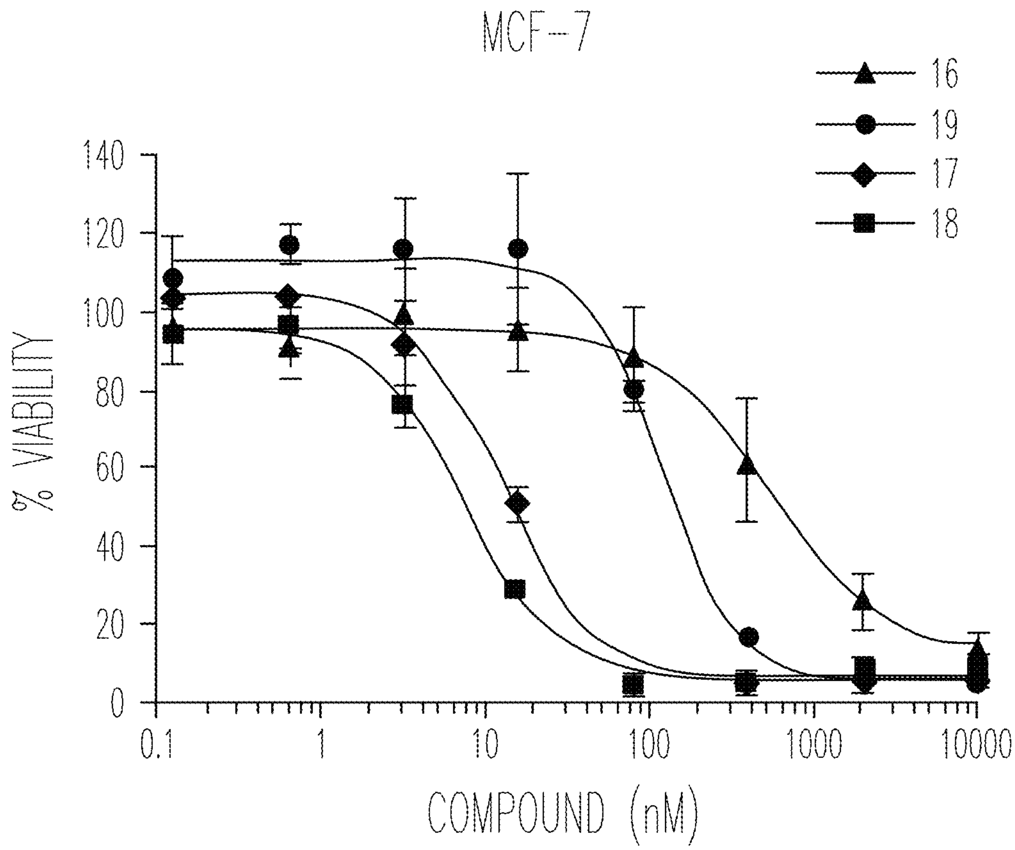
FIG. 10C is the cytotoxicity in MCF-7 cells.

In addition to ribociclib, there are two other CDK4/6 drugs that have received FDA approval for the treatment of breast cancer—palbociclib and abemaciclib (FIG. 10A). Four degraders were designed and synthesized, with two analogues for each chemical scaffold. Compound 16, a palbociclib analogue-based degrader, is weakly active in degrading Aurora-A and CDK4, presumably due to its weak binding to the target kinases. Interestingly, abemaciclib analogue-based 17 showed weak binding affinity with Aurora-A, yet maintained tight binding to CDK4-CyclinD1 ($K_d$=23 nM), but exhibited strong potency to induce the degradation of both kinases and cyclic: D1 in MCF-7 cells (FIG. 10A-B). Therefore, 17 may represent an example of a class of dual Aurora-A and CDK4 degraders. Consistent with their degradation potency, the two abemaciclib analogue-based degraders are more cytotoxic than the palbociclib analogue-based ones in MCF-7 cells, with 18 being the most potent compound.

Materials and Methods

Chemical Synthesis of 13 and 15:

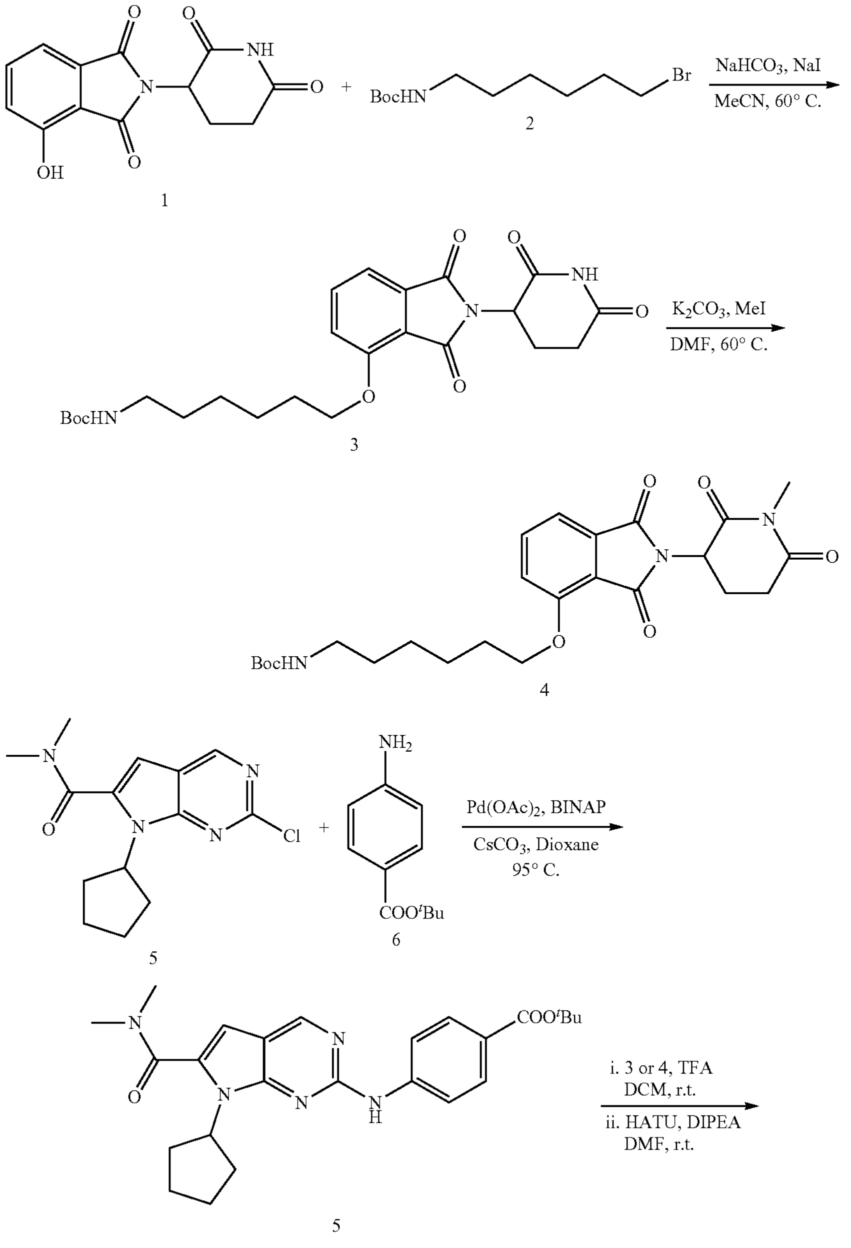

-continued

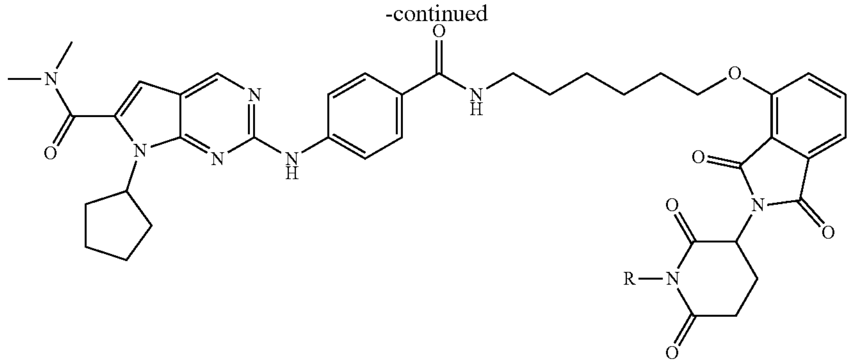

13 R = H
15 R = Me

General Protocol

Silica gel chromatography was performed on a Teledyne-Isco Combiflash Rf-200 instrument using Redisep Rf High Performance silica gel columns. Reverse-phase HPLC purification was performed on a Zorbax SB-C18 column (Zorbax SB-C18, 21.2×250 mm, 7 μM, Agilent Technologies). A two solvent system was used as the eluents: solvent A=distilled and deionized $H_2O$ (containing 0.1% TFA) and solvent B: MeCN (containing 0.1% TFA). The gradient (30 mL/min flow rate) consisted of: A:B 90:10 from 0-2 minutes, followed by a linear gradient to A:B 40:60 from 2-25 minutes, a second gradient to A:B 5:95 from 25-30 minutes, and an isocratic A:B 5:95 from 30-32 minutes.

Synthesis of Intermediate 3:

To a solution of 2-(2,6-dioxopiperidin-3-yl)-4-hydroxyisoindoline-1,3-dione (1) (100 mg, 0.364 mmol) was added tert-butyl (6-bromohexyl)carbamate (2) (120 mg, 0.428 mmol), $NaHCO_3$ (60 mg, 0.72 mmol), NaI (4.4 mg, 29 μmol) in MeCN (10 mL). The mixture was heated to 60° C. and was stirred for 18 h. After completion, the solvent was evaporated and the crude was purified using $SiO_2$ chromatography with a gradient of 0-100% EtOAc in DCM (compound elutes approx. at 50% EtOAc/DCM) to yield tert-butyl (6-((2-(2,6-dioxopiperidin-3-yl)-1,3-dioxoisoindolin-4-yl)oxy)hexyl)carbamate (3, yellow solid, 0.10 g, 57%). $^1H$ NMR (500 MHz, $CDCl_3$): δ 7.63-7.55 (m, 1H), 7.40-7.34 (m, 1H), 7.13 (dd, J=8.5, 2.4 Hz, 1H), 4.89 (dd, J=12.0, 5.4 Hz, 1H), 4.53 (d, J=11.2 Hz, 1H), 4.13-4.05 (m, 2H), 3.09-3.01 (m, 2H), 2.85-2.61 (m, 3H), 2.09-2.01 (m, 1H), 1.80 (q, J=4.2, 2.8 Hz, 2H), 1.49-1.41 (m, 4H), 1.36 (s, 9H), 1.35-1.30 (m, 1H). $^{13}C$ NMR (126 MHz, $CDCl_3$): δ 171.3, 168.4, 167.1, 165.7, 156.6, 156.0, 136.4, 133.7, 118.9, 117.1, 115.7, 79.0, 69.3, 49.0, 40.4, 31.3, 29.9, 28.7, 28.4 (3C, —$C(Me)_3$), 26.3, 25.5, 22.6.

Synthesis of Intermediate 4:

To a solution of tert-butyl (6-((2-(2,6-dioxopiperidin-3-yl)-1,3-dioxoisoindolin-4-yl)oxy)hexyl)carbamate (3) (30 mg, 0.063 mmol) was added $K_2CO_3$ (12 mg, 0.086 mmol), MeI (8 μL, 0.1 mmol) in DMF (3 mL). The mixture was heated to 60° C. and was stirred for 18 h. After completion, the reaction mixture was diluted in EtOAc and was washed with brine (30 mL×3). The organic layer was concentrated in vacuum and was purified using $SiO_2$ chromatography with a gradient of 0-100% EtOAc in DCM (compound elutes approx. at 50% EtOAc/DCM) to yield tert-butyl (6-((2-(1-methyl-2,6-dioxopiperidin-3-yl)-1,3-dioxoisoindolin-4-yl)oxy)hexyl)carbamate (4, yellow solid, 30.5 mg, 95%). $^1H$ NMR (500 MHz, $CDCl_3$): δ 7.60 (t, J=7.9 Hz, 1H), 7.37 (d, J=7.3 Hz, 1H), 713 (d, J=8.4 Hz, 1H), 4.88 (dd, J=12.4, 5.4 Hz, 1H), 4.49 (s, 1H), 4.10 (t, J=6.5 Hz, 2H), 3.14 (s, 3H), 3.05 (q. J=6.9 Hz, 2H), 2.90 (dd, J=16.1, 3.5 Hz, 1H), 2.79-2.62 (m, 2H), 2.06-1.98 (m, 1H), 1.82 (p, J=6.8 Hz, 2H), 1.51-1.41 (m, 4H), 1.36 (s, 10H), 1.35-1.30 (m, 1H). $^{13}C$ NMR (126 MHz, $CDCl_3$): δ 171.2, 168.8, 167.2, 165.8, 156.6, 156.0, 136.4, 133.8, 118.8, 117.1, 115.6, 78.9, 69.3, 49.8, 40.4, 31.9, 29.9, 28.7, 28.4 (3C, —$C(Me)_3$), 27.2, 26.4, 25.5, 21.9.

Synthesis of Intermediate 7:

To a flame-dried flask under Ar was added 2-chloro-7-cyclopentyl-N,N-dimethyl-7H-pyrrolo[2,3-d]pyrimidine-6-carboxamide (5) (300 mg, 1.02 mmol), tert-butyl 4-aminobenzoate (6) (270 mg, 1.42 mmol), $Pd(OAc)_2$ (45 mg, 0.20 mmol), BINAP (139 mg, 0,223 mmol) and $CsCO_3$ (0.83 g, 2.55 mmol) was suspended in anhydrous dioxane (50 ml). The suspension was flushed with argon and was heated to 95° C. under argon for 18 h. The reaction mixture was cooled and filtered through celite and was washed with EtOAc (50 mL×3). The filtrate was concentrated under vacuum and purified using $SiO_2$ chromatography with a gradient of 0-100% EtOAc in hexane (compound elutes approx. at 50% EtOAc/Hexane) to yield tert-butyl 4-((7-cyclopentyl-6-(dimethylcarbamoyl)-7H-pyrrolo[2,3-d]pyrimidin-2-yl)amino)benzoate (7, white solid, 0.30 g, 65%). $^1H$ NMR (500 MHz, $CDCl_3$): δ 8.60 (s, 1H), 7.89 (d, J=8.5 Hz, 2H), 7.69 (d, J=8.5 Hz, 2H), 7.48 (s, 1H), 6.38 (s, 1H), 4.72 (p, J=9.0 Hz, 1H), 3.08 (s, 6H), 2.59-2.46 (m, 2H), 2.06-1.95 (m, 4H), 1.72-1.62 (m, 2H), 1.53 (s, 9H), $^{13}C$ NMR (126 MHz, $CDCl_3$): δ 165.7, 164.0, 154.8, 151.7, 151.7, 144.1, 132.4, 130.5 (2C), 124.6, 117.0 (2C), 112.9, 100.8, 80.4, 58.0, 53.4, 39.4, 35.1, 30.1, 28.3 (3C, —$C(Me)_3$), 24.6 (2C, —$N(Me)_2$).

Synthesis of 13 and 15:

To a solution of intermediate tert-butyl 4-((7-cyclopentyl-6-(dimethylcarbamoyl)-7H-pyrrolo[2,3-d]pyrimidin-2-yl)amino)benzoate (7) (30 mg, 0.066 mmol) and tert-butyl (6-((2-(2,6-dioxopiperidin-3-yl)-1,3-dioxoisoindolin-4-yl)

oxy)hexyl)carbamate (3) (37 mg, 0.079 mmol) in DCM (1 mL) was added TFA (0.50 mL) and the resulting solution was stirred at room temperature for 30 min. The mixture was concentrated, and the residue was then dissolved in DMF (1 mL) followed by addition of HATU (50 mg, 0.13 mmol) and DIPEA (59 μL, 0.33 mmol). The resulting mixture was stirred for 18 h at room temperature. After completion, the reaction mixture was diluted in EtOAc and was washed with brine (30 mL×3). The organic layer was concentrated in vacuum and was purified using $SiO_2$ chromatography with a gradient of 0-30% MeOH in DCM (compound elutes approx. at 20% MeOH/DCM) to yield 7-cyclopentyl-2-((4-((6-((2-(2,6-dioxopiperidin-3-yl)-1,3-dioxoisoindolin-4-yl)oxy)hexyl)carbamoyl)phenyl)amino)-N,N-dimethyl-7H-pyrrolo[2,3-d]pyrimidine-6-carboxamide (13). The product was further purified reverse phase HPLC (10-90% MeCN (0.1% TFA) in $H_2O$ (0.1% TFA) as a yellow solid (15.1 mg, 30%). $^1$H NMR (500 MHz, DMSO): δ11.09 (s, 1H), 9.83 (s, 1H), 8.80 (d, J=2.1 Hz, 1H), 8.27 (s, 1H), 7.90 (dd, J=8.8, 2.4 Hz, 2H), 7.87 (s, 1H), 7.80 (dq, J=8.2, 3.2 Hz, 3H), 7.52 (dd, J=8.8, 2.3 Hz, 1H), 7.44 (dd, J=7.3, 2.2 Hz, 1H), 6.63 (d, J=2.1 Hz, 1H), 5.08 (dd, J=12.9, 5.3 Hz, 1H), 4.76 (q, J=8.6 Hz, 1H), 4.21 (t, J=6.1 Hz, 2H), 3.26 (q, J=6.7 Hz, 2H), 3.07 (s, 6H), 2.92-2.83 (m, 1H), 2.60 (s, 1H), 2.58-2.52 (m, 3H), 2.03-1.99 (m, 7H), 1.81-1.74 (m, 2H), 1.71-1.67 (m, 3H), 1.59-1.46 (m, 5H), 1.43-1.38 (m, 3H). $^{13}$C NMR (126 MHz, DMSO): δ 173.2, 170.4, 167.3, 166.1, 165.7, 163.2, 159.2, 158.9, 158.6, 158.3, 156.4, 154.9, 151.8, 151.6, 143.7, 137.4, 133.7, 132.9, 128.2, 127.2, 120.2, 117.5, 116.9, 116.7, 115.6, 114.6, 112.4, 101.2, 69.2, 57.5, 49.2, 35.0, 31.4, 30.1, 29.7, 28.8, 26.6, 25.5, 24.6, 22.4.

Similar procedure as above starting with intermediates 7 and 4 yielded 7-cyclopentyl-N,N-dimethyl-2-((4-((6-((2-(1-methyl-2,6-dioxopiperidin-3-yl)-1,3-dioxoisoindolin-4-yl)oxy)hexyl)carbamoyl)phenyl)amino)-7H-pyrrolo[2,3-d]pyrimidine-6-carboxamide (15) as a yellow solid (12.1 mg, 24%). $^1$H NMR (500 MHz, $CDCl_3$): δ 10.60 (s, 1H), 8.89 (s, 1H), 8.17-8.13 (m, 2H), 7.83-7.78 (m, 2H), 7.74 (app t, J=8.5, 7.3 Hz, 1H), 7.49 (d, J=7.2 Hz, 1H), 7.30-7.24 (m, 2H), 6.80 (s, 1H), 5.32 (s, 1H), 5.06 (dd, J=12.7, 5.4 Hz, 1H), 4.66 (p, J=8.9 Hz, 1H), 4.22 (q, J=5.5 Hz, 2H), 3.29 (s, 3H), 3.23 (d, J=6.0 Hz, 6H), 3.22-3.19 (m, 1H), 3.19-3.13 (m, 1H), 3.10-3.01 (m, 1H), 2.81 (qd, J=13.5, 4.8 Hz, 2H), 2.49-2.37 (m, 2H), 2.21-2.10 (m, 3H), 2.06-1.97 (m, 2H), 1.91 (p, J=6.2 Hz, 2H), 1.86-1.70 (m, 5H), 1.61-1.54 (m, 4H), 1.28 (s, 1H).

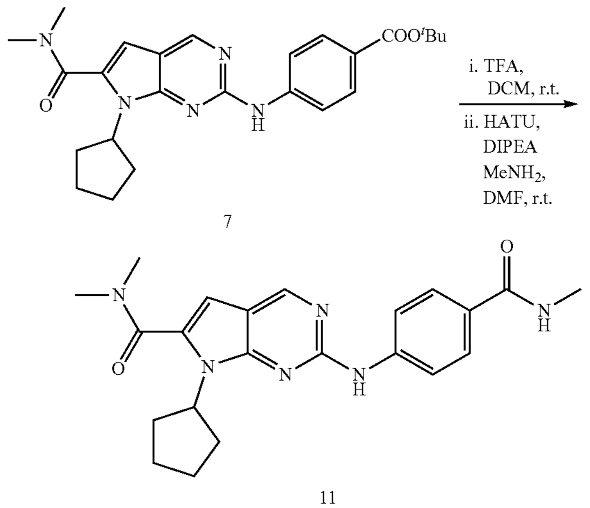

7

11

To a solution of Cert-butyl 4-((7-cyclopentyl-6-(dimethylcarbamoyl)-7H-pyrrolo[2,3-d]pyrimidin-2-yl)amino)benzoate (7) (30 mg, 0.066 mmol) in DCM (1 mL) was added TFA (0.50 mL) and the resulting solution was stirred at room temperature for 30 min. The mixture was concentrated, and the residue was then dissolved in DMF (1 mL) followed by addition of HATU (50 mg, 0.13 mmol) and DIPEA (59 μL, 0.33 mmol) and $MeNH_2$ in THF (2.0 M, 1 mL). The resulting mixture was stirred for 18 h at room temperature. After completion, the reaction mixture was diluted in EtOAc and was washed with brine (30 mL×3). The organic layer was concentrated in vacuum and was purified using $SiO_2$ chromatography with a gradient of 0-30% MeOH in DCM (compound elutes approx. at 20% MeOH/DCM) to yield 7-cyclopentyl-N,N-dimethyl-2-((4-(methylcarbamoyl)phenyl)amino)-7H-pyrrolo[2,3-d]pyrimidine-6-carboxamide (11). 1H NMR (500 MHz, DMSO): δ 9.84 (s, 1H), 8.80 (s, 1H), 8.25 (q, J=4.5 Hz, 1H), 7.90 (d, J=8.6 Hz, 2H), 7.79 (d, J=8.7 Hz, 2H), 6.63 (s, 1H), 4.74 (q, J=8.8 Hz, 1H), 3.06 (br s, 6H), 2.78 (d, J=4.4 Hz, 3H), 2.49-2.45 (m, 1H), 2.05-1.98 (m, 5H), 1.71-1.67 (m, 2H).

Similar procedures to those described above were used to synthesize the following compounds:

7-cyclopentyl-N,N-dimethyl-2-((5-(methylcarbamoyl)pyridin-2-yl)amino)-7H-pyrrolo[2,3-d]pyrimidine-6-carboxamide Similar Procedure as Above (12)

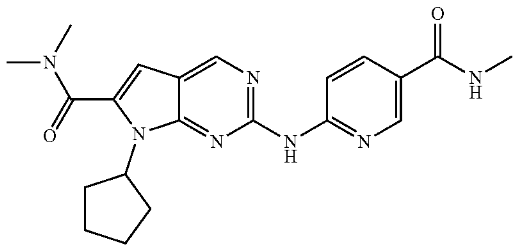

$^1$H NMR (500 MHz, DMSO): δ10.93 (br s, 1H), 8.97 (s, 1H), 8.79 (s, 1H), 8.57 (q, J=4.5 Hz, 1H), 8.30 (dd, J=9.0, 2.5 Hz, 1H), 8.02 (d, J=8.8 Hz, 1H), 6.78 (s, 1H), 4.79 (p, J=8.8 Hz, 1H), 3.07 (s, 6H), 2.82 (dd, J=4.6, 1.6 Hz, 3H), 2.39 (q, J=8.6, 6.3 Hz, 2H), 2.02 (dt, J=17.0, 8.9 Hz, 4H), 1.68 (q, J=5.9 Hz, 2H).

7-cyclopentyl-2-((4-((6-((2-(2,6-dioxopiperidin-3-yl)-1,3-dioxoisoindolin-4-yl)amino)hexyl)carbamoyl)-phenyl)amino)-N,N-dimethyl-7H-pyrrolo[2,3-d] pyrimidine-6-carboxamide (22)

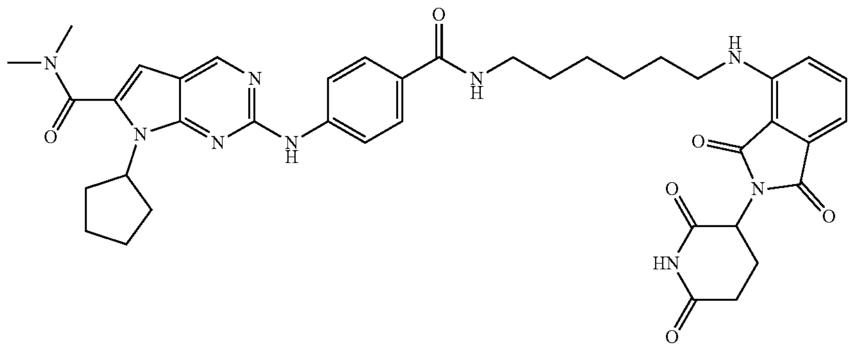 [SMILES: CN(C)C(=O)c1cc2cnc(Nc3ccc(C(=O)NCCCCCCNc4cccc5c4C(=O)N(C4CCC(=O)NC4=O)C5=O)cc3)nc2n1C1CCCC1]

1H NMR (500 MHz, DMSO): δ11.09 (s, 1H), 9.83 (s, 1H), 8.80 (s, 1H), 8.27 (s, 1H), 7.90 (d, J=8.7 Hz, 2H), 7.80 (d, J=8.8, 2 H), 7.58 (td, J=8.1, 3.0 Hz, 1H), 7.09 (dd, J=8.6, 3.0 Hz, 1H), 7.02 (dd, J=7.3, 2.9 Hz, 1H), 6.63 (s, 1H), 6.54 (s, 1H), 5.07-5.03 (m, 1H), 4.77-4.74 (m, 1H), 3.32-3.23 (m, 4H), 3.06 s, 6H), 2.91-2.85 (m, 1H), 2.64-2.57 (m, 3H), 2.01 (br s, 6H), 1.69 (br s, 2H), 1.60-1.53 (m, 4H), 1.36 (br s, 4H).

7-cyclopentyl-2-((4-(3-(2-(2-((2-(2,6-dioxopiperidin-3-yl)-1,3-dioxoisoindolin-4-yl)amino)ethoxy) ethoxy)-propanamido)phenyl)amino)-N,N-dimethyl-7H- pyrrolo[2,3-d]pyrimidine-6-carboxamide (20)

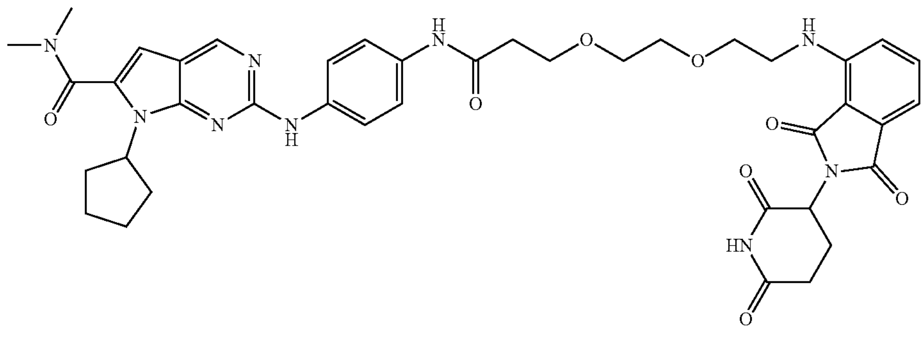 [SMILES: CN(C)C(=O)c1cc2cnc(Nc3ccc(NC(=O)CCOCCOCCNc4cccc5c4C(=O)N(C4CCC(=O)NC4=O)C5=O)cc3)nc2n1C1CCCC1]

1H NMR (500 MHz, DMSO): δ 11.08 (s, 1H), 9.81 (s, 1H), 9.51 (s, 1H), 8.74 (s, 1H), 7.70 (d, J=8.8 Hz, 2H), 7.57-7.52 (m, 3H), 7.09 (d, J=8.6 Hz, 1H), 7.01 (d, J=7.0 Hz, 1H), 6.60 (s, 2H), 5.05 (dd, J=12.8 Hz, 5.4 Hz, 1H), 4.70 (p, J=8.8 Hz, 1H), 3.70 (t, J=6.2 Hz, 2H), 3.61 (t, J=5.4 Hz, 2H), 3.55 (ddd, J=8.0, 5.2, 2.9 Hz, 4H), 3.43-3.42 (br s, 2H), 3.05 (br s, 6H), 2.90-2.83 (m, 1H), 2.60-2.58 (m, 1H), 2.48-2.36 (m, 4H), 2.04-1.91 (m, 6H), 1.65-1.63 (m, 2H).-

7-cyclopentyl-2-((4-(3-(2-(2-(2-((2-(2,6-dioxopiperidin-3-yl)-1,3-dioxoisoindolin-4-yl)amino)ethoxy)eth-oxy)ethoxy)propanamido)phenyl)amino)-N,N-dimethyl-7H-pyrrolo[2,3-d]pyrimidine-6-carboxamide (21)

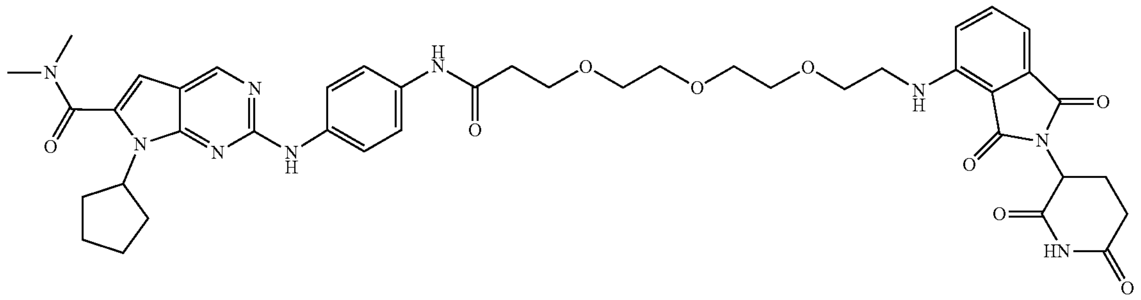 [SMILES: CN(C)C(=O)c1cc2cnc(Nc3ccc(NC(=O)CCOCCOCCOCCNc4cccc5c4C(=O)N(C4CCC(=O)NC4=O)C5=O)cc3)nc2n1C1CCCC1]

1H NMR (500 MHz, DMSO): δ11.09 (s, 1H), 9.83 (s, 1H), 9.55 (s, 1H), 8.75 (s, 1H), 7.71 (d, J=8.9 Hz, 2H), 7.55 (td, J=8.8, 6.9 Hz, 3H), 7.11 (d, J=8.6 Hz, 1H), 7.03 (d, J=7.0 Hz, 1H), 6.62-6.60 (m, 2H), 5.06 (dd, J=12.8, 5.4 Hz, 1H), 4.72 (p, J=8.8 Hz, 1H), 3.69 (t, J=6.2 Hz, 2H), 3.60 (t, J=5.5 Hz, 2H), 3.54 (s, 4H), 3.52 (s, 4H), 3.44 (br s, 2H), 3.06 (br s, 6H), 2.92-2.85 (m, 1H), 2.69-2.60 (m, 1H), 2.49-2.41 (m, 2H), 2.04-1.93 (m, 6H), 1.66-1.64 (2H).

7-cyclopentyl-2-((4-((4-((2-(2,6-dioxopiperidin-3-yl)-1,3-diaxoisoindolin-4-yl)amino)butyl)carbamoyl)-phenyl)amino)-N,N-dimethyl-7H-pyrrolo[2,3-d]pyrimidine-6-carboxamide (23)

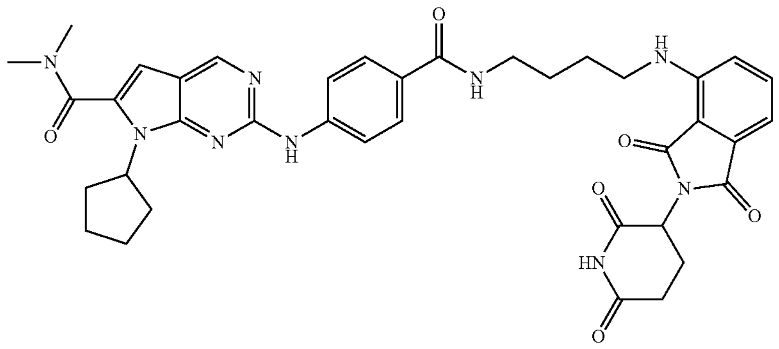 [SMILES: CN(C)C(=O)c1cc2cnc(Nc3ccc(C(=O)NCCCCNc4cccc5c4C(=O)N(C4CCC(=O)NC4=O)C5=O)cc3)nc2n1C1CCCC1]

1H NMR (500 MHz, DMSO): δ 11.09 (s, 1H), 9.83 (s, 1H), 8.81 (s, 1H), 8.32 (t, J=5.7 Hz, 1H), 7.91 (d, J=8.5 Hz, 2H), 7.81 (d, J=8.6 Hz, 2H), 7.59-7.56 (m, 1H), 7.13 (d, J=8.6 Hz, 1H), 7.02 (d, J=7.0 Hz, 1H), 6.63 (s, 1H), 6.59 (br s, 1H), 5.05 (dd, J=12.8, 5.4 Hz, 1H), 4.76 (p, J=9.0 Hz, 1H), 3.37-3.29 (m, 4H), 3.07 (br s, 6H), 2.88 (ddd, J=16.9, 13.7, 5.4 Hz, 1H), 2.65-2.57 (m, 3H), 2.02 (br s, 6H), 1.70-1.67 (m, 2H), 1.63 (br s. 4H).-

7-cyclopentyl-2-((4-((2-(2-(2-((2-(2,6-dioxopiperidin-3-yl)-1,3-dioxoisoindolin-4-yl)amino)ethoxy) ethoxy)-ethyl)carbamoyl)phenyl)amino)-N,N-di-axoisoindolin-4-yl)amino)butyl)carbamoyl)-phenyl) amino)-N,N-dimethyl-7H-pyrrolo[2,3-d]pyrimidine-6-carboxamide (HLB-0534329)

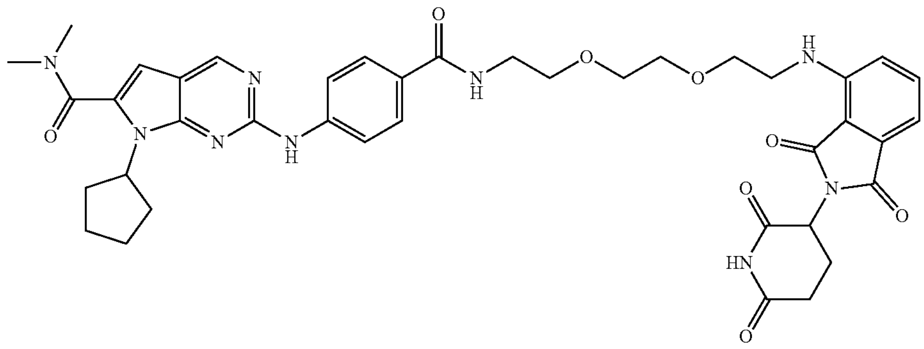 [SMILES: CN(C)C(=O)c1cc2cnc(Nc3ccc(C(=O)NCCOCCOCCNc4cccc5c4C(=O)N(C4CCC(=O)NC4=O)C5=O)cc3)nc2n1C1CCCC1]

1H NMR (500 MHz, DMSO): δ 11.09 (s, 1H), 9.90 (s, 1H), 8.82 (s, 1H), 8.35 (t, J=5.6 Hz, 1H), 7.90 (d, J=8.7 Hz, 2H), 7.83 (d, J=8.8 Hz, 2H), 7.55 (dd, J=8.5, 7.0 Hz, 1H), 7.11 (d, J=8.6 Hz, 1H), 7.02 (d, J=7.1 Hz, 1H), 6.64 (s, 1H), 6.60 (br s, 1H), 5.06 (dd, J=12.8, 5.4 Hz, 1H), 4.75 (p, J=8.6 Hz, 1H), 3.62 (t, J=5.4 Hz, 2H), 3.60-3.56 (m, 4H), 3.55 (t, J=6.0 Hz, 2H), 3.45-3.40 (m, 4H), 3.07 (br s, 6H), 2.88 (ddd, J=16.9, 13.8, 5.4 Hz, 1H), 2.60-2.59 (m, 1H), 2.49-2.46 (m, 2H), 2.04-2.00 (m, 6H), 1.70-1.67 (m, 2H).

7-cyclopentyl-2-((5-((6-((2-(2,6-dioxopiperidin-3-yl)-1,3-dioxoisoindolin-4-yl)amino)hexyl)carbamoyl)-pyridin-2-yl)amino)-N,N-dimethyl-dioxoisoindolin-4-yl)amino)ethoxy)ethoxy)-ethyl)carbamoyl) phenyl)amino)-N,N-diaxoisoindolin-4-yl)amino) butyl)carbamoyl)-phenyl)amino)-N,N-dimethyl-7H-pyrrolo[2,3-d]pyrimidine-6-carboxamide (HLB-0534330)

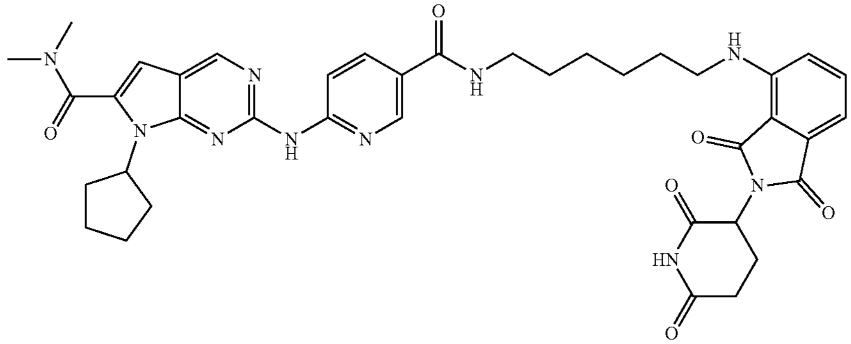 [SMILES: CN(C)C(=O)c1cc2cnc(Nc3ccc(C(=O)NCCCCCCNc4cccc5c4C(=O)N(C4CCC(=O)NC4=O)C5=O)cn3)nc2n1C1CCCC1]

1H NMR (500 MHz, DMSO): δ 11.10 (s, 1H), 10.75 (br s, 1H), 8.95 (s, 1H), 8.79 (s, 1H), 8.56 (t, J 5.4 Hz, 1H), 8.29 (d, J=8.8 Hz, 1H), 8.09 (s, 1H), 7.59 (t, J=7.9 Hz, 1H), 7.11 (d, J=8.5 Hz, 1H), 7.03 (d, J=7.0 Hz, 1H), 6.77 (d, J=2.8 Hz, 1H), 6.55 (s, 1H), 5.06 (dd, J=12.8, 5.4 Hz, 1H), 4.80 (p, J=8.9 Hz, 1H), 3.29 (dd, J=13.5, 7.1 Hz, 5H), 3.07 (s, 6H), 2.93-2.85 (m, 1H), 2.65-2.57 (m, 1H), 2.41-2.38 (m, 2H), 2.05-2.01 (m, 6H), 1.70-1.68 (m, 2H), 1.62-1.55 (m, 4H), 1.40-1.34 (m, 4H).

7-cyclopentyl-2-((4-(((S)-14-((2S,4R)-4-hydroxy-2-((4-(4-methylthiazol-5-yl)benzyl)carbamoyl)pyrrolidine-1-carbonyl)-15,15-dimethyl-12-oxo-3,6,9-trioxa-13-azahexadecyl)carbamoyl)phenyl)amino)-N,N-dimethyl-7H-pyrrolo[2,3-d]pyrimidine-6-carboxamide (HLB-0534332)

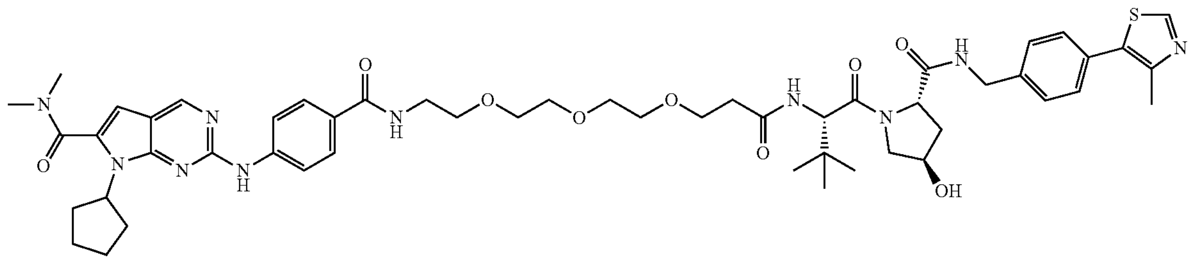 [SMILES: Cc1ncsc1-c1ccc(CNC(=O)[C@@H]2C[C@@H](O)CN2C(=O)[C@@H](NC(=O)CCOCCOCCOCCNC(=O)c2ccc(Nc3ncc4cc(C(=O)N(C)C)n(C5CCCC5)c4n3)cc2)C(C)(C)C)cc1]

1H NMR (500 MHz, DMSO): δ 9.84 (s, 1H), 8.99 (s, 1H), 8.81 (s, 1H), 8.57 (t, J=6.1 Hz, 1H), 8.36 (t, J=5.7 Hz, 1H), 7.92 (d, J=8.6 Hz, 2H), 7.82 (d, J=8.6 Hz, 2H), 7.40 (q, J=8.3 Hz, 4H), 6.63 (s, 1H), 4.76 (p, J=8.7 Hz, 1H), 4.55 (d, J=9.4 Hz, 1H), 4.52-4.37 (m, 2H), 4.36 (br s, 1H), 4.22 (dd, J=15.8, 5.5 Hz, 1H), 3.60-3.50 (m, 16H), 3.41 (q, J=6.0 Hz, 2H), 3.07 (br s, 6H), 2.55 (s, 9H), 2.45 (s, 3H), 2.38-2.31 (m, 1H), 2.06-2.02 (m, 6H), 1.93-1.88 (m, 1H), 1.70-1.69 (m, 2H).

7-cyclopentyl-2-((4-((5-(2-(2,6-dioxopiperidin-3-yl)-1-oxoisoindolin-4-yl)pent-4-yn-1-yl)carbamoyl)-phenyl)amino)-N,N-dimethyl-7H-pyrrolo[2,3-d]pyrimidine-6-carboxamide (HLB-0534333)

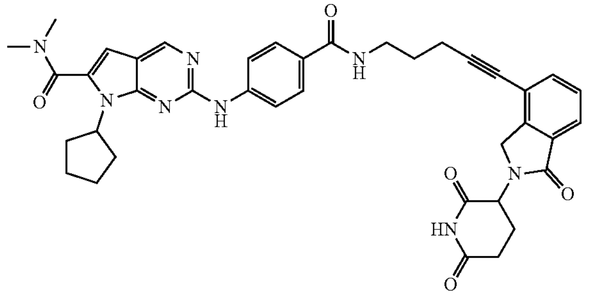 [SMILES: CN(C)C(=O)c1cc2cnc(Nc3ccc(C(=O)NCCCC#Cc4cccc5c4CN(C4CCC(=O)NC4=O)C5=O)cc3)nc2n1C1CCCC1]

1H NMR (500 MHz, DMSO): δ 10.92 (s, 1H), 9.76 (s, 1H), 8.73 (s, 1H), 8.31 (t, J=5.7 Hz, 1H), 7.83 (d, J=8.7 Hz, 2H), 7.74 (d, J=8.7 Hz, 2H), 7.64 (d, J=7.6 Hz, 1H), 7.56 (d, J=7.5 Hz, 1H), 7.45 (t, J=7.6 Hz, 1H), 6.56 (s, 1H), 5.08 (dd, J=13.4, 5.1 Hz, 1H), 4.69 (p, J=9.0 Hz, 1H), 4.44 (d, J=17.8 Hz, 1H), 4.28 (d, J=17.8 Hz, 1H), 3.36 (q, J=6.6 Hz, 2H), 2.99 (br s, 6H), 2.91-2.80 (m, 1H), 2.48 (d, J=9.9 Hz, 3H), 2.30 (q, J=6.0 Hz, 2H), 1.97-1.91 (m, 6H), 1.77 (p, J=7.1 Hz, 2H), 1.64-1.60 (m, 2H).

7-cyclopentyl-2-((4-((3-(2-(2,6-dioxopiperidin-3-yl)-1-oxoisoindolin-4-yl)prop-2-yn-1-yl)carbamoyl)-phenyl)amino)-N,N-dimethyl-7H-pyrrolo[2,3-d]pyrimidine-6-carboxamide (HLB-0534334)

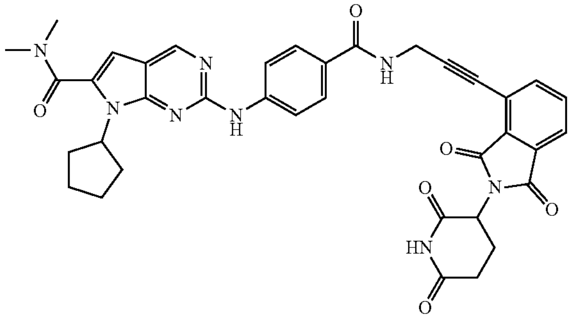 [SMILES: CN(C)C(=O)c1cc2cnc(Nc3ccc(C(=O)NCC#Cc4cccc5c4C(=O)N(C4CCC(=O)NC4=O)C5=O)cc3)nc2n1C1CCCC1]

1H NMR (500 MHz, DMSO): δ 11.01 (s, 1H), 9.88 (s, 1H), 8.88 (t, J=5.5 Hz, 1H), 8.82 (s, 1H), 7.94 (d, J=8.6 Hz, 2H), 7.87 (d, J=8.8 Hz, 2H), 7.76 (d, J=7.5 Hz, 1H), 7.70 (d, J=7.6 Hz, 1H), 7.56 (t, J=7.6 Hz, 1H), 6.63 (s, 1H), 5.15 (dd, J=13.4, 5.1 Hz, 1H), 4.77 (p, J=8.8 Hz, 1H), 4.48 (d, J=17.8 Hz, 1H), 4.42-4.31 (m, 3H), 3.15-3.06 (m, 6H), 2.97-2.86 (m, 1H), 2.78-2.33 (m, 3H), 2.03-2.01 (m, 6H), 1.70-1.69 (m, 2H).

7-cyclopentyl-2-((4-((3-(2-(2,6-dioxopiperidin-3-yl)-1-oxoisoindolin-4-yl)propyl)carbamoyl)phenyl)-amino)-N,N-dimethyl-7H-pyrrolo[2,3-d]pyrimidine-6-carboxamide (HLB-0534335)

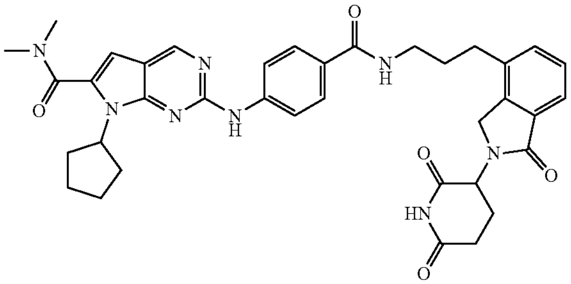 [SMILES: CN(C)C(=O)c1cc2cnc(Nc3ccc(C(=O)NCCCc4cccc5c4CN(C4CCC(=O)NC4=O)C5=O)cc3)nc2n1C1CCCC1]

1H NMR (500 MHz, DMSO): δ 10.92 (s, 1H), 9.76 (s, 1H), 8.73 (s, 1H), 8.27 (t, J=5.7 Hz, 1H), 7.83 (d, J=8.9 Hz, 2H), 7.74 (d, J=8.6 Hz, 2H), 7.51 (d, J=7.3 Hz, 1H), 7.46 (d, J=7.4 Hz, 1H), 7.41 (t, J=7.4 Hz, 1H), 6.56 (s, 1H), 5.06 (dd, J=13.3, 5.1 Hz, 1H), 4.69 (p, J=8.9 Hz, 1H), 4.40 (d, J=17.1 Hz, 1H), 4.25 (d, J=17.1 Hz, 1H), 3.24 (q, J=6.7 Hz, 2H), 3.00 (br s, 6H), 2.85 (ddd, J=17.9, 13.6, 5.4 Hz, 1H), 2.70-2.61 (m, 2H), 2.57-2.54 (m, 1H), 2.34-2.25 (m, 1H), 1.99-1.89 (m, 6H), 1.82 (p, J=7.4 Hz, 2H), 1.64-1.60 (m, J=6.7 Hz, 2H).

7-cyclopentyl-2-((4-(7-((2-(2,6-dioxopiperidin-3-yl)-1,3-dioxoisoindolin-4-yl)oxy)heptanamido)-phenyl) amino)-N,N-dimethyl-7H-pyrrolo[2,3-d]pyrimidine-6-carboxamide (HLB-0534337)

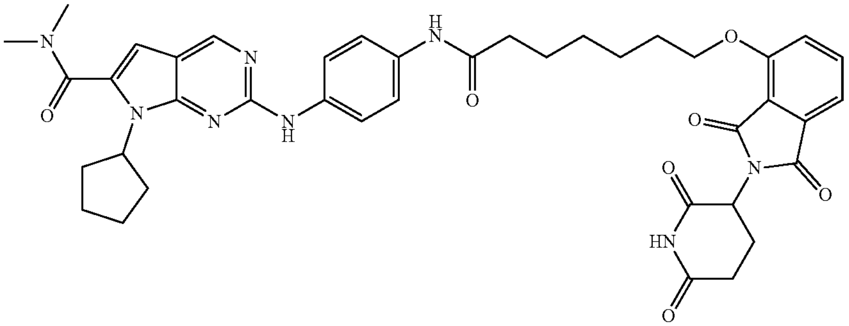 [SMILES: CN(C)C(=O)c1cc2cnc(Nc3ccc(NC(=O)CCCCCCOc4cccc5c4C(=O)N(C4CCC(=O)NC4=O)C5=O)cc3)nc2n1C1CCCC1]

1H NMR (500 MHz, DMSO-d6): δ 11.09 (s, 1H), 9.75 (s, 1H), 9.47 (s, 1H), 8.73 (s, 1H), 7.80 (dd, J=8.5, 7.2 Hz, 1H), 7.73-7.68 (m, 2H), 7.51 (dd, J=8.8, 3.6 Hz, 3H), 7.44 (d, J=7.2 Hz. 1H), 6.59 (s, 1H), 5.08 (dd, J=12.7, 5.5 Hz, 1H), 4.70 (q, J=8.8 Hz, 1H), 4.21 (t, J=6.4 Hz, 2H), 3.05 (s, 6H), 2.87 (ddd, J=16.9, 13.8, 5.5 Hz, 1H), 2.62-2.58 (m, 1H), 2.58-2.54 (m, 1H), 2.46-2.42 (m, 1H), 2.29 (t, J=7.4 Hz, 2H), 1.98-1.95 (m, 5H), 1.95-1.92 (m, 1H), 1.78 (p, J=6.5 Hz, 2H), 1.67-1.57 (m, 4H), 1.50 (p, J=7.5 Hz, 2H), 1.39 (q, J=7.8 Hz, 2H).

7-cyclopentyl-2-((4-((3-(2-((2-(2,6-dioxopiperidin-3-yl)-1,3-dioxoisoindolin-4-yl)oxy)acetamido)pro-pyl) carbamoyl)phenyl)amino)-N,N-dimethyl-7H-pyrrolo [2,3-d]pyrimidine-6-carboxamide (HLB-0534336)

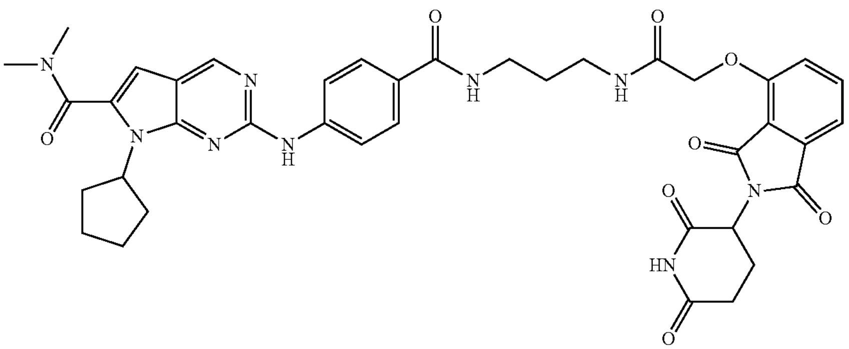 [SMILES: CN(C)C(=O)c1cc2cnc(Nc3ccc(C(=O)NCCCNC(=O)COc4cccc5c4C(=O)N(C4CCC(=O)NC4=O)C5=O)cc3)nc2n1C1CCCC1]

1H NMR (500 MHz, DMSO): δ 11.10 (s, 1H), 9.85 (s, 1H), 8.81 (s, 1H), 8.30 (t, J=5.7 Hz, 1H), 8.04 (t, J=5.8 Hz, 1H), 7.89 (d, J=8.8 Hz, 2H), 7.85-7.78 (m, 3H), 7.49 (d, J=7.2 Hz, 1H), 7.41 (d, J=8.5 Hz, 1H), 6.63 (s, 1H), 5.12 (dd, J=12.7, 5.4 Hz, 1H), 4.79-4.71 (m, 3H), 3.29-3.19 (m, 4H), 3.06 (br s, 6H), 2.88 (ddd, J=17.0, 13.8, 5.4 Hz, 1H), 2.63-2.53 (m, 1H), 2.05-1.97 (m, 6H), 1.75-1.66 (m, 4H).

7-cyclopentyl-2-((5-((6-((2-(2,6-dioxopiperidin-3-yl)-1,3-dioxoisoindolin-4-yl)oxy)hexyl)carbamo-yl)pyridin-2-yl)amino)-N,N-dimethyl-7H-pyrrolo[2,3-d]pyrimidine-6-carboxamide (14)

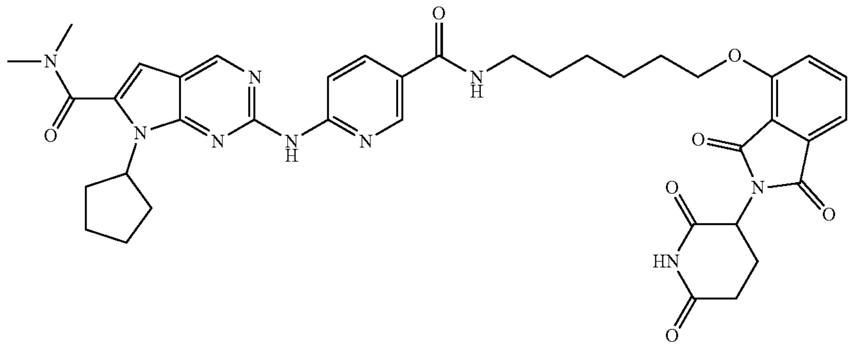 [SMILES: CN(C)C(=O)c1cc2cnc(Nc3ccc(C(=O)NCCCCCCOc4cccc5c4C(=O)N(C4CCC(=O)NC4=O)C5=O)cn3)nc2n1C1CCCC1]

1H NMR (500 MHz, DMSO): δ 11.09 (s, 1H), 10.77 (br s, 1H), 8.95 (s, 1H), 8.78 (s, 1H), 8.56 (t, J=5.7 Hz, 1H), 8.29 (dd, J=8.8, 2.4 Hz, 1H), 8.07 (d, J=8.9 Hz, 1H), 7.80 (t, J=7.9 Hz. 1H), 7.51 (d, J=8.5 Hz, 1H), 7.44 (d, J=7.2 Hz, 1H), 6.76 (s, 1H), 5.08 (dd, J=12.7, 5.4 Hz, 1H), 4.79 (p, J=8.8 Hz, 1H), 4.22 (t, J=6.4 Hz, 2H). 3.29 (q, J=6.6 Hz, 2H), 3.06 (s, 6H), 2.88 (ddd, J=16.9, 13.8, 5.5 Hz, 1H), 2.60-2.51 (m, 1H), 2.41-2.36 (m, 2H), 2.05-1.99 (m, 6H), 1.78 (p, J=6.8 Hz, 2H), 1.69-1.67 (m, 2H), 1.61-1.48 (m, 4H), 1.42 (q, J=7.4, 6.9 Hz, 2H).

The following compounds, representing a different chemotype, were made by methods similar to those reported above.

N-(4-((6-acetyl-8-cyclopentyl-5-methyl-7-oxo-7,8-dihydropyrido[2,3-d]pyrimidin-2-yl)amino)phenyl)-7-((2-(2,6-dioxopiperidin-3-yl)-1,3-dioxoisoindolin-4-yl)oxy)heptanamide (19)

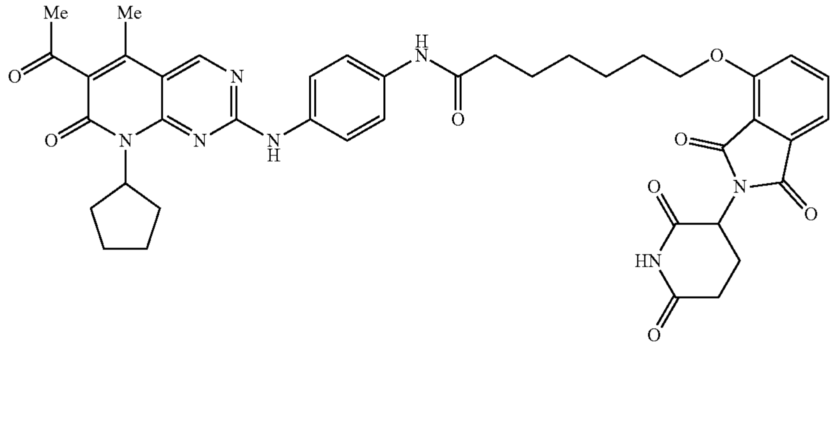 [SMILES: CC(=O)c1c(C)c2cnc(Nc3ccc(NC(=O)CCCCCCOc4cccc5c4C(=O)N(C4CCC(=O)NC4=O)C5=O)cc3)nc2n(C2CCCC2)c1=O]

1H NMR (500 MHz, DMSO-d6): δ 11.09 (s, 1H), 10.14-9.96 (m, 1H), 9.83 (s, 1H), 8.94 (s, 1H), 7.80 (t, J=7.9 Hz, 1H), 7.62-7.53 (m, 4H), 7.51 (d, J=8.5 Hz, 1H), 7.44 (d, J=7.3 Hz, 1H), 5.86-5.83 (m, 1H), 5.08 (dd, J=12.7, 5.5 Hz, 1H), 4.21 (t, J=6.3 Hz, 2H), 2.98-2.78 (m, 1H), 2.67-2.54 (m, 2H), 2.42 (s, 3H), 2.36 (s, 1H), 2.30 (s, 4H), 2.26-2.23 (m, 2H), 2.05-1.99 (m, 1H), 1.92-1.88 (m, 2H), 1.80-1.76 (m, 4H), 1.66-1.56 (m, 4H), 1.52-1.47 (m, 2H), 1.42-1.37 (m, 2H).

4-((6-acetyl-8-cyclopentyl-5-methyl-7-oxo-7,8-dihydropyrido[2,3-d]pyrimidin-2-yl)amino)-N-(6-((2-(2,6-dioxopiperidin-3-yl)-1,3-dioxoisoindolin- 4-yl)oxy)hexyl)benzamide (16)

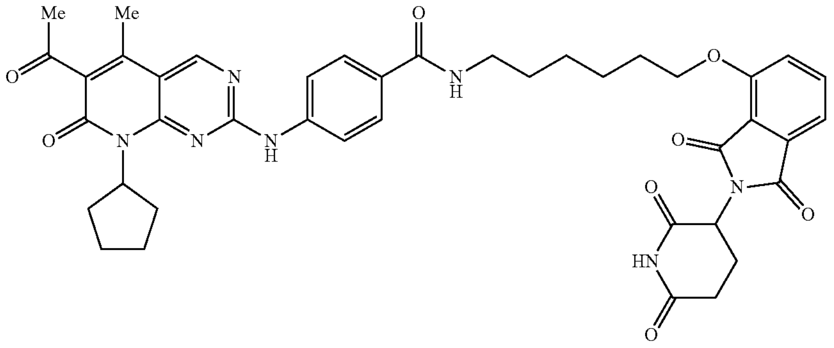 [SMILES: CC(=O)c1c(C)c2cnc(Nc3ccc(C(=O)NCCCCCCOc4cccc5c4C(=O)N(C4CCC(=O)NC4=O)C5=O)cc3)nc2n(C2CCCC2)c1=O]

1H NMR (500 MHz, DMSO-d6): δ 11.09 (s, 1H), 10.36 (s, 1H), 9.02 (s, 1H), 8.33 (t, J=5.6 Hz, 1H), 7.87-7.77 (m, 5H), 7.51 (d, J=8.6 Hz, 1H), 7.43 (d, J=7.2 Hz, 1H), 5.90 (p, J=8.9 Hz, 1H), 5.08 (dd, J=12.7, 5.4 Hz, 1H), 4.21 (t, J=6.4 Hz, 2H), 3.29-3.23 (m, 2H), 2.88 (ddd, J=17.0, 13.8, 5.5 Hz, 1H), 2.62-2.51 (m, 1H), 2.43 (s, 3H), 2.33 (s, 3H), 2.28-2.21 (m, 2H), 2.06-1.92 (m, 3H), 1.88-1.73 (m, 4H), 1.68-1.60 (m, 2H), 1.60-1.46 (m, 4H), 1.44-1.35 (m, 2H).

The following compounds, representing a different chemotype, were made by methods similar to those reported above.

N-(6-((2-(2,6-dioxopiperidin-3-yl)-1,3-dioxoisoindolin-4-yl)oxy)hexyl)-4-((5-fluoro-4-(4-fluoro-1-isopropyl-2-methyl-1H-benzo[d]imidazol-6-yl)pyrimidin-2-yl)amino)benzamide (17)

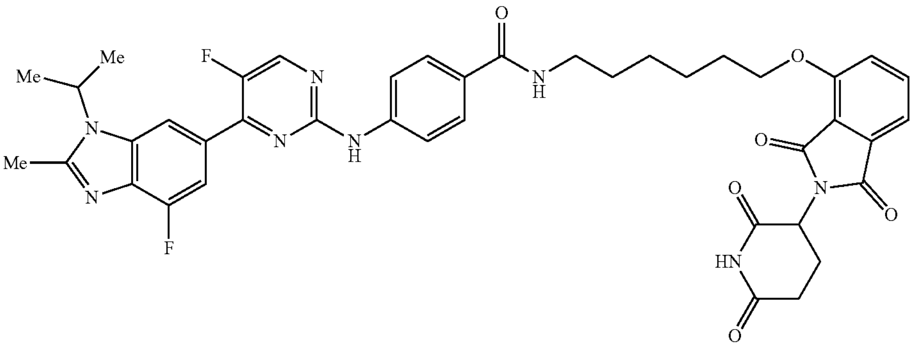 [SMILES: Cc1nc2c(F)cc(-c3nc(Nc4ccc(C(=O)NCCCCCCOc5cccc6c5C(=O)N(C5CCC(=O)NC5=O)C6=O)cc4)ncc3F)cc2n1C(C)C]

1H NMR (500 MHz, DMSO-d6): δ 11.09 (s, 1H), 10.06 (s, 1H), 8.71 (d, J=3.7 Hz, 1H), 8.31-8.23 (m, 2H), 7.87 (d, J=8.5 Hz, 2H), 7.84-7.76 (m, 3H), 7.70 (d, J=11.9 Hz, 1H), 7.51 (d, J=8.6 Hz, 1H), 7.43 (d, J=7.2 Hz, 1H), 5.07 (dd, J=12.8, 5.3 Hz, 1H), 4.91-4.84 (m, 1H), 4.21 (t, J=6.4 Hz, 2H), 3.26 (q, J=6.5 Hz, 2H), 2.94-2.80 (m, 1H), 2.66 (s, 3H), 2.64 (s, 2H), 2.64-2.59 (m, 2H), 2.36 (s, 1H), 2.05-1.99 (m, 1H), 1.81-1.73 (m, 2H), 1.63 (d, J=6.9 Hz, 6H), 1.59-1.46 (m, 4H), 1.43-1.38 (m, 2H).

7-((2-(2,6-dioxopiperidin-3-yl)-1,3-dioxoisoindolin-4-yl)oxy)-N-(4-((5-fluoro-4-(4-fluoro-1-isopropyl-2-methyl-1H-benzo[d]imidazol-6-yl)pyrimidin-2-yl)amino)phenyl)heptanamide (18)

radioimmnuoprecipitation assay (RIPA) lysis buffer (50 mM Tris-HCl pH 7.4, 150 mM NaCl, 1% NP-40, 0.5% sodium deoxycholate, 0.1% SDS, 5 mM EDTA, 1 mM EGTA) supplemented with 1% protease inhibitor cocktail (Roche cOmplete) and 1% phosphatase inhibitor cocktail (PhosS-TOP). Cell lysates were incubated on ice for 15 mins and then kept at −80° C. before further use. The lysates were thawed on ice and the supernatants were collected after centrifugation (@11,000 rpm) for 15 min at 4° C. The protein concentration was determined using the Pierce BCA protein Assay kit and normalized before the samples were reduced in SOS sample buffer and denatured at 95° C. in a heated block for 10 mins. An equal amount of protein samples (10-30 μg per lane) were resolved using 4-20% Tris-glycine gels and transferred onto PVDF blotting mem-

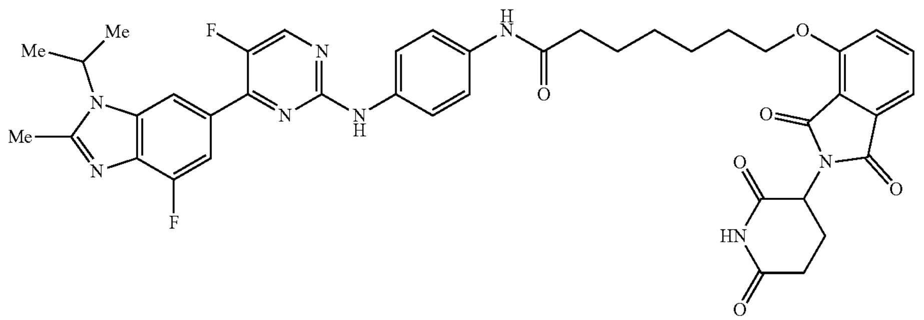 [SMILES: Cc1nc2c(F)cc(-c3nc(Nc4ccc(NC(=O)CCCCCCOc5cccc6c5C(=O)N(C5CCC(=O)NC5=O)C6=O)cc4)ncc3F)cc2n1C(C)C]

1H NMR (500 MHz, DMSO-d6): δ 11.09 (s, 1H), 9.78 (s, 1H), 9.68 (s, 1H), 8.62 (d, J=3.8 Hz, 1H), 8.28 (s, 1H), 7.80 (dd, J=8.5, 7.3 Hz, 1H), 7.72-7.65 (m, 3H), 7.55 (d, J=2.0 Hz, 1H), 7.56-7.49 (m, 2H), 7.43 (d, J=7.2 Hz, 1H), 5.08 (dd, J=12.7, 5.5 Hz, 1H), 4.87 (p, J=6.8 Hz, 1H), 4.21 (t, J=6.4 Hz, 2H), 2.87 (ddd, J=16.9, 13.5, 5.3 Hz, 1H), 2.66 (s, 3H), 2.62-2.58 (m, 1H), 2.58-2.51 (m, 1H), 2.30 (t, J=7.4 Hz, 2H), 2.05-1.99 (m, 1H), 1.78 (p, J=6.6 Hz, 2H), 1.63 (d, J=6.9 Hz, 8H), 1.50 (p, J=7.6 Hz, 2H), 1.44-1.36 (m, 2H).

Biological Evaluations of Aurora-A Degraders:

a. Cell Line and Cell Culture:

MCF-7 cells were cultured in complete Dulbecco's modified Eagle medium (DMEM) supplemented with 10% (vol/vol) heat-inactivated fetal bovine serum (FBS), 100 U/ml penicillin and 100 μg/ml streptomycin. HCC38 cells were cultured in RPMI medium with 10% FBS, 100 U/ml penicillin and 100 μg/ml streptomycin. Huh7 cells were cultured in DMEM medium with 10% FBS, 100 U/ml penicillin and 100 μg/ml streptomycin supplemented with 1% MEM non-essential amino acids (SIGMA M7145). IMR-32 and SK-N-BE(2) cells were cultured in Eagle's Minimum Essential Medium (EMEM) with 10% FBS, 100 U/ml penicillin and 100 μg/ml streptomycin. All the cell lines were maintained in a humidified incubator at 37° C. and 5% $CO_2$.

b. Immunoblotting:

Cells were treated with 13 and other compounds at indicated concentrations and incubation time. Cells were gently rinsed once with ice-cold PBS and then lysed in branes. Primary antibodies CDK4 (DCS-35, 1:2000), N-Myc (B8.4.B, 1:5000), p21 (F-5, 1:500), p53 (DO-1, 1:1000), Aurora-A (1G4, 1:1000), β-actin (A1978, 1:2000) were used for immunoblotting. The images were detected using Li-Cor Odyssey Fc imaging system and the immunoblots were quantified by densitometry using ImageJ software.

c. Viability Assays Using Alamar Blue:

Cancer cells were seeded in media (50 μL) 24 h prior to treatment with compounds in 96-well plates. For MCF-7 and Huh7 cells, the seeding density is 2,500 cells/well; for HCC38, the density is 2,000 cells/well; and for IMR-32 and SK-N-BE(s), the density is 5,000 cells/well. Compounds were serially diluted in pre-warmed media and dosed to cells (final volume=100 μL; final DMSO concentration=0.5%). Approximately 2 hours before the end of the treatment period (5 days for MCF-7, HCC38 and Huh7; and 3 days for SK-N-BE(2) and IMR-32), Alamar Blue (Invitrogen) cell viability reagent was added to each well (10 μL). After 2 hours treatment period, the fluorescence of each well was read using a BioTek Synergy H1 plate reader. Cytotoxicity curves (sigmoidal dose response) were generated using GraphPad Prism (v. 8.4.1).

What is claimed is:

1. A compound of the Formula:

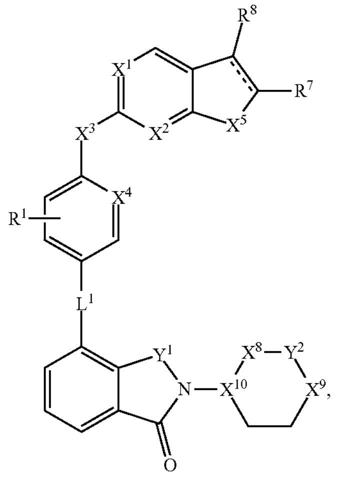

or a pharmaceutically acceptable salt or solvate thereof, wherein:

the dashed line can form a double bond;

$R^7$ and $R^8$ are each, independently H, alkyl, aryl, amino, acyl or amido;

$X^5$ is N—$Z^1$ or CH—$Z^1$, wherein $Z^1$ is a cycloalkyl group;

$X^1$ and $X^2$ each independently CH or N;

$X^3$ is -alkyl-, —O—, —S— or $NR^4$, wherein $R^4$ is H or alkyl;

$X^4$ is CH;

$R^1$ is H, halo, amino, alkyl, aryl or heterocyclyl;

$L^1$ is acyl, alkyl, alkenyl or alkynyl, and combinations thereof, optionally interrupted by one or more heteroatoms;

$Y^1$ is $CH_2$ or C(O);

$X^8$ and $X^9$ are each independently $CR^{16}R^{17}$, wherein $R^{16}$ and $R^{17}$ are each independently H, alkyl or, $R^{16}$ and $R^{17}$ together with the atom to which they are attached form a C(O) group;

$X^{10}$ is N or $CR^{18}$, wherein $R^{18}$ is H or alkyl;

$Y^2$ is $NR^{19}$, wherein $R^{19}$ is H or alkyl.

2. The compound of claim 1, wherein $X^1$ and $X^2$ are N and the group:

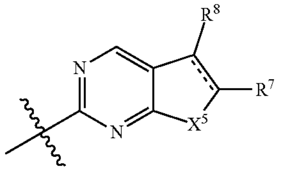

is a group of the formula:

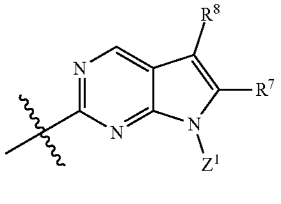

3. The compound of claim 1, wherein $L^1$ is:

-(alkyl-$X^{11}$)$_g$-alkyl-,

-(alkyl-$X^{11}$)$_g$-alkynyl-,

—C(O)$NR^{13}$—$X^{11}$-(alkyl-$X^{11}$)$_g$-alkyl-,

—C(O)$NR^{13}$—$X^{11}$-(alkyl-$X^{11}$)$_g$-alkyl-C(O)—,

—C(O)$NR^{13}$—$X^{11}$-(alkyl-$X^{11}$)$_g$-alkynyl-,

—C(O)$NR^{13}$—$X^{11}$-(alkyl-$X^{11}$)$_g$-alkynyl-C(O)—,

—C(O)$NR^{13}$—$X^{11}$-(alkyl-$X^{11}$)$_g$-alkyl-$NR^{13}$—,

—C(O)$NR^{13}$—$X^{11}$-(alkyl-$X^{11}$)$_g$-alkyl-C(O)—$NR^{13}$—,

—C(O)$NR^{13}$—$X^{11}$-(alkyl-$X^{11}$)$_g$-alkynyl-$NR^{13}$—,

—C(O)$NR^{13}$—$X^{11}$-(alkyl-$X^{11}$)$_g$-alkynyl-C(O)—$NR^{13}$—,

—$NR^{13}$—$X^{11}$-(alkyl-$X^{11}$)$_g$-alkyl-,

—$NR^{13}$—$X^{11}$-(alkyl-$X^{11}$)$_g$-alkyl-C(O)—,

—$NR^{13}$—$X^{11}$-(alkyl-$X^{11}$)$_g$-alkynyl-,

—$NR^{13}$—$X^{11}$-(alkyl-$X^{11}$)$_g$-alkynyl-C(O)—,

—$NR^{13}$—$X^{11}$-(alkyl-$X^{1}$)$_g$-alkyl-$NR^{13}$—,

—$NR^{13}$—$X^{11}$-(alkyl-$X^{11}$)$_g$-alkyl-O—,

—$NR^{13}$—$X^{11}$-(alkyl-$X^{11}$)$_g$-alkyl-C(O)—$NR^{13}$—,

—$NR^{13}$—$X^{11}$-(alkyl-$X^{11}$)$_g$-alkynyl-$NR^{13}$—,

—$NR^{13}$—$X^{11}$-(alkyl-$X^{1}$)$_g$-alkynyl-C(O)—$NR^{13}$—,

—C(O)—$X^{11}$-(alkyl-$X^{11}$)$_g$-alkyl-,

—C(O)—$X^{11}$-(alkyl-$X^{11}$)$_g$-alkyl-C(O)—,

—C(O)—$X^{11}$-(alkyl-$X^{11}$)$_g$-alkynyl-,

—C(O)—$X^{11}$-(alkyl-$X^{11}$)$_g$-alkynyl-C(O)—,

—C(O)—$X^{11}$-(alkyl-$X^{11}$)$_g$-alkyl-$NR^{13}$—,

—C(O)—$X^{11}$-(alkyl-$X^{11}$)$_g$-alkyl-C(O)—$NR^{13}$—,

—C(O)—$X^{11}$-(alkyl-$X^{11}$)$_g$-alkynyl-$NR^{13}$—,

—C(O)—$X^{11}$-(alkyl-$X^{11}$)$_g$-alkynyl-C(O)—$NR^{13}$—,

—NH—$X^{11}$—C(O)—$X^{11}$-alkyl and combinations thereof, wherein:

each $X^{11}$ is, independently, a bond, alkyl, —O—, —$NR^{13}$—, or —S(O)n- wherein n is 0, 1, or 2; $R^{13}$ is H, halo, or alkyl; and g is an integer from 0 to 20 and each group (alkyl-$X^{11}$) being the same or different.

4. The compound of claim 1, wherein $L^1$ is:

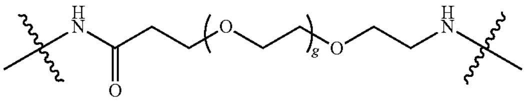,

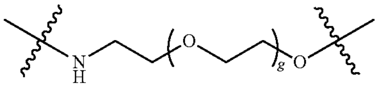,

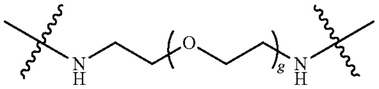,

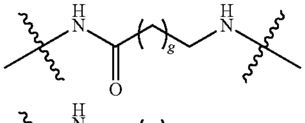,

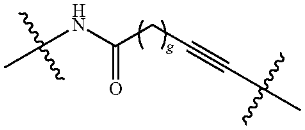,

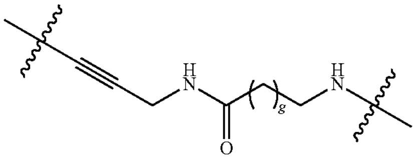 or

-continued
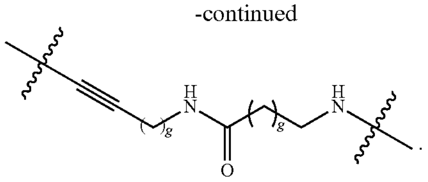
and
wherein g is an integer from 0 to 20.
5. The compound of claim 1, wherein the compound is a compound of the formula:
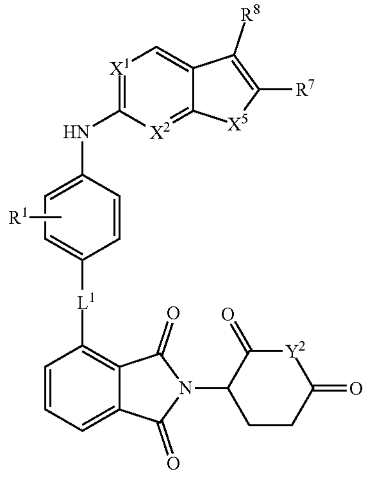
or a pharmaceutically acceptable salt or solvate thereof.
6. The compound of claim 1, wherein the compound is a compound of the formula:
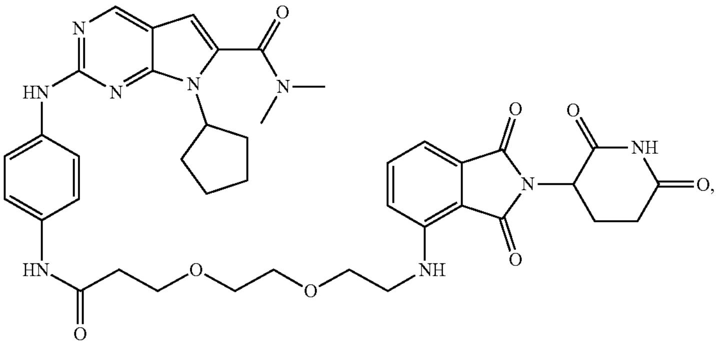
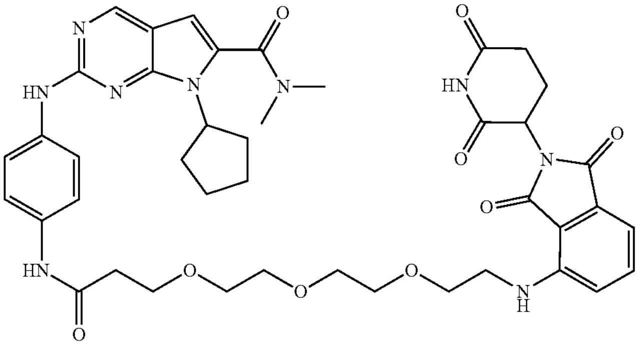
,
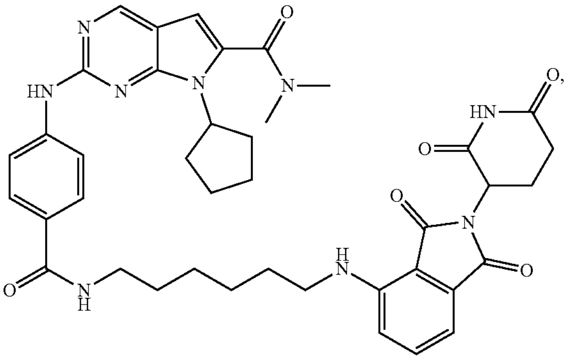

-continued
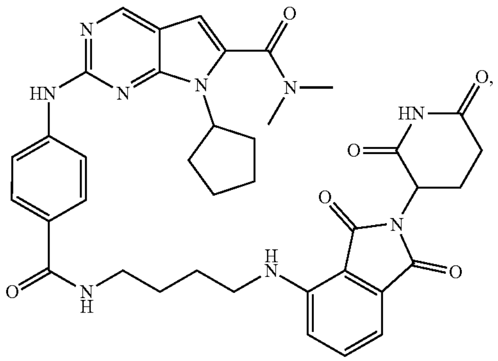
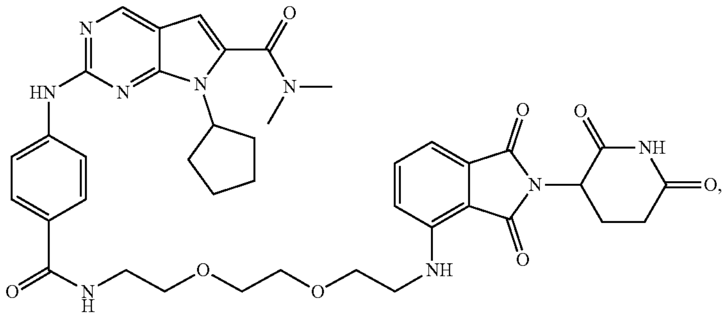
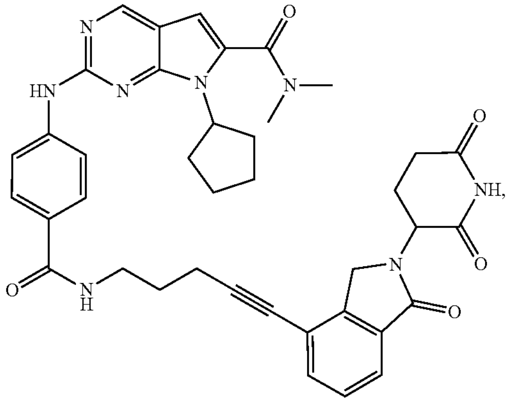
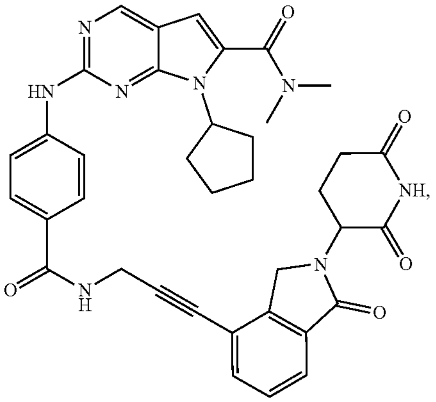
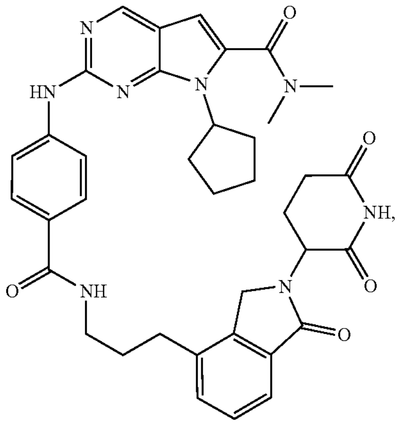
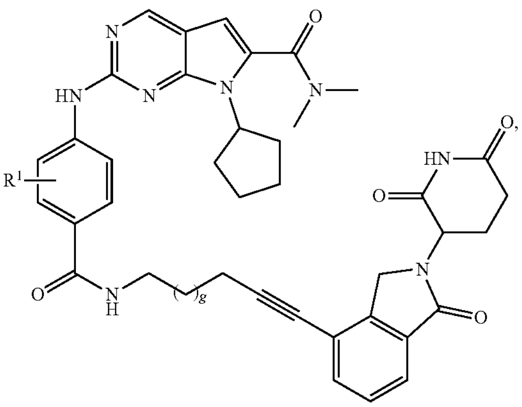

-continued
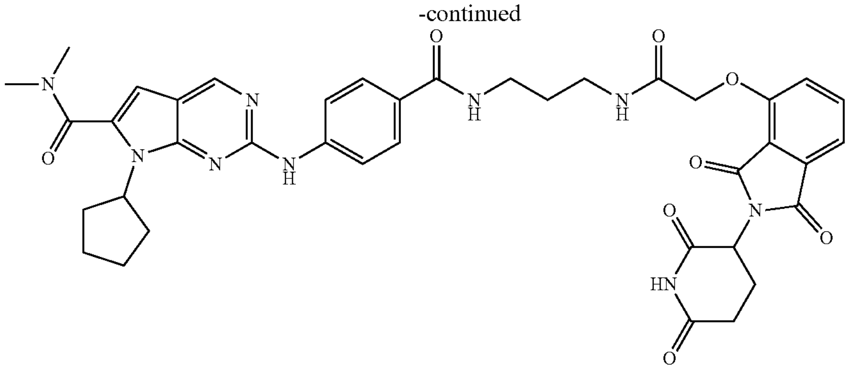
,
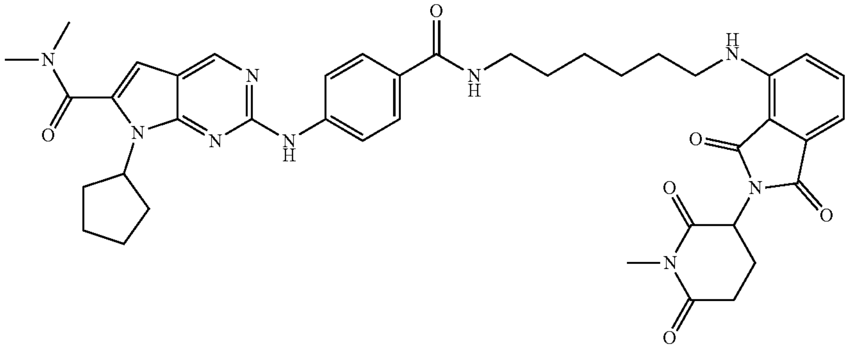
,
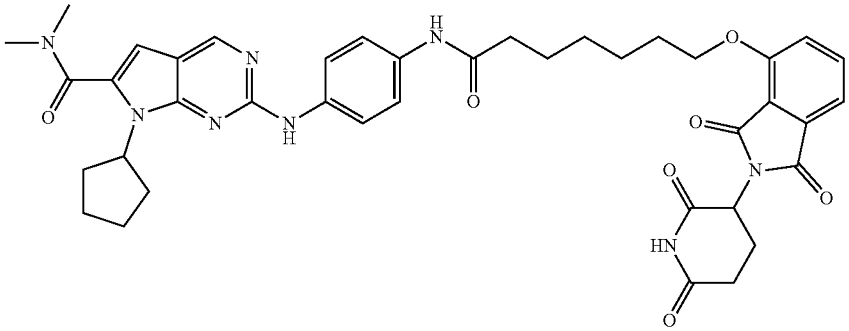
,
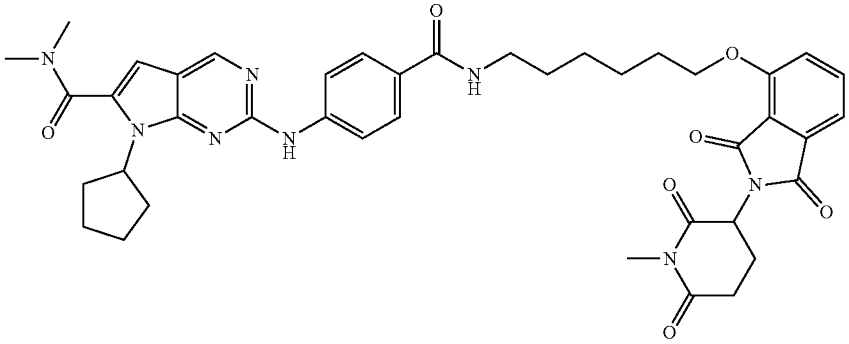
,
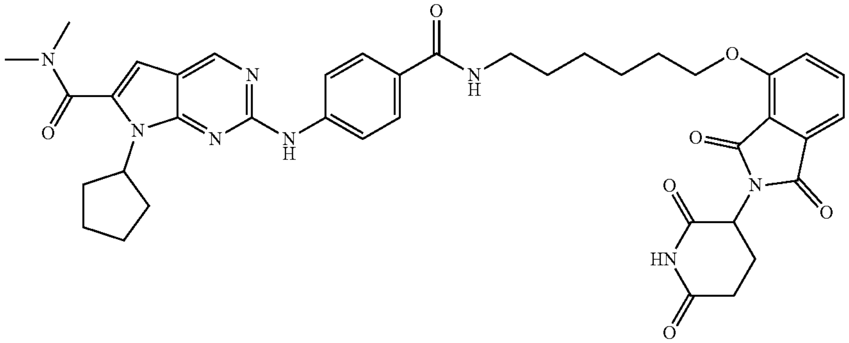

or a pharmaceutically acceptable salt or solvate thereof, wherein g is an integer from 0 to 20.

7. A pharmaceutical composition comprising one or more compounds of claim 1 and one or more pharmaceutically acceptable excipients.

8. A method of modulating N-Myc comprising administering a therapeutically effective amount of a compound of claim 1, or a pharmaceutical composition comprising said compound, to a subject in need thereof; or a method of modulating Aurora kinase A comprising administering a therapeutically effective amount of a compound of claim 1, or a pharmaceutical composition comprising said compound, to a subject in need thereof; or method of modulating CDK4/6 comprising administering a therapeutically effective amount of a compound of claim 1, or a pharmaceutical composition comprising said compound, to a subject in need thereof; or method of modulating Cyclin Ds comprising administering a therapeutically effective amount of a compound of claim 1, or a pharmaceutical composition comprising said compound, to a subject in need thereof.

9. A method for treating cancer comprising administering a therapeutically effective amount of one or more compounds of claim 1, or a pharmaceutical composition comprising said compound, to a subject in need thereof.

10. The method of claim 9, wherein the cancer is neuroblastoma, medulloblastoma, small-cell lung cancer, and neuroendocrine prostate cancer or the cancer is leukemia, lymphoma, ovarian cancer, breast cancer, brain cancer, non-small cell lung cancer or soft-tissue sarcoma.

11. The compound of claim 1, wherein the compound is a compound of the formula:

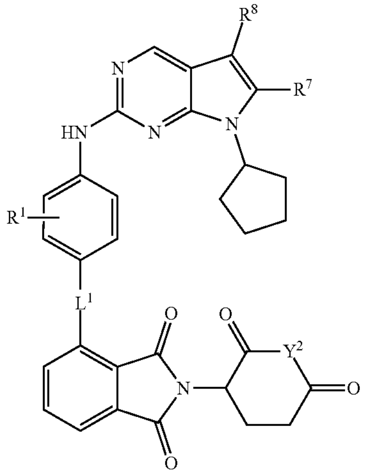

or a pharmaceutically acceptable salt or solvate thereof.

12. The compound of claim 1, wherein the compound is a compound of the formula:

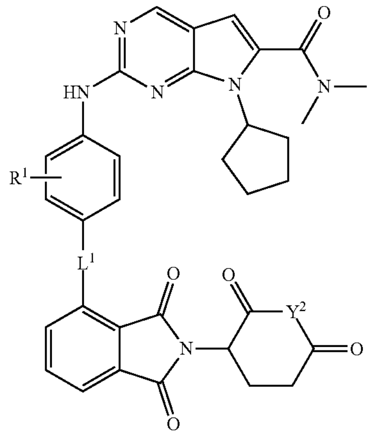

or a pharmaceutically acceptable salt or solvate thereof.

13. The compound of claim 1, wherein the compound is a compound of the formula:

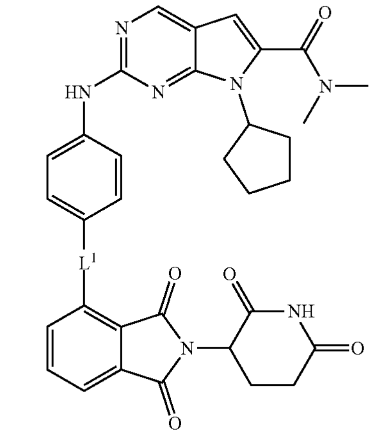

or a pharmaceutically acceptable salt or solvate thereof.

* * * * *